(12) United States Patent
Payne et al.

(10) Patent No.: US 7,202,346 B2
(45) Date of Patent: Apr. 10, 2007

(54) ANTIBODIES TO NON-SHED MUC1 AND MUC16, AND USES THEREOF

(75) Inventors: Gillian Payne, Waban, MA (US); Thomas Chittenden, Sudbury, MA (US); Viktor Goldmakher, Newton, MA (US); Philip Chun, Malden, MA (US); Kristin Sneider-Mulready, Framingham, MA (US); Carol A. Vater, Cambridge, MA (US)

(73) Assignee: Immunogen Inc., Cambridge, MA (US)

( * ) Notice: Subject to any disclaimer, the term of this patent is extended or adjusted under 35 U.S.C. 154(b) by 276 days.

(21) Appl. No.: 10/612,090

(22) Filed: Jul. 3, 2003

(65) Prior Publication Data

US 2004/0057952 A1    Mar. 25, 2004

Related U.S. Application Data

(60) Provisional application No. 60/393,094, filed on Jul. 3, 2002.

(51) Int. Cl.
*C07K 16/00*    (2006.01)

(52) U.S. Cl. ............... 530/388.1; 530/387.3; 530/350; 530/380; 530/385; 530/387.1; 530/387.7; 424/134.1; 424/135.1; 424/141.1; 424/155.1; 424/142.1; 424/178.1; 424/85.1; 435/7.9; 435/188; 435/320.1; 525/54.1

(58) Field of Classification Search ............ 530/387.3, 530/350, 380, 385, 387.1, 387.7, 388.1; 424/134.1, 424/135.1, 141.1, 155.1, 142.1, 178.1, 85.1; 435/7.9, 188, 320.1; 525/54.1
See application file for complete search history.

(56) References Cited

U.S. PATENT DOCUMENTS

| | | | |
|---|---|---|---|
| 5,776,427 A * | 7/1998 | Thorpe et al. | 424/1.49 |
| 5,846,545 A * | 12/1998 | Chari et al. | 424/195.11 |
| 6,166,176 A * | 12/2000 | Radosevich | 530/300 |
| 6,333,410 B1 * | 12/2001 | Chari et al. | 540/456 |
| 6,340,701 B1 * | 1/2002 | Chari et al. | 514/449 |
| 6,512,096 B2 * | 1/2003 | Weiner et al. | 530/388.85 |
| 2003/0170237 A1 * | 9/2003 | Ni et al. | 424/144.1 |
| 2003/0235868 A1 * | 12/2003 | Hoogenboom et al. | 435/7.2 |
| 2004/0146862 A1 * | 7/2004 | Mack et al. | 435/6 |
| 2005/0053606 A1 * | 3/2005 | Kufe et al. | 424/155.1 |
| 2005/0064518 A1 * | 3/2005 | Albone et al. | 435/7.2 |

FOREIGN PATENT DOCUMENTS

| | | |
|---|---|---|
| WO | WO 96/03502 | 2/1996 |
| WO | WO 01/090197 | 11/2001 |
| WO | WO 02/06317 | 1/2002 |
| WO | WO 02/22685 | 3/2002 |
| WO | WO 02/078598 | 10/2002 |
| WO | WO 03/089451 | 10/2003 |

OTHER PUBLICATIONS

Hartman et al (Int. J. Cancer 1999; 82:256-267).*
Zrihan-Licht et al (Eur. J. Biochem. 1994; 224:787-795).*
Parry et al (Biochem, Biophys. Res. Comm. 2001; 283:715-720).*
William E. Paul, M.D. ed., Fundamental Immunology 242 3d ed. 1993.*
Colman et al (Research in Immunology 1994, 145:33-36).*
Ibragimova and Eade (Biophysical Journal, Oct. 1999, vol. 77, pp. 2191-2198).*
Rudikoff et al (Proc. Natl. Acad. Sci. USA 1982 vol. 79 p. 1979).*
O'Brien et al, *Tumor Biology*, 22 (6):348-366 (2001).
Pietersz et al, *Vaccine*, 18 (19):2059-2071 (2000).
Taylor-Papadimitriou et al, *Biochimica et Biophysica ACTA, Molecular Basis of Disease*, 1455 (2-3):301-313 (1999).

* cited by examiner

*Primary Examiner*—Sheela Huff
*Assistant Examiner*—Parithosh K. Tungaturthi
(74) *Attorney, Agent, or Firm*—Sughrue Mion, PLLC

(57) ABSTRACT

The present invention relates to antibodies, antibody fragments, conjugates of antibodies and antibody fragments with cytotoxic agents, and hybridomas producing the antibodies and antibody fragments, where the antibodies and antibody fragments recognize extracellular epitopes of plasma membrane proteins that are not released into the extracellular fluid, and to methods for the detection, monitoring and treatment of malignancies such as breast cancer and ovarian cancer using the antibodies, antibody fragments and conjugates.

37 Claims, 26 Drawing Sheets

Figure 1A

Muc1 Exemplary Protein – (SEQ ID NO:19)

Signal Peptide Cleavage (G|S; A|S)

```
  1    MTPGTQSPFF LLLLLTVLTV VTGSGHASST PGGEKETSAT QRSSVPSSTE KNAVSMTSSV LSSHSPGSGS
 71    STTQGQDVTL APATEPASGS AATWGQDVTS VPVTRPALGS TTPPAHDVTS APDNKPAPGS TAPPAHGVTS
141    APDTRPPPGS TAPPAHGVTS ASGSASGSAS APDTRPAPGS TAPPAHGVTS APDNRPALAS
211    TAPPVHNVTS ASGSASGSAS TLVHNGTSAR ATTTPASKST PFSIPSHHSD TPTTLASHST KTDASSTHHS
281    TVPPLTSSNH STSPQLSTGV SFFFLSFHIS NLQFNSSLED PSTDYYQELQ RDISEMFLQI YKQGGFLGLS
```
Post-translational cleavage site (G|S)

```
351    NIKFRPGSVV VQLTLAFREG TINVHDVETQ FNQYKTEAAS RYNLTISDVS VSDVPFPFSA QSGAGVPGWG
421    IALLVLVCVL VALAIVYLIA LAVCQCRRKN YGQLDIFPAR DTYHPMSEYP TYHTHGRYVP PSSTDRSPYE
```
Transmembrane region (TMR)

```
491    KVSAGNGGSS LSYTNPAVAA TSANL        (SEQ ID NO:19; NM_002456)
```

Figure 1B

Muc1 juxtamembrane domain-GST Fusion

GST plus amino acids 337-422 of Muc1

GST-FLQI YKQGGFLGLS NIKFRPGSVV VQLTLAFREG TINVHDVETQ FNQYKTEAAS RYNLTISDVS VSDVPFPFSA QSGAGVPGWG IA  (SEQ ID NO:7)

Synthetic Peptides

| | | | |
|---|---|---|---|
| Peptide a | 21 amino acids (362-382) | QLTLAFREGTINVHDVETQFN | (SEQ ID NO:8) |
| Peptide b | 21 amino acids (383-403) | QYKTEAASRYNLTISDVSVSD | (SEQ ID NO:9) |
| Peptide c | 21 amino acids (337-357) | FLQIYKQGGFLGLSNIKFRPG | (SEQ ID NO:10) |
| Peptide d | 21 amino acids (354-374) | FRPGSVVVQLTLAFREGTINV | (SEQ ID NO:11) |
| Peptide e | 19 amino acids (404-422) | VPFPFSAQSGAGVPGWGIA | (SEQ ID NO:12) |

Figure 2A

Muc16 Exemplary Protein – (SEQ ID NO:20)

```
   1  MEHITKIPNE AAHRGTIRPV KGPQTSTSPA SPKGLHTGGT KRMETTTTAL KTTTTALKTT SRATLTTSVY TPTLGTLTPL    AMINO
  81  NASRQMASTI LTEMMITTPY VFPDVPETTS SLATSLGAET STALPRTTPS VLNRESETTA SLVSRSGAER SPVIQTLDVS    TERMINAL
 161  SSEPDTTASW VIHPAETIPT VSKTTPNFFH SELDTVSSTA TSHGADVSSA IPTNISPSEL DALTPLVTIS GTDTSTTFPT    DOMAIN
 241  LTKSPHETET RTTWLTHPAE TSSTIPRTIP NFSHHESDAT PSIATSPGAE TSSAIPIMTV SPGAEDLVTS QVTSSGTDRN
 321  MTIPTLTLSP GEPKTIASLV THPEAQTSSA IPTSTISPAV SRLVTSMVTS LAAKTSTTNR ALTNSPGEPA TTVSLVTHPA
 401  QTSPTVPWTT SIFFHSKSDT TPSMTTSHGA ESSSAVPTPT VSTEVPGVVT STTIPILTLS PGEPETTPSM
 481  ATSHGEEASS AIPTPTVSPG VPGVVTSLVT SSRAVTSTTI PILTFSLGEP ETTPSMATSH GTEAGSAVPT VLPEVPGMVT
 561  SLVASSRAVT STTLPTLTLS PGEPETTPSM ATSHGAEASS TVPTVSPEVP GVVTSLVTSS SGVNSTSIPT LILSPGELET
 641  TPSMATSHGA EASSAVPTPT VSPGVSGVVT PLVTSSRAVT STTIPILTLS SSEPETTPSM ATSHGVEASS AVLTVSPEVP
 721  GMVTSLVTSS RAVTSTTIPT LTISSDEPET TTSLVTHSEA KMISAIPTLA VSPTVQGLVT SLVTSSGSET SAFSNLTVAS
 801  SQPETIDSWV AHPGTEASSV VPTLTVSTGE PFTNISLVTH PAESSSTLPR TTSRFSHSEL DTMPSTVTSP EAESSSAIST
 881  TISPGIPGVL TSLVTSSGRD ISATFPTVPE SPHESEATAS WVTHPAVTST TVPRTTPNYS HSEPDTTPSI ATSPGAEATS
 961  DFPTITVSPD VPDMVTSQVT SSGTDTSITI PTLTLSSGEP ETTTSFITYS ETHTSSAIPT LPVSPGASKM LTSLVISSGT
1041  DSTTTFPTLT ETPYEPETTA IQLIHPAETN TMVPKTTPKF SHSKSDTTLP VAITSPGPEA SSAVSTTTIS PDMSDLVTSL
1121  VPSSGTDTST TFPTLSETPY EPETTVTWLI HPAETSTTVS GTIPNFSHRG SDTAPSMVTS PGVDTRSGVP TTTIPPSIPG
1201  VVTSQVTSSA TDTSTAIPTL TPSPGEPETT ASSATHPGTQ TGFTVPIRTV PSSEPDTMAS WVTHPPQTST PVSRTTSSFS
1281  HSSPDATPVM ATSPRTEASS AVLITTISPGA PEMVTSQITS SGAATSTTVP TLTHSPGMPE TTALLSTHPR TGTSKTFPAS
1361  TVFPQVSETT ASLTIRPGAE TSTALPTQTT SSLFTLLVTG TSRVDLSPTA SPGVSAKTAP LSTHPGTETS TMIPTSTLSL
1441  GLLETTGLLA TSSSAETSTS TLTLTVSPAV SGLSSASITT DKPQTVTSWN TETSPSVTSV GPPEFSRTVT GTTMTLIPSE
1521  MPTPPKTSHG EGVSPTTILR TTMVEATNLA TGGSSPTVAK TTTTFNTLAG SLFTPLTTPG MSTLASESVT SRTSYNHRSW
1601  ISTTSSYNRR YWTPATSTPV TSTFSPGIST SSIPSSTA
                                                AT VPFMVPFFLN FTITNLQYEE DMRHPGSRKF NATERELQGL    TANDEM
1681  LKPLFRNSSL EYLYSGCRLA SLRPEKDSSA MAVDAICTHR PDPEDLGLDR ERLYWELSNL TNGIQELGPY TLDRNSLYVN    REPEAT
1761  GFTHRSSMPT TSTPGTSTVD VGTSGTPSSS PSPTAAGPLL MPFTLNFTIT NLQYEEDMRR TGSRKFNTME SVLQGLLKPL    DOMAIN
1841  FKNTSVGPLY SGCRLTLLRP EKDGAATGVD AICTHRLDPK SPGLNREQLY WELSKLTNDI EELGPYTLDR NSLYVNGFTH
1921  QSSVSTTSTP GTSTVDLRTS GTPSSLSSPT/-/
         IT LLRDIQDKVT TLYKGSQLHD TFRFCLVTNL TMDSVLVTVK ALFSSNLDPS LVEQVFLDKT LNASFHWLGS    CARBOXY
11511 TYQLVDIHVT EMESSVYQPT SSSSTQHFYP NFTITNLPYS QDKAQPGTTN YQRNKRNIED ALNQLFRNSS IKSYFSDCQV    TERMINAL
11591 STFRSVPNRH HTGVDSLICNF SPLARRVDRV AIYEEFLRMT RNGTQLQNFT LDRSSVLVDG YSPNRNEPLT GNSDLPFWAV    DOMAIN
11671 ILIGLAGLLG LITCLICGVL VTTRRRKKEG EYNVQQQCPG YYQSHLDDED LQ
```

Figure 2B

Muc16 juxtamembrane domain-GST Fusion

GST plus amino acids 11559-11666 of Muc16

GST-TN YQRNKRNIED ALNQLFRNSS IKSYFSDCQV STFRSVPNRH HTGVDSLCNF SPLARRVDRV AIYEEFLRMT
RNGTQLQNFT LDRSSVLVDG YSPNRNEPLT GNSDLP (SEQ ID NO:13)

Synthetic Peptides

| | | | |
|---|---|---|---|
| Peptide a | 20 amino acids | (11644-11663) | SSVLVDG YSPNRNEPLT GNS | (SEQ ID NO:14) |
| Peptide b | 20 amino acids | (11559-11578) | TN YQRNKRNIED ALNQLFRN | (SEQ ID NO:15) |
| Peptide c | 21 amino acids | (11576-11596) | FRNSS IKSYFSDCQV STFRSV | (SEQ ID NO:16) |
| Peptide d | 23 amino acids | (11595-11617) | SVPNRH HTGVDSLCNF SPLARRV | (SEQ ID NO:17) |
| Peptide e | 28 amino acids | (11618-11645) | DRV AIYEEFLRMT RNGTQLQNFT LDRSS | (SEQ ID NO:18) |

Figure 4A
Clone 2C12
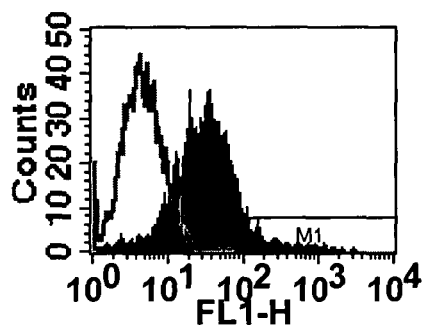
Clone 10B7
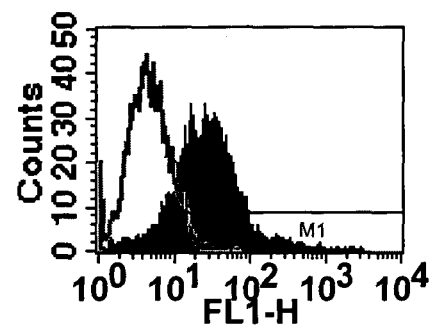
Clone 4H2
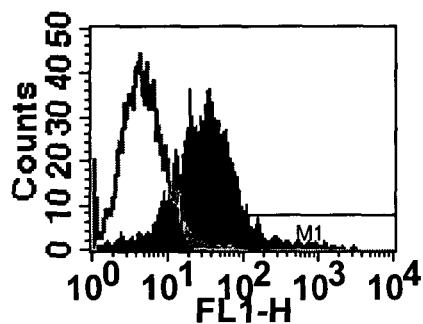
Clone 6H6
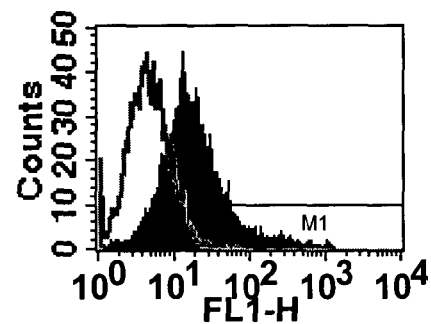
Clone 9B9
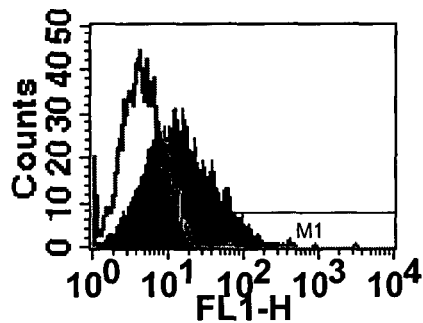
Clone 8H1
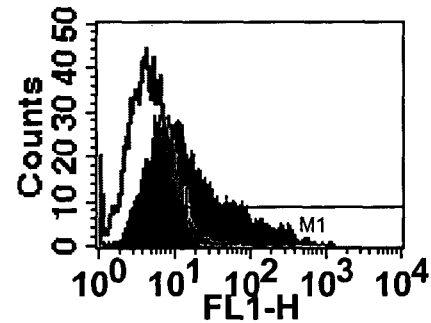

Figure 4A (continued)
Clone 6A4
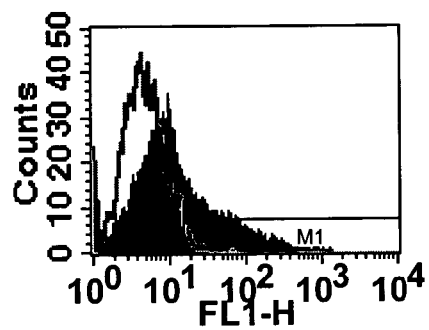
Clone 7C10
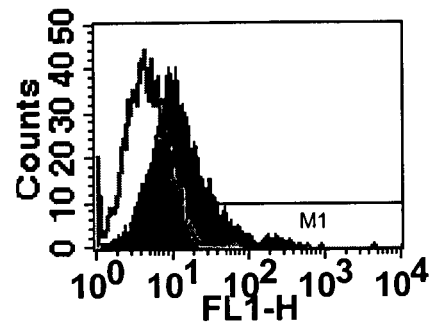
Clone 6C7
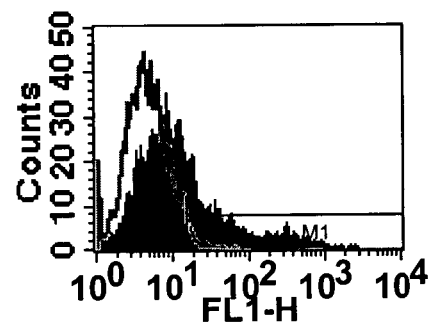
Clone 2A10
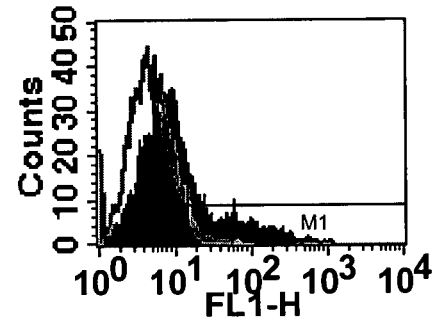
Clone 3A3
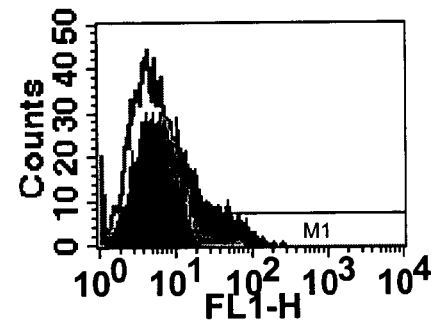
Clone 5C11
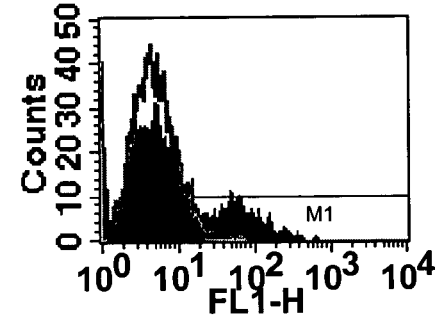

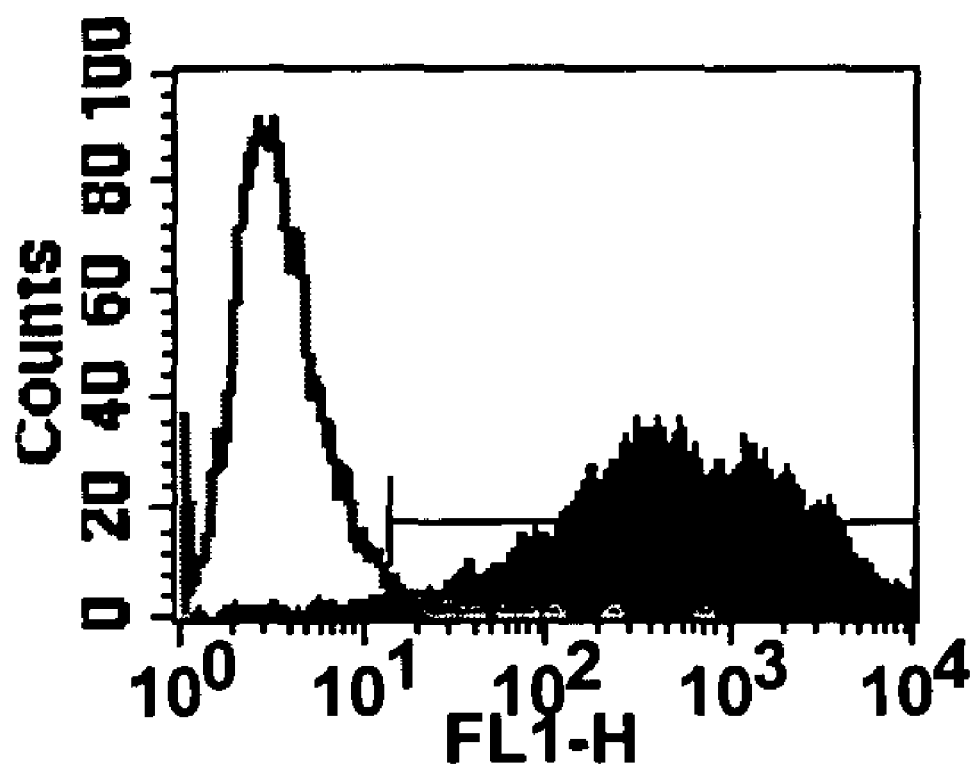

Figure 5A
Clone 1B8
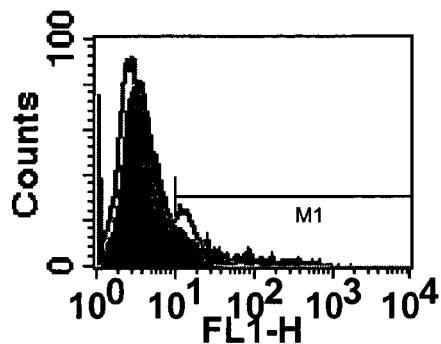
Clone 1D2
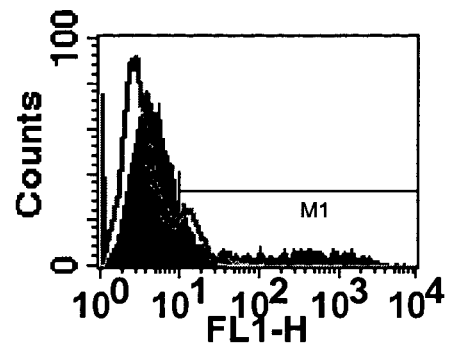
Clone 2F4
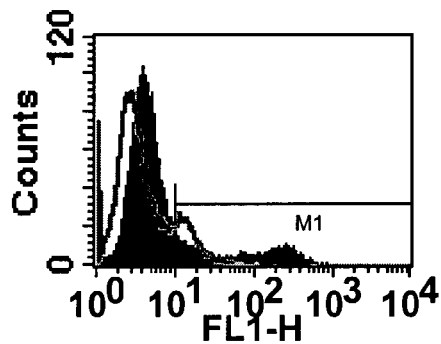
Clone 3B9
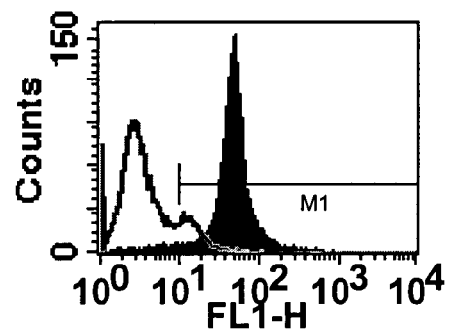
Clone 4E2
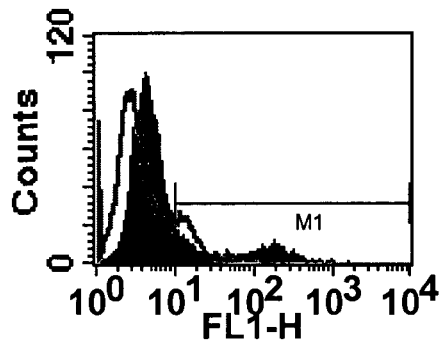
Clone 4F8
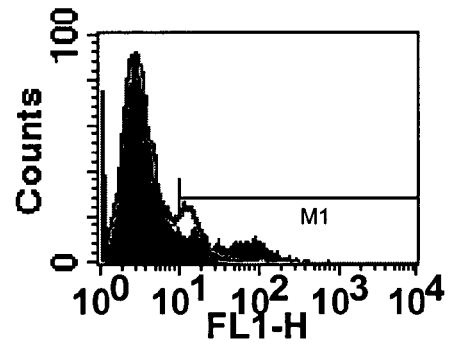

Figure 5A (continued)
Clone 5G1
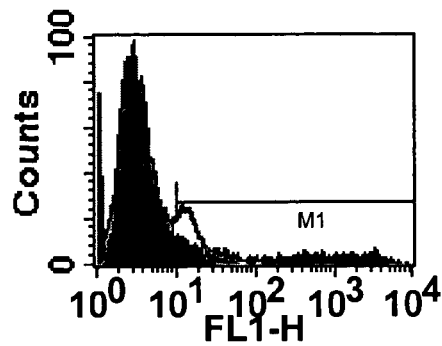
Clone 5G8
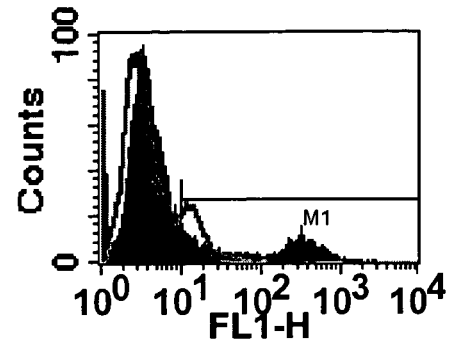
Clone 9E2
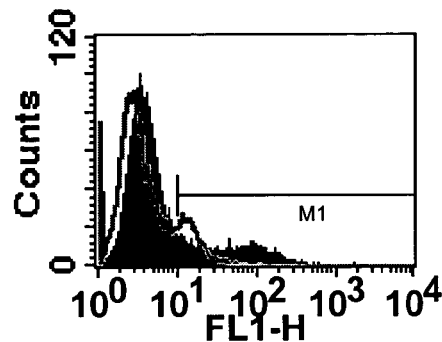
Clone 9G10
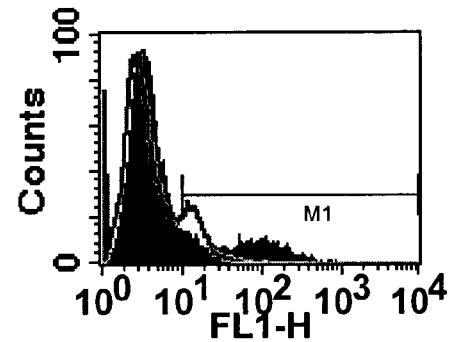
Clone 10C3
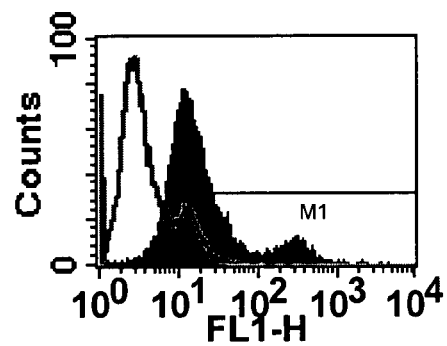
Clone 10G2
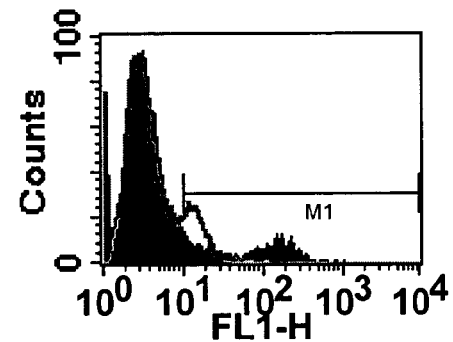

Figure 5A (continued)
Clone 2A9
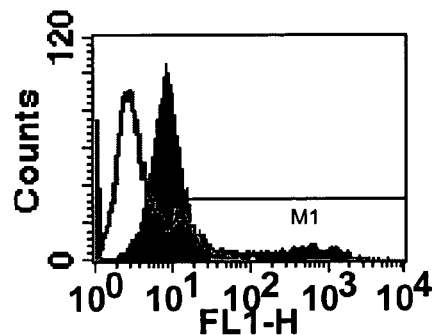
Clone 2E6
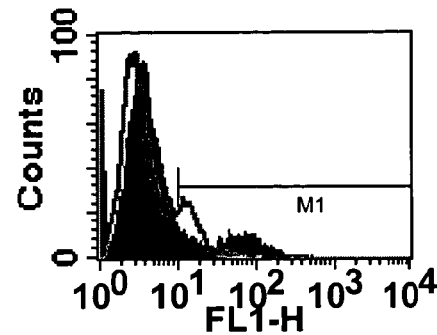
Clone 2F9
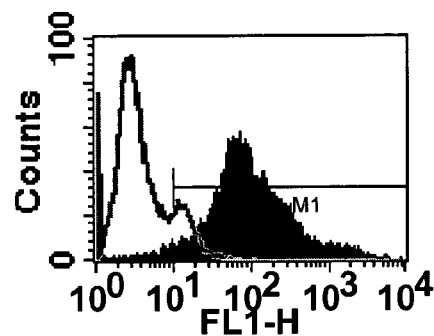
Clone 3C2
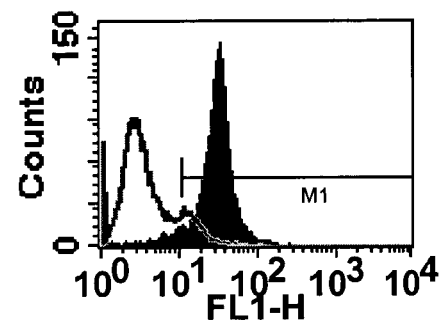
Clone 3E7
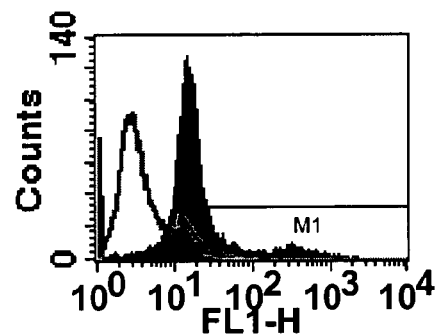
Clone 5C5
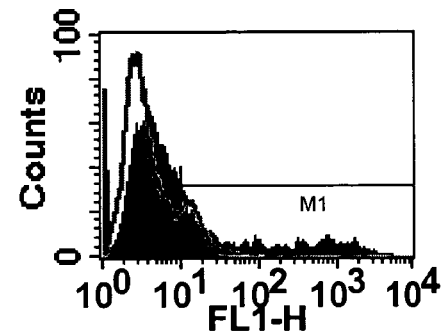

Figure 5A (continued)
Clone 5E11
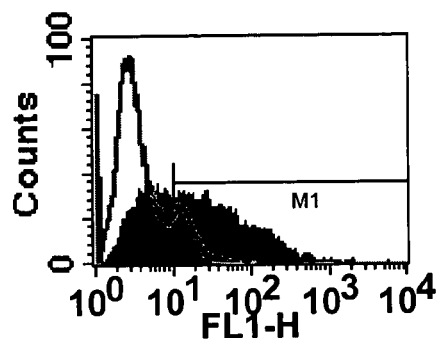
Clone 7G7
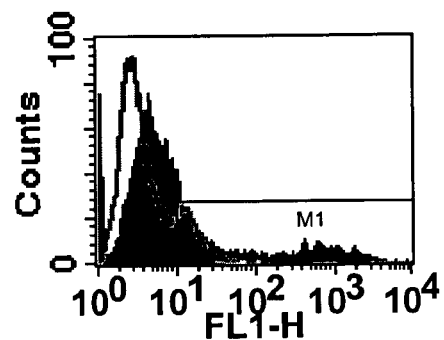
Clone 9D8
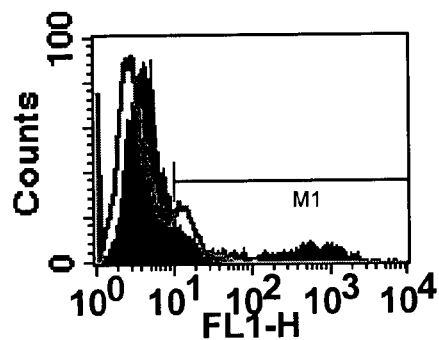
Clone 10C9
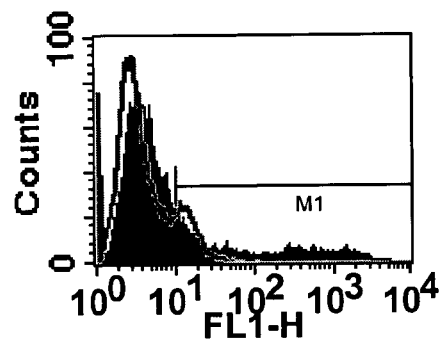
Clone 2D3
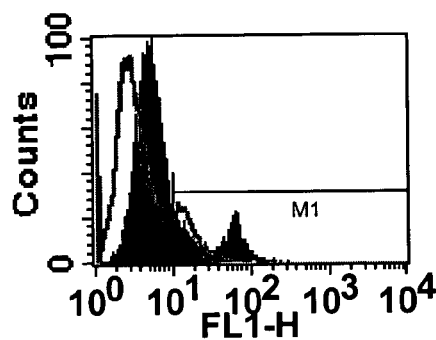
Clone 9G4
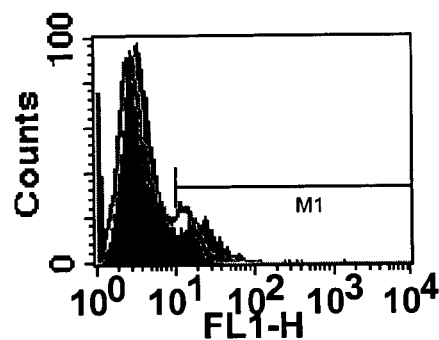

M11

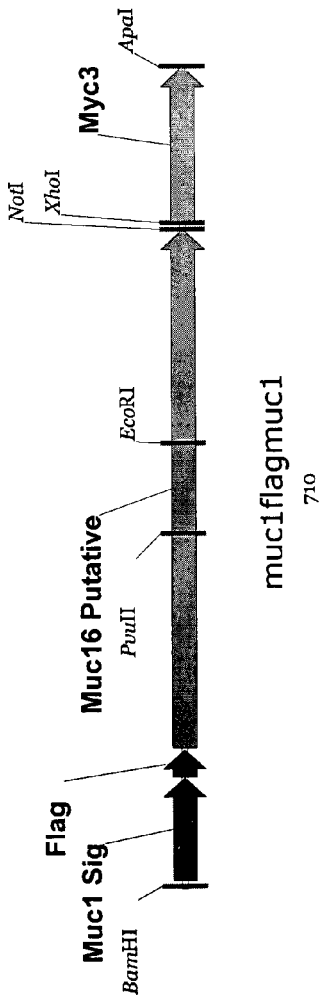

Figure 6A

Figure 6B (SEQ ID NO:21)

```
       BamHI
       ------
  1   GGATCCATGA CACCGGGCAC CCAGTCTCCT TTCTTCCTGC TGCTGCTCCT CACAGTGCTT ACAGTTGTTA CAGGTTCTGG TCATGCAAGC TCTATGCGACT ACAAGGACGA
       CCTAGGTACT GTGGCCCGTG GGTCAGAGGA AAGAAGGACG ACGACGAGGA ACGTCAACAT GTCAAGACC AGTACGTTCG AGATGCTGA TGTTCCTGCT
       XbaI
       ------
 111  CGATGACAAG TCTAGATTCC GAAACAGGAG CATCAAGAGT TATTTTTCTG ACTGTCAAGT TTCAACATTC AGGTCTGTCC CCAACAGGCA CCACACCGGG GTGGACTCCC
       GCTACTGTTC AGATCTAAGG CTTTGTCGTC GTAGTTCTCA ATAAAAAGAC TGACAGTTCA AAGTTGTAAG TCCAGACAGG GGTTGTCCGT GGTGTGGCCC CACCTGAGGG
                                                                                                             KpnI
                                                                                                             ------
 221  TGTGTAACTT CTCGCCACTG GCTCGGAGAG TAGACAGAGT TGCCATCTAT GAGGAATTTC TGCGGATGAC CCGGAATGGT ACCCAGCTGC AGAACTTCAC CCTGGACAGG
       ACACATTGAA GAGCGGTGAC CGAGCCTCTC ATCTGTCTCA ACGGTAGATA CTCCTTAAAG ACGCCTACTG GGCCTTACCA TGGGTCGACG TCTTGAAGTG GGACCTGTCC
                                                                              EcoRI
                                                                              ------
 331  AGCAGTGTCC TTGTGGATGG GTATTCTCCC AACAGAAATG AGCCCTTAAC TGGGAATTCT GACCTTCCCT TCTGGGCTGT CATCCTCATC GGCTTGCGAG GACTCCTGGG
       TCGTCACAGG AACACCTACC CATAAGAGGG TTGTCTTTAC TCGGGAATTG ACCCTTAAGA CTGGAAGGGA AGACCCGACA GTAGGAGTAG CCGAACGTC CTGAGGACCC
 441  ACTCATCACA TGCCTGATCT GCGGTGTCCT GGTGACCACC CGCCACAGGA CGCACTGGTG GCCGGCCGCA CCACTGGTGG GCCGCCGCCT TCTTCCTTCC CAGGTCGTTG CAGGTCGTTG TCACGGGTCC GATGATGGTC AGTGTGGATC
       TGAGTAGTGT ACGGACTAGA CGCACAGGA GCCACTGGTG GCCGGCCGCA CCACTGGTGG GCCGCCGCCT
                    XhoI
                    ------
             NotI
             ------
 551  ACCTGGAGGA TCTGCAAGCG GCCGCTCGAG GCCGCCATGA CCACCATGGA CAAAAACTC ATCTCAGAAG AGGATCTGGC TAGCGAACAA AAACTCATCT CAGAGAGGA TCTGGAACAA
       TGGACCTCCT AGACGTTCGC CGGCGAGCTC CGGCGGTACT GGTGGTACCT TGTTTTTGAG TAGAGTCTTC TCCTAGACCG ATCGCTTGTT TTTGAGTAGA GTCTTCTCCT AGACCTTGTT
                                                      XbaI                                     ApaI
                                                      ------                                   ------
 661  AAACTCATCT CAGAAGAGGA TCTGACCGGT TAAATGCATC TAGAGGGCCC
       TTTGAGTAGA GTCTTCTCCT AGACTGGCCA ATTTACGTAG ATCTCCCGGG
```

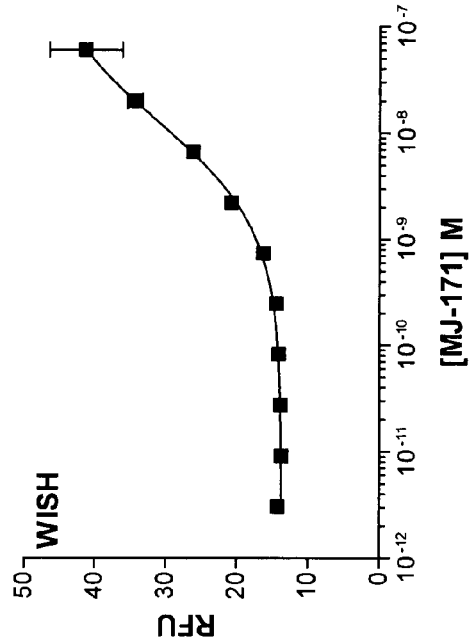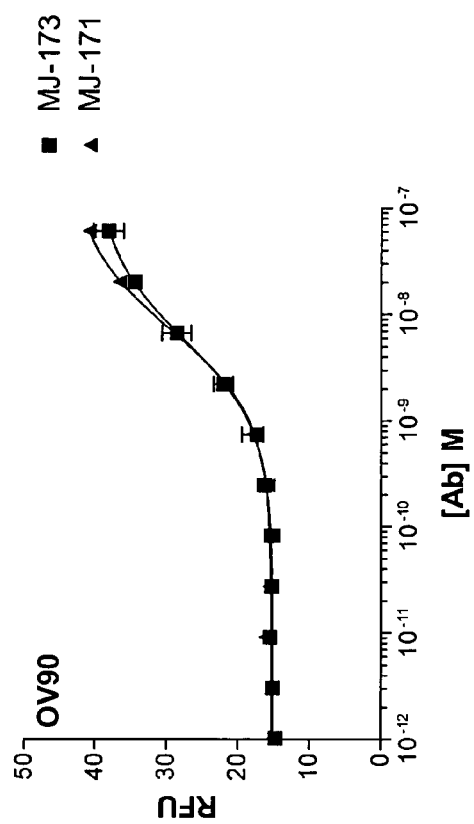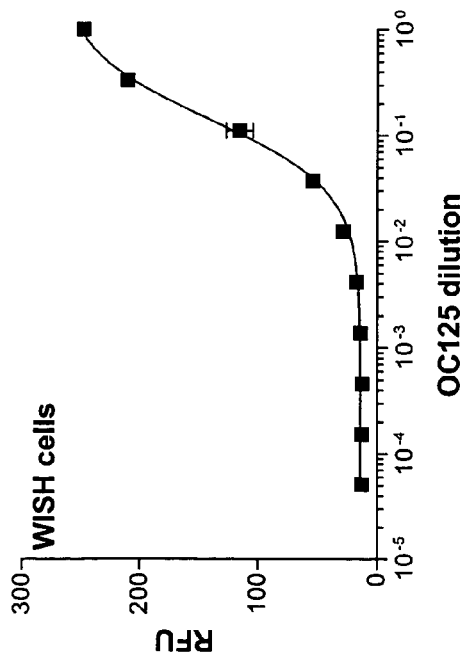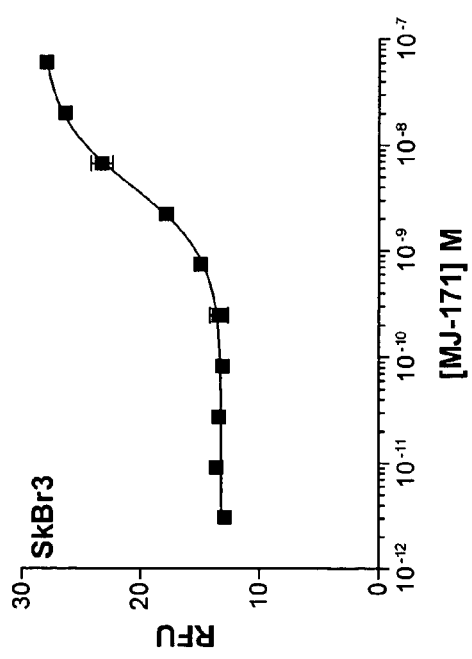
Figure 12A
Figure 12B
Figure 12C
Figure 12D

ANTIBODIES TO NON-SHED MUC1 AND MUC16, AND USES THEREOF

This application claims benefit of Provisional Application No. 60/393,094, filed Jul. 3, 2002; the disclosure of which is incorporated herein by reference.

FIELD OF THE INVENTION

The present invention relates to antibodies directed to plasma membrane epitopes. Specifically, the invention relates to antibodies, hybridomas producing said antibodies, and antibody-containing compositions and uses thereof, wherein said antibodies recognize epitopes on the extracellular portions of proteins that are retained on the plasma membrane and are substantially not shed into the extracellular medium. The invention further relates to uses of such antibodies and antibody-containing compositions in the detection, treatment and monitoring of cancers, such as ovarian and breast cancer, in which Muc1 and/or Muc16 protein levels are altered.

BACKGROUND OF THE INVENTION

Cell surface antigens are often shed from a cell by proteolytic cleavage. The resulting fragments are found circulating in the blood. While circulating shed antigen is often useful for monitoring disease state, it can have a negative impact on the outcome of immunotherapy. For this reason, antibodies that target an extracellular juxtamembrane region of a plasma membrane protein which remains cell-associated following shedding are ideal for immunotherapeutic approaches.

Muc1 (episialin, polymorphic epithelial mucin, PEM, PUM, MAM-6, PAS-O, EMA, NPG, DF-3) and Muc16 (CA-125) are plasma membrane mucins that are upregulated in a variety of malignancies (Jacobs and Bast, 1989; Taylor-Papadimitriou et al., 1999). Both Muc1 and Muc16 are type I membrane proteins comprising: (a) a short cytoplasmic domain (69 amino acids for Muc1, 31 amino acids for Muc16), which interacts with the intracellular signal transduction machinery (Li et al., 1998; Li and Kufe, 2001; Li et al., 2001; Li et al., 2001; Fendrick et al., 1997; Konishi et al., 1994)); (b) a transmembrane domain; and (c) a large, heavily glycosylated extracellular domain. The extracellular domain of both proteins comprises a large region of tandem repeats, with 20 amino acid long tandem repeats for Muc1 and 156 amino acid long tandem repeats for Muc16. Muc1 has a variable number of tandem repeats (from 25 to 100, depending upon the allele) (Devine and McKenzie, 1992; O'Brien et al., 2001; O'Brien et al., 1998; Taylor-Papadimitriou et al., 1999). To date, there is no evidence supporting genetic polymorphism of Muc16. The resulting peptide cores of Muc1 and Muc16 have molecular weights of approximately 125–200 kDa and 2.5 MDa, respectively (O'Brien, 2002).

Muc1 is expressed on the surface of epithelial cells as a heterodimer derived from a common precursor (Ligtenberg et al., 1992; Parry et al., 2001). Proteolytic processing may occur cotranslationally in the endoplasmic reticulum by a kallikrein-like protease (Parry et al., 2001). The extracellular subunit remains non-covalently associated with the subunit containing the transmembrane region and cytoplasmic tail throughout intracellular processing and transport to the cell surface. It is not yet known whether Muc16 is proteolytically processed in a similar manner. However, Muc16 has a conserved furin cleavage site (RXK/RR) in the extracellular domain approximately 100 amino acids away from the transmembrane domain (Bassi et al., 2000; Molloy et al., 1999; O'Brien et al., 2001). Furins are implicated in trans-golgi network proteolytic processing of a number of proteins including cell-surface receptors (Molloy et al., 1999).

Both Muc1 and Muc16 may be used as serum markers for diagnosis and for monitoring the progress of treatment of malignancies. Thus, breast tumors may be diagnosed and the progress of treatment monitored using Muc1 antibody assays (Bon et al., 1997), while anti-Muc16 antibodies such as OC125 and M-11 may be used in cases of ovarian cancer (Cannistra, 1993). The mechanism of shedding (i.e. the release of these mucins or their fragments into the blood or other extracellular fluid) is not fully known. In the case of Muc16 shedding may be regulated by serine/threonine phosphorylation of the cytoplasmic domain of Muc16 in response to EGF stimulation (O'Brien et al., 1998). Although Muc1 is also phosphorylated in response to EGF stimulation, there is currently no evidence for a role of such phosphorylation in the mechanism of shedding of portions of Muc1. It is also unclear whether the shed portion of Muc1 corresponds to the extracellular subunit that is produced by the cleavage of the Muc1 protein in the endoplasmic reticulum, or whether there is an additional cleavage site that is targeted by a stromal protease. Less information is currently available regarding the processing and shedding of Muc16. Sequence information indicates that Muc16, in addition to the potential furin cleavage site, has a potential stromolysin cleavage site (SPLA) located about 50 amino acids upstream from the transmembrane domain, cleavage of which could release the fragment of CA125 that is bound by monoclonal antibodies OC125 and M-11.

Tumor-cell specific monoclonal antibodies conjugated to highly toxic maytansinoid drugs and prodrugs have been shown to be effective in the treatment of tumors in mouse models (Liu et al., 1996). The Muc1 and Muc16 proteins represent attractive sources of epitopes for the development of such antibody-containing conjugates, such as may be termed tumor-activated prodrugs (TAPs), because expression of these epitopes is frequently elevated in tumors (see above).

However, a portion of the total Muc1 or Muc16 expressed by tumor cells is shed into the blood stream as evidenced by the ability to use Muc1 and Muc16 antibodies for monitoring disease state (see above). Clinical trials with naked and drug-conjugated monoclonal antibodies to various target antigens suggest that high concentrations of circulating antigen present in some patients is problematic. (Baselga et al., 1996; Pegram et al., 1998; Tolcher et al., 2001). A high concentration of circulating antigen greatly increases the antibody clearance-rate, resulting in low delivery of the antibody to the tumor. Furthermore, in the case of drug-conjugated antibodies recognizing shed antigen, the increased rate of clearance may result in dose-limiting toxicity in the liver. Although some patients may exhibit relatively low levels of shed antigen, the tandem repeat nature of mucins, such as Muc1 and Muc16, resulting in potentially many epitopes per molecule, make the absolute quantification of shed epitope difficult to accomplish. Thus, with currently available Muc1 and Muc16 antibodies to shed portions of these molecules, patients cannot be reliably evaluated for whether their shed antigen level is prohibitively high for antibody therapy. Therefore, there is a need for antibodies that are specific for epitopes contained in the non-shed portions of Muc1 or Muc16, so that cytotoxic drug conjugates of such antibodies may be efficiently directed to tumor cells even in the presence of high concentrations of circulating shed fragments of Muc1 and Muc16. To date, no antibodies defined as reacting with non-shed, extracellular domains of shed proteins have been reported.

The present inventors have developed antibodies, antibody fragments and conjugates of such antibodies or fragments, methods for preparing and screening such antibodies, diagnostic screening methods and treatment methods using such antibodies and conjugates, which address the above-mentioned shortcomings and problems identified in the prior art. The many advantages of the present invention will become apparent to those of ordinary skill in the art upon reading the following disclosure.

SUMMARY OF THE INVENTION

The inventors of the present invention have found that antibodies directed to epitopes located on non-shed extracellular portions of shed antigens have improved properties for the detection, monitoring and treatment of certain malignancies.

In a first aspect, the present invention is directed to an isolated monoclonal antibody capable of binding to an epitope of a non-shed extracellular portion of a shed antigen and to a hybridoma capable of producing the antibody. This embodiment is not limited to intact antibodies, but encompasses antibody fragments and recombinant fusion proteins comprising an antibody fragment. Nor is the means of antibody production particularly limited, and encompasses, in addition to immunization of animals and the production of hybridomas, the screening of recombinant antibody fragments, for example by the panning of a phage display library of antibody or antibody fragments. In addition, the invention encompasses immunization of an animal with a recombinant fusion protein comprising an extracellular non-shed portion of the shed antigen, or immunization of an animal with a cell expressing a recombinant non-shed extracellular domain of the shed antigen.

The antibodies of this embodiment are directed to epitopes that are located on non-shed extracellular portions of shed antigens. In an exemplary embodiment, the shed antigen is human Muc1 or Muc16. Preferably, at least a part of said Muc1 epitope is located within the last 90 amino acids of the Muc1 extracellular domain, therefore at the carboxy terminus of the Muc1 extracellular domain, and the Muc16 epitope is located within the last 110 amino acids of the Muc16 extracellular domain, therefore at the carboxy terminus of the Muc16 extracellular domain.

Thus, the preferred epitope for Muc1 is located at least in part within the following amino acid sequence:

```
                                                  (SEQ ID NO:1)
FLQIYKQGGFLGLSNIKFRPGSVVVQLTLAFREGTINVHDVETQFNQYKT

EAASRYNLTISDVSVSDVPFPFSAQSGAGVPGWGIA
``` and the preferred epitope for Muc16 is located at least in part within the following amino acid sequence:

```
                                                  (SEQ ID NO:2)
TNYQRNKRNIEDALNQLFRNSSIKSYFSDCQVSTFRSVPNRHHTGVDSLC

NFSPLARRVDRVAIYEEFLRMTRNGTQLQNFTLDRSSVLVDGYSPNRNEP

LTGNSDLP.
```

However, this embodiment is not limited to only antibodies recognizing epitopes located at least in part within the sequences given by SEQ ID NO:1 or SEQ ID NO:2, but also encompasses antibodies directed to all epitopes located on non-shed extracellular portions of human Muc1 or Muc16 proteins. Therefore, the present embodiment also encompasses antibodies or antibody fragments directed to epitopes that can include polymorphisms, either presently known or yet to be discovered, of the non-shed extracellular portions of the shed antigens.

In a second aspect, the present invention is directed to conjugates comprising the antibody of the present invention covalently attached to a cytotoxic agent or a prodrug of a cytotoxic agent. In preferred embodiments, the cytotoxic agent is a maytansinoid, an analog of a maytansinoid, a prodrug of a maytansinoid, or a prodrug of an analog of a maytansinoid. Such conjugates are useful as tumor-cell specific therapeutic agents (see, U.S. Pat. Nos. 6,333,410; 5,475,092; 5,585,499; and 5,846,545). In addition a preferred cytotoxic drug may be a taxane or a CC-1065 analog (see U.S. Pat. Nos. 6,340,701 & 6,372,738 for taxanes and 5,846,545; 5,585,499 & 5,475,092 for CC-1065 analogs).

In a third aspect, the present invention provides a composition comprising an antibody capable of binding to an epitope of a non-shed extracellular portion of a shed antigen, or a conjugate of said antibody, including conjugates of antibody fragments, and a pharmaceutically acceptable carrier.

In a fourth aspect, the present invention provides a method of treating a subject in need of treatment, such as a subject having a malignancy in which a shed antigen, such as human Muc1 or Muc16 is elevated, by administering an effective amount of the pharmaceutical composition of the second or third aspect of the present invention. In preferred embodiments, the treatment is directed to a subject having ovarian cancer or breast cancer.

In a fifth aspect, the present invention provides for the screening of a subject for a condition in which shed antigen levels are elevated. In this aspect, the antibodies of the present invention can be used in any immunological technique, either presently known or yet to be developed, to measure shed antigen levels in a subject suspected of having said condition. By comparing the amount of shed antigen in a tissue sample from the subject, by using antibodies that bind to the non-shed extracellular portion of the shed antigen, with the amount in a suitable control sample, or known baseline level, the subject is screened for a condition in which the shed antigen levels are elevated.

Finally, in a sixth aspect, the present invention provides a method of screening for the antibody of the present invention from a library of antibodies or antibody fragments. In this aspect, the antibody or fragment is identified by (1) its recognition of an epitope of a non-shed extracellular portion of a shed antigen, for example, by the use of cells derived from tissue culture or tumor specimens expressing Muc1 and/or Muc16, and (2) its non-recognition of human Muc1 or Muc16 proteins shed into an extracellular medium such as a tissue culture medium or the blood of a cancer patient. By this method, applied in any order, antibodies directed to epitopes located on non-shed extracellular portions of shed proteins, such as human Muc1 or Muc16, are identified.

BRIEF DESCRIPTION OF THE DRAWINGS

FIG. 1A shows the amino acid sequence and features of an exemplary Muc1 protein (SEQ ID NO:19) (GENBANK Accession Nos. NM_002456) having one VNTR tandem repeat (underlined), with the putative signal peptide cleavage sites and post-translational cleavage site as indicated by arrows, and the transmembrane region as indicated with the double underscore.

FIG. 1B shows the amino acid sequence of an exemplary Muc1 juxtamembrane domain GST fusion protein and synthetic peptides derived from amino acids contained within the fusion protein.

FIG. 2A shows the amino acid sequence and features of an exemplary Muc16 GST-fusion protein (SEQ ID NO:20) (AF414442; O'Brien et al. (2000) Tumor Biology 22, 348–366). RNKR is a potential furin site, SPLA is a potential stromolysin cleavage site, and the transmembrane region is double underscored.

FIG. 2B shows the amino acid sequence of an exemplary Muc16 juxtamembrane domain GST fusion protein and synthetic peptides derived from amino acids contained within the fusion protein.

FIGS. 4A & 4B show flow cytometry histograms of selected clones from the Muc1 Peptide a hybridoma supernatant screen. Binding to the Muc1 antigen positive cell line, CaOV3, was measured using 30 µl of hybridoma supernatant. FIG. 4A: Histograms of the 12 clones selected for further study. FIG. 4B: Histogram of purified CM1 monoclonal antibody binding to CaOV3 cells at $1 \times 10^{-7}$ M concentration. CM1 recognizes a Muc1 epitope within the shed VNTR domain.

FIGS. 5A & 5B show flow cytometry histograms of selected clones from the Muc16 Peptide a hybridoma supernatant screen. Binding to the Muc16 antigen positive cell line OVCAR3 was measured using 30 µl of hybridoma supernatant. FIG. 5A: Histograms of the 24 clones selected for further study. FIG. 5B: Histogram of purified M11 binding to OVCAR3 cells at $6.7 \times 10^{-8}$ M concentration.

FIG. 6 shows a map and sequence (SEQ ID NO:21) of the Muc16 Stump plasmid construct. The nucleotide sequence of the Muc16 Putative Stump encodes amino acids 11576–11722 shown in FIG. 2A.

FIG. 12 shows flow cytometric analysis of anti-Muc16 antibodies binding to tumor cell lines. The binding curves represent the average relative fluorescence of gated populations of cells as indicated in Table 4. Various concentrations of the purified Muc16 antibodies were incubated with the indicated tumor cell lines for approximately 3 hours on ice. Antibody binding was detected by FITC-labeled goat anti-mouse IgG and analyzed on a Becton Dickinson FACSCalibur flow cytometer. FIG. 12A: Binding of commercially available OC125 to WISH Cells. Because the purity of OC125 was not known serial dilutions rather than concentrations were used. FIG. 12B: Binding of MJ-171 to WISH cells. FIG. 12C: Binding of MJ-171 to SkBr3 cells. FIG. 12D: Binding of MJ-173 and MJ-171 to OV90 cells.

FIG. 13A: Flow cytometric analysis of the purified anti-Muc1 MJ-170 antibody binding to the CaOV3 ovarian tumor cell line. Various concentrations of purified MJ-170 were incubated with CaOV3 cells for approximately 3 hours on ice. Antibody binding was detected by FITC-labeled goat anti-mouse IgG and analyzed on a Becton Dickinson FACSCalibur flow cytometer. FIG. 13B: Flow cytometric analysis of CM1, an antibody recognizing the Muc1 VNTR domain, binding to CaOV3 cells. The binding curves represent the average relative fluorescence of a gated population of cells (approximately 5% of total).

FIG. 14 shows the cytotoxicity of an MJ-171-DM1 conjugate to various tumor cell lines. Cells were plated in 96-well plates at a density of 2000 cells per well. Various concentrations of the MJ-171-DM1 conjugate were added and the cells incubated at 37° C./5% $CO_2$ for 5 days. MTT was added and incubation continued for 3.5 hours. Culture supernatant was carefully removed, the MTT-formazan complexes solubilized in DMSO, and the absorption at 540 nm measured using a platereader.

DETAILED DESCRIPTION OF THE INVENTION

Figure 3:
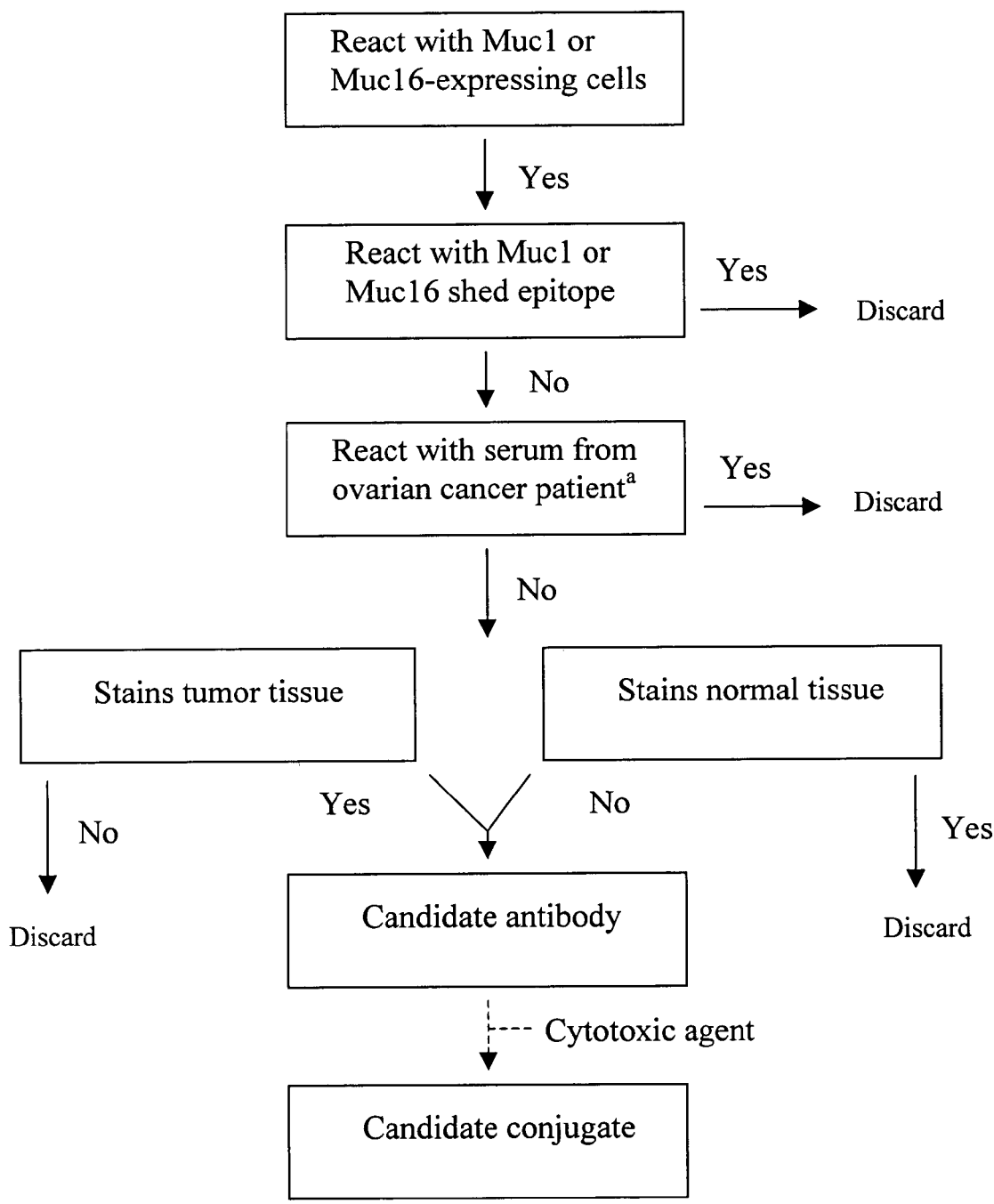
FIG. 3 shows a flowchart for the screening of antibodies as candidate cancer therapeutic agents, which may optionally be used to prepare candidate anticancer therapeutic conjugates (broken lines).

The present invention is described by reference to the shed antigens, Muc1 and Muc16. However, the invention should not be considered limited thereto.

The present invention provides monoclonal antibodies that bind specifically to a non-shed extracellular domain of a shed antigen, such as Muc1 and Muc16, and uses thereof.

Prior to setting forth the invention in detail, it may be helpful to the understanding thereof to define the following terms:

The term "monoclonal antibody" as used herein refers to a substantially homogeneous population of antibodies, i.e., the individual antibodies comprising the population are identical in specificity and affinity except for possible naturally occurring mutations that may be present in minor amounts. Note that a monoclonal antibody composition may contain more than one monoclonal antibody. Thus, the modifier "monoclonal" indicates the character of the antibody as a substantially homogeneous population of antibodies, and is not to be construed as requiring production of the antibody by any particular method.

A "non-shed extracellular portion" of an antigen, such as Muc1 or Muc16, is herein defined as an extracellular portion of the antigen that is substantially not released into the extracellular medium or blood.

The term "juxtamembrane" as used herein represents that portion of the amino acid sequence of a shed antigen, such as Muc1 or Muc16, that is approximately bounded by the transmembrane domain (see FIGS. 1A and 2A, double underscored domains) and the shed portion of the protein. Therefore, the juxtamembrane portions of shed antigens correspond to their non-shed extracellular portions.

A "conjugate" as used herein represents the antibody of the present invention covalently linked to a cytotoxic agent.

The covalent linkage can include cleavable linkages such as disulfide bonds, which may advantageously result in cleavage of the covalent linkage within the reducing environment of the target cell.

A "prodrug" as used herein represents an analog of a cytotoxic agent that substantially lacks cytotoxic activity until subjected to an activation step. Activation steps may include enzymatic cleavage, a chemical activation step such as exposure to a reductant, or a physical activation step such as photolysis.

A "cytotoxic agent" as used herein is any agent that is capable of inhibiting the growth of a target cell or of killing a target cell.

An "expression vector" denotes a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, and the like. Expression vectors are generally derived from plasmid or viral DNA, or may contain elements of both.

Where parts of an amino acid sequence of a protein are referred to by number, it is to be understood that the numbering proceeds from the N-terminus of the sequence unless otherwise noted.

The monoclonal antibodies of the present invention can be raised against the extracellular juxtamembrane portion of a shed antigen using synthetic or recombinant peptides. Any method for generating monoclonal antibodies, for example by in vitro generation with phage display technology and in vivo generation by immunizing animals, such as mice, can be used in the present invention. These methods include the immunological method described by Kohler and Milstein in Nature 256, 495–497 (1975) and Campbell in "Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1985); as well as by the recombinant DNA method described by Huse et al in Science 246, 1275–1281 (1989). Standard recombinant DNA techniques are described in Sambrook et al., "Molecular Cloning," Second Edition, Cold Spring Harbor Laboratory Press (1987) and by Ausubel et al. (Eds) "Current Protocols in Molecular Biology," Green Publishing Associates/Wiley-Interscience, New York (1990).

The juxtamembrane regions of shed antigens can be determined experimentally by routine methods. The cleavage site of shed type I and type II membrane protein antigens can be identified using recombinant, epitope-tagged cDNAs of the antigen in question in a modification of the procedure used by Parry et al. to identify the Muc1 endoplasmic reticulum processing cleavage sites (Parry, S., Silverman, H. S., McDermott, K., Willis, A., Hollingsworth, M. A., and Harris, A. (2001) Identification of MUC1 proteolytic cleavage sites in vivo. Biochem Biophys Res Commun 283, 715–20). In the case of Type I membrane antigens, the epitope-tag is inserted at the C-terminus (non-shed fragment). The recombinant antigen is then expressed either transiently or stably in an appropriate cell line. Epitope-tagged antigen is purified from cell lysate and subjected to N-terminal sequencing. The resulting sequence information will consist of the N-termini of the full-length and the cleaved epitope-tagged, cell-associated antigen. The N-terminus of the cleaved antigen defines the boundary of the "juxtamembrane" region. For Type II membrane antigens, the epitope-tag is inserted at the N-terminus (non-shed fragment). Epitope-tagged material is purified from cell lysate and subjected to mass spectrometry to determine the molecular weight of the cell associated fragment. The cleavage site is extrapolated from the molecular weight of the cell-associated fragment, again allowing one to deduce the boundary of the "juxtamembrane" region of the cell-associated cleaved antigen.

Alternatively, monoclonal or polyclonal antibodies directed against the intracellular domain of the antigen in question may be used to purify endogenous cell-associated antigen for N-terminal sequencing in the case of Type I membrane proteins or for mass spectrometry in the case of Type II membrane proteins.

For in vivo immunization, the peptides are preferably conjugated to an immunogenic protein carrier, such as a keyhole limpet hemocyanin (KLH) or are prepared and used as recombinant glutathione-S-transferase (GST) fusion proteins. Thus, peptides may be used by themselves as immunogens, or may be attached to a carrier protein or to other objects, such as beads, e.g. sepharose beads. After the immunized mammal has produced antibodies, a mixture of antibody-producing cells, such as the splenocytes, is isolated. Monoclonal antibodies may be produced by isolating individual antibody-producing cells from the mixture and making the cells immortal by, for example, fusing them with tumor cells, such as myeloma cells. Preferred myeloma cells are those that fuse efficiently, support stable high level expression of antibody by the selected antibody-producing cells, and are sensitive to a medium such as a HAT medium. Among these preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Manassas, Va. USA, or P3X63Ag8U.1 murine myeloma cells (Yelton et al., Curr. Top. Microbiol. Immunol. 81, 1 (1978)). Human myeloma and mouse-human heteromyeloma cell lines also have been described for the production of human monoclonal antibodies (Kozbor, J. Immunol. 133:3001 (1984)). The resulting hybridomas are preserved in culture and express monoclonal antibodies, which are harvested from the culture medium. The antibody may be prepared in any mammal, including mice, rats, rabbits, goats and humans. The antibody may be a member of one of the following immunoglobulin classes: IgG, IgM, IgA, IgD, or IgE, and the subclasses thereof, and is preferably an IgG1 antibody. The monoclonal antibodies secreted by subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The antigen used for the preparation of the anti Muc1 and Muc16 antibodies of the present invention is a peptide antigen derived from the juxtamembrane extracellular non-shed portion of a Muc1 or Muc16 protein (FIGS. 1A and 2A). Muc1 and Muc16 proteins are polymorphic, particularly with respect to the number of tandem repeats of the VNTR regions. Such polymorphisms, both presently known and those Muc1 and Muc16 polymorphisms yet to be identified, are expressly within the scope of the present invention. Thus, polymorphic forms of Muc1 are known that differ in the number of VNTR repeats and in the sequence adjacent to these repeats. For example, GENBANK Admission No. J05582 is a human Muc1 protein having 40 tandem repeats of VNTR sequence:

PDTRPAPGSTAPPAHGVTSA         (SEQ ID NO:3)

while GENBANK Admission No. NM_002456 is a human Muc1 protein having only a single copy this VNTR sequence. However, the juxtamembrane sequence is conserved between these exemplary sequences.

Referring now to FIG. 1A, an exemplary Muc1 sequence (SEQ ID NO:19) is shown (GENBANK Accession Nos. NM_002456) having one VNTR tandem repeat (underlined) and a transmembrane domain (double underscored domains). The extracellular domain consists of amino acids 24–422 and the intracellular domain consists of amino acids 447–515. The sites of cleavage (N-terminal signal peptide cleavage at amino acids 23 or 27 and post-translational cleavage site at amino acid 357) likely occurring in the endoplasmic reticulum before translocation to the surface are shown. The post-translational cleavage site may delineate the shed portion or alternatively, a second cleavage event either N-terminal or C-terminal to the post-translational cleavage site may cause release of the shed antigen.

In FIG. 1B are shown a Muc1 juxtamembrane domain-GST fusion (SEQ ID NO:7) and synthetic peptides (peptides a–e, SEQ ID NOS:8–12) consisting of Muc1 juxtamembrane sequences used for raising antibodies to the extracellular, non-shed region of Muc1.

Similarly, in FIG. 2A there is shown an exemplary sequence of a human Muc16 protein (SEQ ID NO:20) that has, as its C-terminus, a translation of GENBANK Admission No. AF361486 (Yin, B. W. T., Lloyd, K. O. (2001) Molecular Cloning of the CA125 Ovarian Cancer Antigen., J Biol Chem 276,27371–37375), and has an amino terminal sequence and tandem repeat sequence that is translated from GENBANK Admission No. AF414442 (O'Brien, et al. (2000) Tumour Biology 22, 348–66, which reference potentially includes the entire CA125 sequence). In FIG. 2A only the first two of the tandem repeats units containing 156 amino acids each are shown (/–/ indicates the gap where the remaining tandem repeats occur; Muc16, unlike Muc1, does not contain identical repeats). Thus far, 45 distinct tandem repeat sequences have been identified although the number present in the Muc16 sequence may be as high as 60 as individual repeats occur more than once. The C-terminal domain of O'Brien et al. varies only by a few amino acids from that published by Yin, et al. (supra). As is the case for the examples of Muc1 cited herein, the juxtamembrane sequences of the two Muc16 examples herein is also conserved.

The following features are present within the Muc16 C-terminal domain:

a transmembrane domain having the sequence

FWAVIL IGLAGLLGLI TCLICGVLV;    (SEQ ID NO:4)

a potential furin cleavage site having the sequence

RNKR;                                      (SEQ ID NO:5)

a potential stromolysin site having the sequence

SPLA.                                      (SEQ ID NO:6)

The furin cleavage site may represent a site of post-translational cleavage occurring in the endoplasmic reticulum while the stromolysin site may be a cleavage that results in the release of the shed Muc16.

In FIG. 2B are shown a Muc16 juxtamembrane domain-GST fusion (SEQ ID NO:13) and synthetic peptides (a–e; SEQ ID NOS: 14–18) consisting of Muc16 juxtamembrane sequences used for raising antibodies to the extracellular, non-shed region of Muc16. The "juxtamembrane" region as covered by the Muc16 juxtamembrane domain-GST fusion and synthetic peptides may be longer or shorter than the actual extracellular domain of the non-shed Muc16.

Antibodies of the present invention capable of binding to an epitope of a non-shed extracellular portion of a human Muc1 protein can, for example, be prepared using an antigenic peptide selected from within a region within approximately 90 amino acids N-terminal of the transmembrane region (FIG. 1A). Preferably, an antigenic peptide is from approximately 10 to 30 amino acids in length. The following synthetic peptides (FIG. 1B) are most preferred as antigens and are preferably conjugated to keyhole limpet hemocyanin (KLH):

| a) | QLTLAFREGTINVHDVETQFN | (SEQ ID NO:8) |
| b) | QYKTEAASRYNLTISDVSVSD | (SEQ ID NO:9) |
| c) | FLQIYKQGGFLGLSNIKFRPG | (SEQ ID NO:10) |
| d) | FRPGSVVVQLTLAFREGTINV | (SEQ ID NO:11) |
| e) | VPFPFSAQSGAGVPGWGIA | (SEQ ID NO:12) |

Alternatively, antibodies of the present invention capable of binding to an epitope of a non-shed extracellular portion of a human Muc1 protein can also be produced using an antigen that is a fusion protein such as a Muc1 juxtamembrane domain-GST fusion protein. Thus, the following construct is preferred, in which "GST-" represents glutathione-S-transferase (FIG. 1B):

Antibodies of the present invention can be screened, for example, by the method disclosed in FIG. 3. In this example, antibodies are first screened for the ability to react with cells expressing Muc1 or Muc16. In a further or concurrent step, the antibodies are selected that do not react with Muc1 or Muc16 epitopes that have been shed into the tissue culture media of antigen-expressing cells. Antibodies are thereby identified which react with Muc1 or Muc16 epitopes, but which do not react with epitopes that are shed into tissue culture media. These antibodies are further screened for reaction with serum from ovarian cancer patients using a sandwich ELISA assay in which the capture antibody is the antibody to be screened and the tracer antibody is an antibody recognizing an epitope contained on the shed antigen domain. Alternatively, the tracer antibody can be an antibody recognizing an epitope distinct from the capture antibody but also contained within the juxtamembrane domain. Antibodies that are not reactive with such sera are then exposed to normal and tumor tissue using immunohistochemical staining techniques. Antibodies that are identified as having tumor tissue reactivity, but which are substantially unreactive towards plasma components and normal tissue, are candidate antibodies for the treatment of cancer. Optionally, such candidates can be conjugated to cytotoxic drugs such as, for example, the maytansinoid DM1 (Chari et al., 1992).

Alternatively, mammals can be immunized with cells stably expressing recombinant shed antigen, or portions thereof, such as portions consisting only of the non-shed domain. Suitable vectors for expression in mammalian cells include well-known derivatives of SV-40, adenovirus, ret-

```
GST-FLQIYKQGGFLGLSNIKFRPGSVVVQLTLAFREGTINVHDVETQFNQYKTE    (SEQ ID NO:7)

AASRYNLTISDVSVSDVPFPFSAQSGAGVPGWGIA
```

Antibodies of the present invention capable of binding to an epitope of a non-shed extracellular portion of a human Muc16 protein can, for example, be prepared using an antigenic peptide selected from within a region within approximately 110 amino acids N-terminal of the transmembrane region (FIG. 2A). The following synthetic peptides (FIG. 2B) are most preferred as antigens and are preferably conjugated to KLH:

| a) | SSVLVDGYSPNRNEPLTGNS | (SEQ ID NO:14) |
| b) | TNYQRNKRNIEDALNQLFRN | (SEQ ID NO:15) |
| c) | FRNSSIKSYFSDCQVSTFRSV | (SEQ ID NO:16) |
| d) | SVPNRHHTGVDSLCNFSPLARRV | (SEQ ID NO:17) |
| e) | DRVAIYEEFLRMTRNGTQLQNFTLDRSS | (SEQ ID NO:18) |

Alternatively, antibodies of the present invention capable of binding to an epitope of a non-shed extracellular portion of a human Muc16 protein can also be produced using an antigen that is a fusion protein such as a Muc16 juxtamembrane domain-GST fusion protein. Thus, the following construct is preferred (FIG. 2B):

rovirus-derived DNA sequences and shuttle vectors derived from combinations of functional mammalian vectors, functional plasmids and phage DNA. Further eukaryotic expression vectors are known in the art (e.g., P. J. Southern and P. Berg, J. Mol. Appl. Genet. 1, 327–341 (1982); S. Subramani et al, Mol. Cell. Biol. 1, 854–864 (1981); R. J. Kauffmann and P. A. Sharp, "Amplification And Expression Of Sequences Cotransfected with A Modular Dihydrofolate Reductase Complementary DNA Gene," J. Mol. Biol. 159, 601–621 (1982); R. J. Kauffmann and P. A. Sharp, Mol. Cell. Biol. 159, 601–664 (1982); S. I. Scahill et al, "Expression And Characterization Of The Product Of A Human Immune Interferon DNA Gene In Chinese Hamster Ovary Cells," Proc. Natl. Acad. Sci. USA 80, 4654–4659 (1983); G. Urlaub and L. A. Chasin, Proc. Natl. Acad. Sci. USA 77, 4216–4220, (1980)). A suitable vector containing control signals and a DNA to be expressed, such as that encoding an antibody or antibody equivalent, is inserted into a host cell for expression.

The invention also includes functional equivalents of the antibodies described in this specification. Functional equivalents have binding characteristics that are comparable to those of the antibodies, and include, for example, chimer-

```
GST-TNYQRNKRNIEDALNQLFRNSSIKSYFSDCQVSTFRSVPNRHHTGVDSLCNF    (SEQ ID NO:13)

SPLARRVDRVAIYEEFLRMTRNGTQLQNFTLDRSSVLVDGYSPNRNEPLTGNSDLP
``` ized, humanized and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424.

Functional equivalents include polypeptides with amino acid sequences substantially the same as the amino acid sequence of the variable or hypervariable regions of the antibodies of the invention. "Substantially the same" as applied to an amino acid sequence is defined herein as a sequence with at least 80%, preferably at least about 90%, and more preferably at least about 95% sequence identity to another amino acid sequence, as determined by the FASTA search method in accordance with Pearson and Lipman, Proc. Natl. Acad. Sci. USA 85, 2444–2448 (1988).

Chimerized antibodies preferably have constant regions derived substantially or exclusively from human antibody constant regions and variable regions derived substantially or exclusively from the sequence of the variable region from a mammal other than a human. Humanized forms of the antibodies are made by substituting the complementarity determining regions of, for example, a mouse antibody, into a human framework domain, e.g., see PCT Pub. No. WO92/22653. Humanized antibodies preferably have constant regions and variable regions other than the complement determining regions (CDRs) derived substantially or exclusively from the corresponding human antibody regions and CDRs derived substantially or exclusively from a mammal other than a human.

Functional equivalents also include single-chain antibody fragments, also known as single-chain antibodies (scFvs). Single-chain antibody fragments of the present invention are recombinant polypeptides which bind non-shed Muc1 or Muc16 epitopes, but do not bind shed Muc1 or Muc16 epitopes. These fragments contain at least one fragment of an antibody variable heavy-chain amino acid sequence (VH) tethered to at least one fragment of an antibody variable light-chain sequence (VL) with or without one or more interconnecting linkers. Such a linker may be a short, flexible peptide selected to assure that the proper three-dimensional folding of the (VL) and (VH) domains occurs once they are linked so as to maintain the target molecule binding-specificity of the whole antibody from which the single-chain antibody fragment is derived. Generally, the carboxyl terminus of the (VL) or (VH) sequence may be covalently linked by such a peptide linker to the amino acid terminus of a complementary (VL) and (VH) sequence. Single-chain antibody fragments may be generated by molecular cloning, antibody phage display library or similar techniques. These proteins may be produced either in eukaryotic cells or prokaryotic cells, including bacteria.

Single-chain antibody fragments contain amino acid sequences having at least one of the variable or complementarity determining regions (CDR's) of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Functional equivalents further include fragments of antibodies that have the same, or comparable binding characteristics to those of the whole antibody. Such fragments may contain one or both Fab fragments or the F(ab')2 fragment. Preferably the antibody fragments contain all six complement determining regions of the whole antibody, although fragments containing fewer than all of such regions, such as three, four or five CDRs, are also functional. Further, the functional equivalents may be or may combine members of any one of the following immunoglobulin classes: IgG, IgM, IgA, IgD, or IgE, and the subclasses thereof.

Conjugates

The conjugates of the present invention comprise the antibody, fragments, and their analogs as disclosed herein, linked to a cytotoxic agent. Preferred cytotoxic agents are maytansinoids, taxanes and analogs of CC-1065. The conjugates can be prepared by in vitro methods. In order to link the cytotoxic agent to the antibody, a linking group is used. Suitable linking groups are well known in the art and include disulfide groups, thioether groups, acid labile groups, photolabile groups, peptidase labile groups and esterase labile groups. Preferred linking groups are disulfide groups and thioether groups. For example, conjugates can be constructed using a disulfide exchange reaction or by forming a thioether bond between the antibody and the cytotoxic agent.

Maytansinoids and maytansinoid analogs are among the preferred cytotoxic agents. Examples of suitable maytansinoids include maytansinol and maytansinol analogues. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Taxanes are also preferred cytotoxic agents. Taxanes suitable for use in the present invention are disclosed in U.S. Pat. Nos. 6,372,738 and 6,340,701.

CC-1065 and its analogs are also preferred cytotoxic drugs for use in the present invention. CC-1065 and its analogs are disclosed in U.S. Pat. Nos. 6,372,738; 6,340,701; 5,846,545 and 5,585,499.

An attractive candidate for the preparation of such cytotoxic conjugates is CC-1065, which is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine (B. K. Bhuyan et al., Cancer Res., 42, 3532–3537 (1982)).

Cytotoxic drugs such as methotrexate, daunorubicin, doxorubicin, vincristine, vinblastine, melphalan, mitomycin C, chlorambucil, and calicheamicin are also suitable for the preparation of conjugates of the present invention, and the drug molecules can also be linked to the antibody molecules through an intermediary carrier molecule such as serum albumin.

Diagnostic Applications

For diagnostic applications, the antibodies of the present invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for conjugating the antibody to the detectable moiety may be employed, including those methods described by Hunter, et al., Nature 144:945 (1962); David, e at., Biochemistry 13:1014 (1974); Pain, et al., J. Immunol. Meth. 40:219 (1981); and Nygren, J. Histochem. and Cytochem. 30:407 (1982).

Immunoassay

The antibodies of the present invention can be employed in any known assay method, such as competitive binding assays, direct and indirect sandwich assays, and immunoprecipitation assays (Zola, Monoclonal Antibodies: A Manual of Techniques, pp. 147–158 (CRC Press, Inc., 1987)).

The antibodies of the invention also are useful for in vivo imaging, wherein an antibody labeled with a detectable moiety such as a radio-opaque agent or radioisotope is administered to, a subject, preferably into the bloodstream, and the presence and location of the labeled antibody in the host is assayed. This imaging technique is useful in the staging and treatment of malignancies. The antibody may be labeled with any moiety that is detectable in a host, whether by nuclear magnetic resonance, radiology, or other detection means known in the art.

The antibodies of the invention also are useful as affinity purification agents. In this process, the antibodies are immobilized on a suitable support, such a Sephadex resin or filter paper, using methods well known in the art.

Therapeutic Applications

For therapeutic applications, the antibodies or conjugates of the invention are administered to a subject, in a pharmaceutically acceptable dosage form. They can be administered intravenously as a bolus or by continuous infusion over a period of time, by intramuscular, subcutaneous, intraarticular, intrasynovial, intrathecal, oral, topical, or inhalation routes. The antibody may also be administered by intratumoral, peritumoral, intralesional, or perilesional routes, to exert local as well as systemic therapeutic effects.

Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The method of the present invention can be practiced in vitro, in vivo, or ex vivo.

The method of the present invention may be used for screening and/or treatment a cancer in which Muc1 or Muc16 expression is elevated. Examples of such cancers in which at least Muc1 is elevated include, but are not limited to, cancers of the ovary, breast, lung, pancreas and prostate. Examples of cancers in which at least Muc16 is elevated include, but are not limited to, serous cystadenoma of the ovary, and carcinoma of the pancreas, liver or colon.

When present in an aqueous dosage form, rather than being lyophilized, the antibody typically will be formulated at a concentration of about 0.1 mg/ml to 100 mg/ml, although wide variation outside of these ranges is permitted.

For the treatment of disease, the appropriate dosage of antibody or conjugate will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The antibody is suitably administered to the patient at one time or over a series of treatments.

Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded.

EXAMPLES

Example 1

Generation of Monoclonal Antibodies to the Extracellular Cell-Associated Domains of Muc1 and Muc16

Panels of monoclonal antibodies (Mabs) were raised against putative non-shed extracellular epitope(s) of human Muc1 or Muc16 by immunizing mice with synthetic peptides (Boston BioMolecules, Inc.) representing 20 or 21 amino acid sequences selected from the extracellular juxtamembrane regions of these molecules. Specifically, Muc16 Peptide a, SSVLVDGYSPNRNEPLTGNS (SEQ ID NO: 14), representing residues 11644–11663 of CA125 (Muc16; SEQ ID NO:20); and Muc1 Peptide a, QLTLAFREGTINVHDVETQFN (SEQ ID NO:8), representing residues 362–382 of Muc1 (SEQ ID NO:19), were used to generate Mabs.

To enhance immune responses in mice, the synthetic peptides were conjugated with the carrier protein keyhole limpet hemacyanin (KLH) via a cysteine residue added to the amino termini of the peptides at the time of synthesis (Boston BioMolecules, Inc.) and mixed with complete or incomplete Freund's adjuvant before immunization. Two or three female Balb/c mice for each peptide were injected subcutaneously with 20 μg of antigen per mouse, followed by five or more boosts with the antigen plus Freund's adjuvant. On day 3 after the last antigen injection, the immunized mice were sacrificed and their spleens were removed under sterile conditions for preparation of spleen cells.

Splenocytes from the immunized mice were fused with mouse myeloma P3X63Ag8.653 cells using polyethylene glycol-1500 as fusogen to generate hybridoma clones according to standard protocols (Harlow and Lane, 1988, Antibodies: A Laboratory Manual) with modifications. After cell-fusion, cells were plated in HAT selection medium in 96-well plates and cultured at 37° C. in 5% $CO_2$. One cell-fusion experiment was performed for each antigen, generating 385 Muc16 and 692 Muc1 hybridoma supernatants which were screened for the presence of specific antibodies by peptide ELISA and flow cytometry, as described below. Several hybridoma clones of supernatants showing good reactivity in both assays were expanded and further characterized. The hybridomas were maintained in RPMI (Cambrex) supplemented with 15% heat-inactivated fetal bovine serum (Atlas), 50 Units/ml of penicillin/50 µg/ml streptomycin (Cambrex), 2 mM L-Glutamine (Cambrex).

Example 2

Screening of monoclonal antibodies to the extracellular cell-associated domains of Muc1 and Muc16 by ELISA Peptide-specific antibodies in hybridoma supernatants were screened initially using a solid phase peptide ELISA in which a biotinylated preparation of the non-KLH-conjugated specific peptide (Boston BioMolecules, Inc.) was used as the capture antigen. Immulon H2B 96-well plates were coated with 250 ng per well (50 µl at 5 µg/ml) of NeutrAvidin (Pierce), in 0.5 M carbonate buffer, pH 10 for 4–6.5 hours at room temperature with rocking. The wells were washed twice with 300 µl per well of wash buffer (Tris Buffered Saline (TBS)/0.1% Tween-20) and blocked with 200 µl per well of TBS/3% BSA for 1 hour at room temperature with rocking. The biotinylated Muc1 Peptide a or Muc16 Peptide a were captured by the NeutrAvidin by incubation with 50 ng per well (50 µl of 1 µg/ml) of biotinylated peptide for 1 hour at room temperature (Muc16) or overnight at 4° C. (Muc1) with rocking. The wells were washed twice with 300 µl TBS/0.1% Tween-20 prior to addition of 20 µl TBS/0.1% Tween-20/1.5% BSA (1% BSA for Muc1) and 30 µl of the hybridoma supernatants corresponding to the immobilized peptides, and the plates were rocked at 4° C. overnight (Muc16) or at room temperature for 1 hour (Muc1). Wells were again washed twice with 300 µl TBS/0.1% Tween-20. Secondary antibody, 100 µl (50 µl for Muc1) goat anti-mouse IgG conjugated to horse radish peroxidase (Jackson Laboratories, 115-035-062) diluted 1:3000 in TBS/0.1% Tween-20/1.5% BSA (1% BSA for Muc1), was added for 1 h at room temperature with rocking. Wells were washed five times with TBS/0.1% Tween-20, developed with 100 µl 2,2' Azino-bis(3-ethylbenzothiazoline-6-sulfonic acid) Diammonium Salt (ABTS) (Fluka) substrate at 1 mg/ml in citrate buffer, pH 4.2, containing 0.03% $H_2O_2$, and the color development measured at A405 after 10–20 minutes with a EL808 Microplate Reader (Bio-Tek Instruments).

Muc16

Of 385 hybridoma supernatants tested from mice immunized with Muc16 Peptide a, 28 were strongly positive and 54 were moderately positive for binding to the peptide antigen. Specificity of the antibodies in the hybridoma supernatants for binding to the immunizing peptide was confirmed by companion ELISAs showing no detectable binding to an irrelevant peptide (Muc16 Peptide b, SEQ ID NO:15; data not shown).

Muc1

Hybridoma supernatants of 692 clones from mice immunized with Muc1 Peptide a were screened by ELISA for binding to a biotinylated version of the immunizing peptide. The results are summarized in Table 1. Seventy-two percent of the clones exhibited binding to the peptide, with approximately 25% of these showing strong binding.

TABLE 1

Summary of ELISA screen of 692 hybridoma supernatants from mice immunized with Muc1 Peptide a.

| Binding | % clones |
|---------|----------|
| ++++    | 1.4      |
| +++     | 16       |
| ++      | 14       |
| +       | 40       |
| −       | 28       |

Example 3

Screening of Monoclonal Antibodies to the Extracellular Cell-Associated Domains of Muc1 by Flow Cytometry In addition to ELISA screening, the hybridoma supernatants were screened for binding to antigen positive tumor cell lines by flow cytometry. Muc1 hybridoma supernatants were screened using CaOV-3 cells and Muc16 hybridoma supernatants were screened using OVCAR-3 cells. For Muc1 screening, CaOV-3 cells were grown to 95% confluency on 15 cm tissue culture plates in complete media RPMI (Cambrex) supplemented with 10% heat-inactivated fetal bovine serum (Atlas), 50 Units/ml of penicillin/50 µg/ml streptomycin (Cambrex), 2 mM L-Glutamine (Cambrex)) at 37° C. in 5% $CO_2$. Cells were given 30 ml of fresh media one day before harvest. The cells were washed twice with phosphate buffered saline (PBS) and dissociated from the plate by incubation with 3 ml of Cellstripper (Mediatech, Inc.) at 37° C. for 10 minutes. The cells were washed in 20 ml of ice cold FACS Buffer (2% Goat Serum in RPMI), counted in a hemacytometer, and the concentration adjusted to $10^6$ cells/ml in FACS buffer. Cells were seeded at $10^5$ cells/well (100 µl) in a 96-well round bottom plate (Falcon). After 30 µl of hybridoma supernatant was added to each well, the plates were incubated for approximately 3 hours on ice. The cells were pelleted in a tabletop centrifuge (400×g, 5 min, 4° C.), washed twice with 150 µl of FACS buffer and resuspended in 100 µl of 15 µg/ml FITC-conjugated goat anti-mouse IgG (Jackson ImmunoResearch Laboratories, Inc.). The plates were covered with aluminum foil and incubated for 1 hour on ice. The cells were washed twice with FACS buffer and fixed with 175 µl of 1% formaldehyde in PBS. The samples were scanned and analyzed with a Becton Dickinson FACSCalibur flow cytometer. A commercially available Muc1 antibody, CM1 (Applied Immunochemicals, Inc.) recognizing the variable number tandem repeat (VNTR) domain was included as a control for the flow cytometry screen.

The results showed that CM1 bound to greater than 98% of the CaOV3 cells. In contrast, the antibodies in the hybridoma supernatants exhibited binding that fell into two broad categories: those which appeared to bind to the entire cell population and those which appeared to bind to a subset of the cell population. A total of twelve clones representative of both categories were chosen for further study (See FIG. 4A & 4B and Table 2). These clones were expanded for freezing and subcloned.

TABLE 2

Summary of hybridoma supernatant screen by flow cytometry for 12 selected clones from mice immunized with Muc1 Peptide a.

| Clone | Flow cytometry | | | | ELISA |
|---|---|---|---|---|---|
| | % gated | RFU | % gated | RFU | $A_{405}$ |
| 2C12 | 100 | 46.38 | 80.8 | 55.0 | 2.683 |
| 10B7 | 100 | 39.1 | 73.7 | 49.7 | 0.818 |
| 4H2 | 100 | 46.0 | 63.52 | 67.6 | 1.412 |
| 6H6 | 100 | 27.0 | 47.5 | 46.3 | 0.746 |
| 9B9 | 100 | 21.2 | 40.5 | 40.7 | 0.256 |
| 7C10 | 100 | 19.7 | 26.4 | 50.8 | 0.400 |
| 8H1 | 100 | 28.5 | 35.6 | 66.6 | 0.273 |
| 6A4 | 100 | 23.1 | 28.2 | 63.5 | 0.612 |
| 5C11 | 100 | 16.4 | 19.4 | 63.3 | 0.862 |
| 3A3 | 100 | 12.0 | 19.3 | 35.1 | 2.037 |
| 2A10 | 100 | 20.7 | 21.2 | 73.0 | 3.046 |
| 6C7 | 100 | 29.7 | 26.0 | 93.8 | 0.222 |
| 2° only | 100 | 5.0 | 1.32 | 20.1 | 0.063 |
| CM1 | 100 | 997.6 | 98.5 | 1012.7 | n/a |
| 2° only | 100 | 3.9 | 0.7 | 35.1 | 0.063 |

For Muc16 hybridoma screening, the flow cytometry was conducted as for Muc1 with a few modifications. To increase cell surface expression of Muc16 antigen, OVCAR-3 cells were grown to confluency on 15 cm tissue culture plates and incubation continued for 2 days prior to harvesting the cells. FACS buffer was 1 mg/ml bovine serum albumin (BSA) in PBS. Cells were washed in 200 µl of FACS buffer prior to fixation with 200 µl 1% formaldehyde. A Muc16 antibody, M11 (gift from Dr. Timothy O'Brien; University of Arkansas) recognizing the shed domain was used as a control antibody for the flow cytometry screen.

Figure 5B:
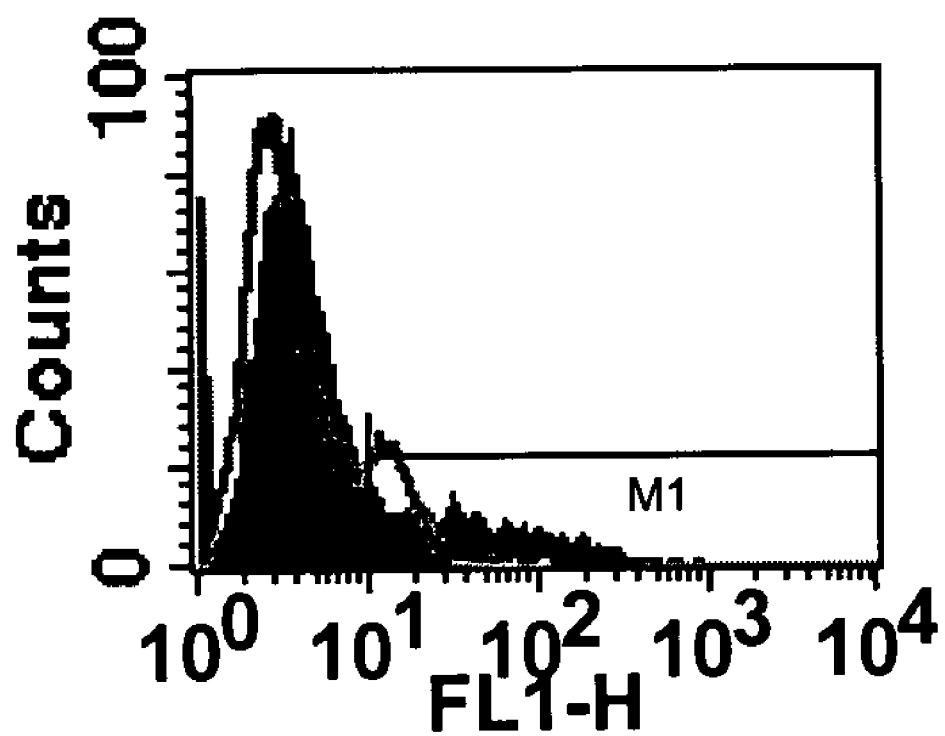

The histograms of 24 representative clones from the Muc16 hybridoma screening are shown in FIG. 5A. The histograms generally fall into three categories: histograms in which a subpopulation of cells exhibit a shift in fluorescence, histograms in which the entire population of cells exhibits a fluorescence shift, and histograms in which two populations of cells show fluorescence shifts of different magnitudes. In FIG. 5B the histogram of an antibody to the Muc16 shed domain, M11, is shown for comparison where approximately 17% of the cells exhibit a fluorescence shift. In Table 3 are compiled the relative fluorescence units (RFU) for the 24 histograms shown in FIGS. 5A & 5B, the percentage of cells shifting to the M1 gate zone shown in the histograms and the corresponding ELISA results.

The twenty-four Muc16 hybridoma clones were expanded and antibodies in the culture supernatants were further characterized as described below. Two of the Muc16 hybridomas, 2F9 and 4E2, subsequently were subcloned and isotyped as IgG1κ. Monoclonal antibodies from these subclones were purified out of cell culture supernatants using Protein A Sepharose and further characterized in cell-based experiments.

TABLE 3

Summary of hybridoma supernatant screening by flow cytometry: Results for 24 selected clones from mice immunized with Muc16 Peptide a.

| Clone | Flow cytometry | | | | ELISA |
|---|---|---|---|---|---|
| | % gated | RFU | % gated | RFU | $A_{405}$ |
| 1B8 | 100 | 13.78 | 15.12 | 68.96 | 1.199 |
| 1D2 | 100 | 65.78 | 18.94 | 327.95 | 0.515 |
| 2F4 | 100 | 20.95 | 15.32 | 112.8 | >3 |
| 3B9 | 100 | 50.39 | 97.23 | 51.65 | 0.952 |
| 4E2 | 100 | 18.79 | 15.09 | 98.91 | >3 |
| 4F8 | 100 | 11.42 | 16.31 | 52.53 | 1.882 |
| 5G1 | 100 | 103.71 | 16.44 | 613.19 | 0.779 |
| 5G8 | 100 | 36.84 | 15.88 | 211.13 | .963 |
| 9E2 | 100 | 13.41 | 16.84 | 60.11 | .661 |
| 9G10 | 100 | 15.65 | 16.18 | 77.18 | 1.089 |
| 10C3 | 100 | 44.69 | 70.61 | 60.12 | >3 |
| 10G2 | 100 | 16.69 | 13.31 | 102.81 | >3 |
| 2A9 | 100 | 63.22 | 36.14 | 162.74 | 0.32 |
| 2E6 | 100 | 11.33 | 13.92 | 57.05 | 0.46 |
| 2F9 | 100 | 186.94 | 97.3 | 191.96 | 0.41 |
| 3C2 | 100 | 30.54 | 96.03 | 31.53 | 0.77 |
| 3E7 | 100 | 38.92 | 86.71 | 43.73 | 0.33 |
| 5C5 | 100 | 76.73 | 23.46 | 312.33 | 0.46 |
| 5E11 | 100 | 42.08 | 59.09 | 67.64 | 0.32 |
| 7G7 | 100 | 85.45 | 26.23 | 311.91 | 0.34 |
| 9D8 | 100 | 66.85 | 17.03 | 371.85 | 0.46 |
| 10C9 | 100 | 66.92 | 19.82 | 320.95 | 0.31 |
| 2D3 | 100 | 11.25 | 17.42 | 40.15 | 1.5 |
| 9G4 | 100 | 6.82 | 15 | 24 | >3 |
| M11 | 100 | 13.34 | 17.348 | 62.284 | |
| 2° only | 100 | 4.88 | 12.15 | 15.91 | 0.08 |

Example 4

Purification of Antibodies

Hybridoma supernatants of stable subclones were used to determine antibody isotypes using Isostrip isotyping strips (Roche) prior to antibody purification. All of the antibodies that were purified were IgG1/κ. For antibody purification, hybridomas were seeded in 15 cm tissue culture plates at $8 \times 10^5$ cells/ml in Hybridoma Serum Free Medium (Gibco) supplemented with 5% Ultra-Low IgG Fetal Bovine Serum (Gibco), 50 Units/ml of penicillin/50 µg/ml streptomycin (Cambrex), 0.6 mM L-Glutamine (Cambrex). Culture supernatant was harvested when the cell density had reached $1.8 \times 10^6$ cells/ml. Sodium chloride was added to the hybridoma supernatant bringing the concentration to 3 M and the supernatant was filtered through a 0.22 micron Millex GV PVDF filter unit (Millipore). Antibodies were purified from 100 ml of hybridoma supernatant on a 1 ml HiTrap recombinant protein A column (Pharmacia) equilibrated with 100 mM Tris pH 8.5 plus 2.5 M NaCl. After loading the column with the hybridoma supernatant, the column was washed with 10 ml of equilibration buffer. Antibody was eluted with 100 mM acetic acid pH 2.8 plus 150 mM NaCl. Peak fractions were collected and neutralized with 2 M potassium phosphate pH 10 and dialyzed against phosphate buffered saline (PBS). Dialyzed antibody was filtered through a 0.22 micron Millex GV PVDF filter unit (Millipore).

Example 5

Construction of a Plasmid for Expression of Recombinant Muc16 Stump Protein in Mammalian Cells A DNA plasmid was constructed for the expression in mammalian cells of a version of Muc16, referred to herein as the recombinant Muc16 Stump (FIGS. 6A & 6B), comprised of the wild-type cytoplasmic and transmembrane domains plus a truncated extracellular domain of Muc16 predicted to contain the non-shed portion of the molecule. The pcDNA3-based plasmid (pcDNA3 Muc1FlagMuc16Myc3) encodes for Muc16 amino acids 11576-11722 flanked by three copies of the Myc epitope tag at the C-terminus and a single copy of the Flag epitope tag at the N-terminus. The Muc1 signal peptide was used to direct the recombinant protein to the endoplasmic reticulum and the cell surface. A detailed description of the steps involved in constructing this plasmid follows.

Cloning Muc16 by PCR:

The Muc16/CA125 Genbank sequence (Yin and Loyd, 2001—accession number NM_024690) was reviewed to design primers for cloning 3.4 kb of the 3' end of the CA125 gene. An overlapping PCR cloning strategy was devised using the primers below.

```
                                            (SEQ ID NO:22)
Muc-5koz:  ttttaagcttaccatgccctttcaagaa (SEQ ID NO:23)
Muc-3:     tttgatatctcattgcagatcctccaggtc (SEQ ID NO:24)
Muc-BG1R:  gggagccgggttggcccatgtccgccatg (SEQ ID NO:25)
Muc-BG1F:  atgggccaacccggctccctcaagttcaac (SEQ ID NO:26)
Muc5end:   ttttaagcttcaccatgcccttgttcaagaacaccagtgtc (SEQ ID NO:27)
Muc3end:   ttttggatcctcattgcagatcctccaggtctagg
```

The first round PCR generated two 1.7 kb products corresponding to the 5' end (using Muc-5 koz and Muc-BG1R) and the 3' end (using Muc-BG1F and Muc-3) of the 3.4 kb CA125 sequence. An Origen human ovary cDNA library (lot# 3012-3) was used as the template for the PCR reactions (50 µl reaction volume: 5 µl 10× Expand reaction buffer (Roche), 4 µl 10 mM dNTP mix, 0.5 µl 100 µM left primer, 0.5 µl 100 µM right primer, 1 µl cDNA, 0.75 µl Expand polymerase (Roche), and 38.25 µl double distilled water). The PCR reactions were run in an MJ Research thermocycler with the following program: 1) 94° C. for 2 min, 2) 94° C. for 20 seconds, 3) 56° C. for 30 seconds, 4) 72° C. for 1.5 minutes, 5) Cycle to step 2 for 35 times, 6) 72° C. for 8 minutes, 7) end. The PCR products were run on a 1% low melt agarose gel and the positive bands were excised, melted at 65° C., and equilibrated to 37° C. for the second round reaction. The overlapping PCR reactions were done similarly to the first round except the Muc5end and Muc3end primers were used, 2.5 µl of each of the gel slices were used as the template, and the extension time was increased to 2 minutes at 72° C. The overlapping PCR reaction was digested with HindIII and BamHI, run on a 1% low melt agarose gel, and ligated into the pBluescriptII (Promega) vector. This overlapping PCR cloning scheme enabled cloning of 2 kb of the 3' end sequence.

Cloning CA125 Sequence for the Stump Expression Vector:

The cloned CA125 sequences contained the entire putative CA125 stump sequence through its 3' end, so these clones were used as templates to build the CA125 stump expression construct. Primers were designed such that the 567 bp 3' end of CA125 could be cloned in-frame with the Muc1 signal peptide and Flag tag to its 5' end and the Myc tag to its 3' end. The final cloning scheme included two PCR reactions utilizing an internal KpnI site for a subsequent dual ligation cloning (see primers below).

```
CA3endNot:

aaaagcggccgcttgcagatcctccaggtcta     (SEQ ID NO:28)

CAKpnF:

gaatggtacccagctgcagaa                (SEQ ID NO:29)

CAKpnR:

gctgggtaccattccgggtcat               (SEQ ID NO:30)

CAXbaF:

caagtctagattccgaaacagcagcatcaa       (SEQ ID NO:31)
```

The CAXbaF and CAKpnR primers were used for the 5' half and the CAKpnF and CA3endNot primers were used for the 3' half. The PCR reaction mixes were made similar to those described above except 5 µl of 20 ng/µl CA125 clone DNA was used as a template and Roche Taq polymerase enzyme was used. The reaction was performed in an MJ Research thermocycler with the following program: 1) 94° C. for 1 min, 2) 94° C. for 15 sec, 3) 55° C. for 1 min, 4) 72° C. for 1 min, 5) Cycle to step 2 for 29 times, 6) 72° C. for 4 min, 7) end. PCR reactions were then digested with KpnI and either XbaI or NotI, run on a 1% low melt agarose gel, excised and ligated together into the XbaI+NotI cut pBluescriptII vector (Promega). Positive clones were sequenced to confirm sequence integrity.

Cloning the Muc1 Signal Peptide by RTPCR:

Total RNA was purified from T47D cells using the Qiagen Qianeasy miniprep kit by following the kit protocol. An RT reaction was run using 2.4 µg of T47D RNA and following the Gibco SuperscriptII protocol for using the supplied random hexamer primers. The suggested reaction conditions (10 min at 25° C., 50 min at 42° C., 15 min at 70° C.) were run in an MJ Research thermocycler. RNA was removed from the RT reaction by incubating at 37° C. with 1 µl RnaseH (Supplied in the Gibco SSII Kit), and then the reactions were used directly in PCR reactions.

Primers for cloning the Muc1 signal peptide sequence were designed based on the Genbank Muc1 sequence (Schroeder et. al, 2003—accession number NM_002456). The target sequence expresses the first 30 amino acids of the Muc1 sequences including the entire signal peptide and its cleavage site. The 5' end primer also included a BamHI cloning site and the 3' end primer included a Flag tag sequence and an XbaI site designed to clone in-frame onto the 5' end of the CA125 sequence (see primers below).

```
Muc1SP5end:    ttttggatccatcacaccgggcacccagtct                                        (SEQ ID NO:32)

FlagMuc1XbaR:  ggaatctagacttgtcatcgtcgtccttgtagtcggtagagcttgcatgaccagaa                (SEQ ID NO:33)
```

The PCR reaction mixes were made similar to those described for the CA125 stump except 2 μl of the RT reaction was used as a template. PCR reactions were digested with BamHI and XbaI run on a 1% low melt agarose gel, excised and ligated into the pBluescriptII vector (Promega). Positive clones were sequenced to confirm sequence integrity.

Figure 7:
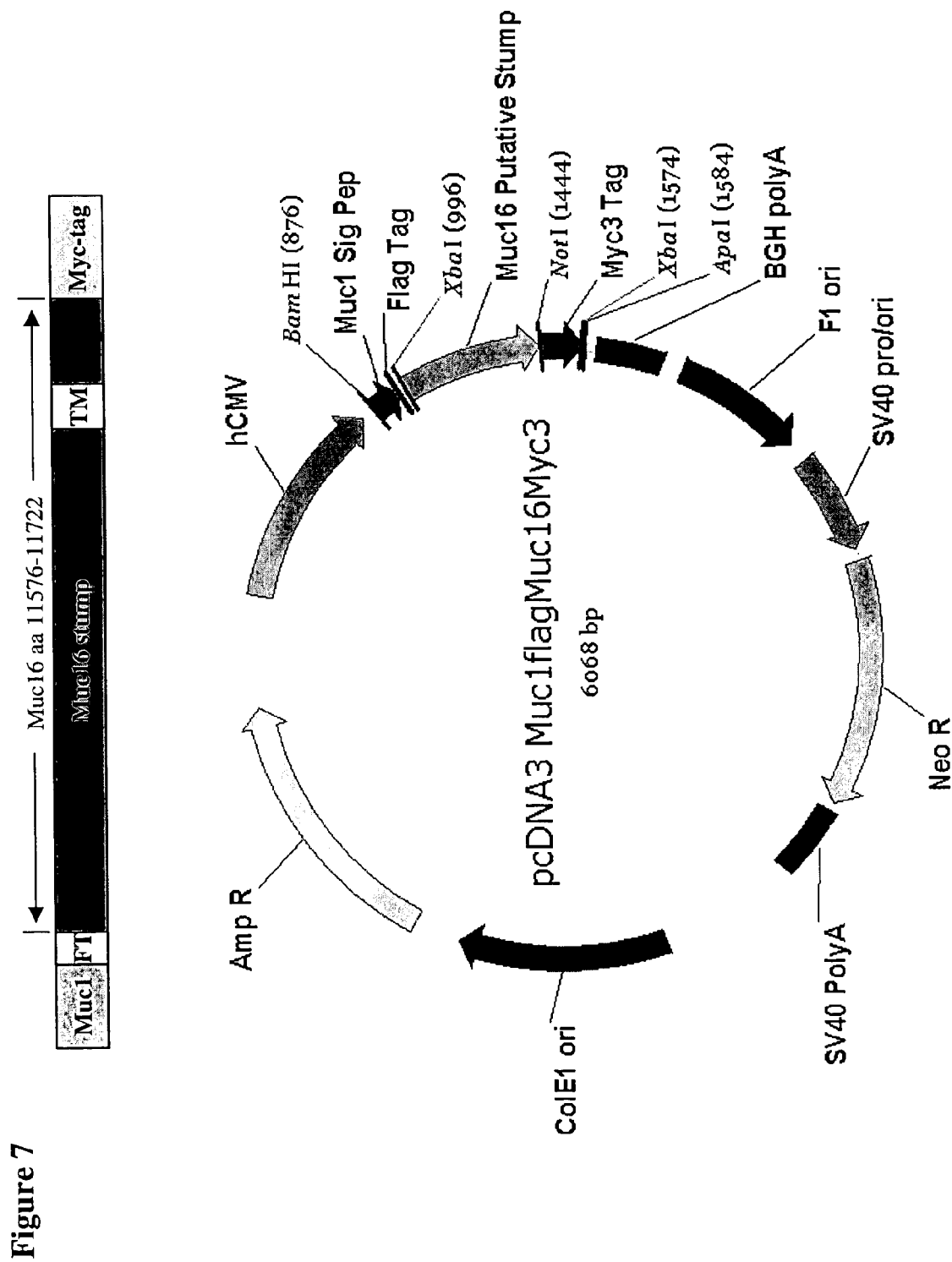
FIG. 7 shows a schematic diagram of the expression plasmid for recombinant Muc16 Stump protein expression. The nucleotide sequence representing amino acids 11576–11722 of Muc16/CA125 was cloned into the pcDNA3/Myc3 mammalian expression vector in frame with an upstream Flag epitope tag and the signal peptide sequence derived from Muc1 and a downstream sequence corresponding to three Myc epitope-tags. The construct, designated pcDNA3 Muc1FlagMuc16Myc3, was used to transfect mammalian tissue culture cells for the expression of recombinant Muc16 Stump protein.

Final Expression Construct Assembly:

Once the individual pieces were constructed and sequences were confirmed, the final expression construct was built by simple restriction digests and ligations into the pcDNA3/Myc3 expression plasmid (Gibco/LifeTechnologies). The diagram in FIG. 6A shows the final assembled construct map and the sequence follows in FIG. 6B. The pcDNA3Muc1FlagMuc16Myc3 plasmid is shown schematically in FIG. 7.

Example 6

Creation of Model Muc16 Antigen-Expressing Cell Lines

The pcDNA3 Muc1FlagMuc16Myc3 plasmid described in Example 5 was used to express the recombinant Muc16 Stump protein utilizing both transient transfections of 293T cells and stable transfections of HeLa cells (Qiagen SuperFect Transfection Reagent, manufacturer's protocols). 293T and HeLa cells were grown in DMEM culture medium (Cambrex) containing 10% fetal bovine serum, 1 mM L-glutamine, 50 Units/ml of penicillin/50 μg/ml streptomycin and transfected with pcDNA3Muc1FlagMuc16Myc3 plasmid or an empty vector plasmid control. Transiently-transfected 293T cells were harvested for western blotting at 25 h post-transfection by washing in PBS and lysing in RIPA buffer (50 mM Tris-HCl, pH 7.2, 150 mM NaCl, 1% NP-40, 0.5% sodium deoxycholate, 0.1% SDS) containing the proteinase inhibitors (Sigma) phenylmethyl sulfonyl fluoride (1 mM), pepstatin (1 μg/ml), and leupeptin (1 μg/ml). To select HeLa cell lines stably expressing the recombinant Muc16 Stump protein, cells were cultured in the presence of 1 mg/ml G418 (BioWhittaker) after transfection. When drug-resistant colonies emerged, expression of the Myc-tagged recombinant Muc16 Stump protein was confirmed by western blotting of RIPA cell lysates using the anti-Myc MAb 9E10 (Invitrogen). Several of the highest expressing HeLa/pcDNA3 Muc1FlagMuc16Myc3 clones were subcloned and used to characterize the anti-Muc16 Peptide a Mabs.

Example 7

SDS-PAGE and Western Blotting

Cell lysates from the transfected cells were denatured by boiling for 5 min in sample buffer (62.5 mM Tris-HCl buffer, pH 6.8, containing 2% w/v SDS, 10% v/v glycerol, 0.001% w/v bromphenol blue, and 5% v/v β-mercaptoethanol) and run according to the method of Laemmli (1970) on 4–20% acrylamide/2.6% bis-acrylamide Tris-Glycine precast mini-gels (Novex). Proteins were electroblotted from the gels onto 0.2μ nitrocellulose filters (Novex) in 32.5 mM Tris/25 mM glycine/0.037% SDS/20% methanol buffer for 2 h using a SemiPhor TE 70 Semi-Dry Transfer Unit (Hoefer Scientific Instruments). Blots were blocked in TBS containing 0.1% Tween-20 and 5% non-fat dry milk (Johnson et al., 1984) for 1 h, incubated overnight with the primary antibodies, and processed using horse radish peroxidase-conjugated secondary antibodies (Amersham Life Science) and ECL (Amersham Life Science), according to the manufacturer's instructions. Primary Mabs were used at 1 to 2 μg/ml.

Figure 8:
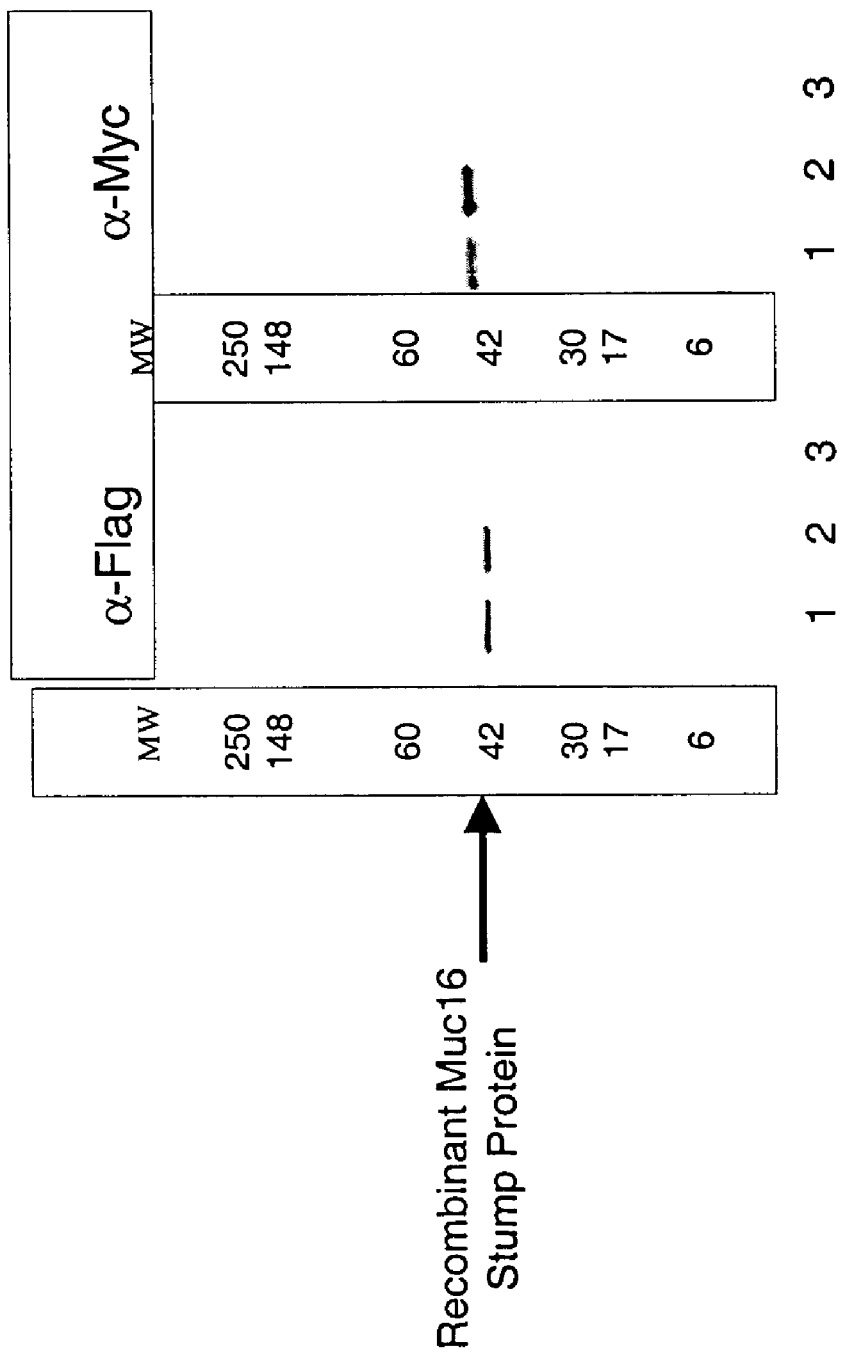
FIG. 8 shows a Western blot of cell lysates from 293T cells expressing the recombinant Muc16 Stump protein. 293T cells were transiently transfected with pcDNA3 Muc1FlagMuc16Myc3 or pcDNA3 empty vector. 25 hours post-transfection, the cell monolayers were lysed in RIPA buffer and portions of the lysates were analyzed by SDS-PAGE and western blotting. Identical samples were probed with mouse anti-Flag tag (left half of blot) or mouse anti-Myc tag (right half of blot) antibodies. Lanes 1 and 2, duplicate lysates from cells transfected with pcDNA3 Muc1FlagMuc16Myc3; lane 3, lysate from cells transfected with pcDNA3 empty vector. The arrow points to the recombinant Muc16 Stump protein detected by both the anti-Flag and anti-Myc antibodies.

The primary antibodies used were anti-Myc tag (MAb 9E10, Invitrogen) and anti-Flag tag antibodies (M2, Sigma). As can be seen in FIG. 8, a single band running at approximately 42 kD was detected in pcDNA3 Muc1FlagMuc16Myc3-transfected cell lysates from duplicate cultures (lanes 1, 2) with either anti-Myc or anti-Flag antibody, but not in the pcDNA3 empty vector-transfected control lysate (lane 3).

The same pcDNA3 Muc1FlagMuc16Myc3 plasmid was transfected into HeLa cells and stable transfectants were selected in G418. Clones were shown to express the recombinant Muc16 Stump protein by western blotting cell lysates, and several high-expressing cell lines were expanded and subcloned.

Figure 9:
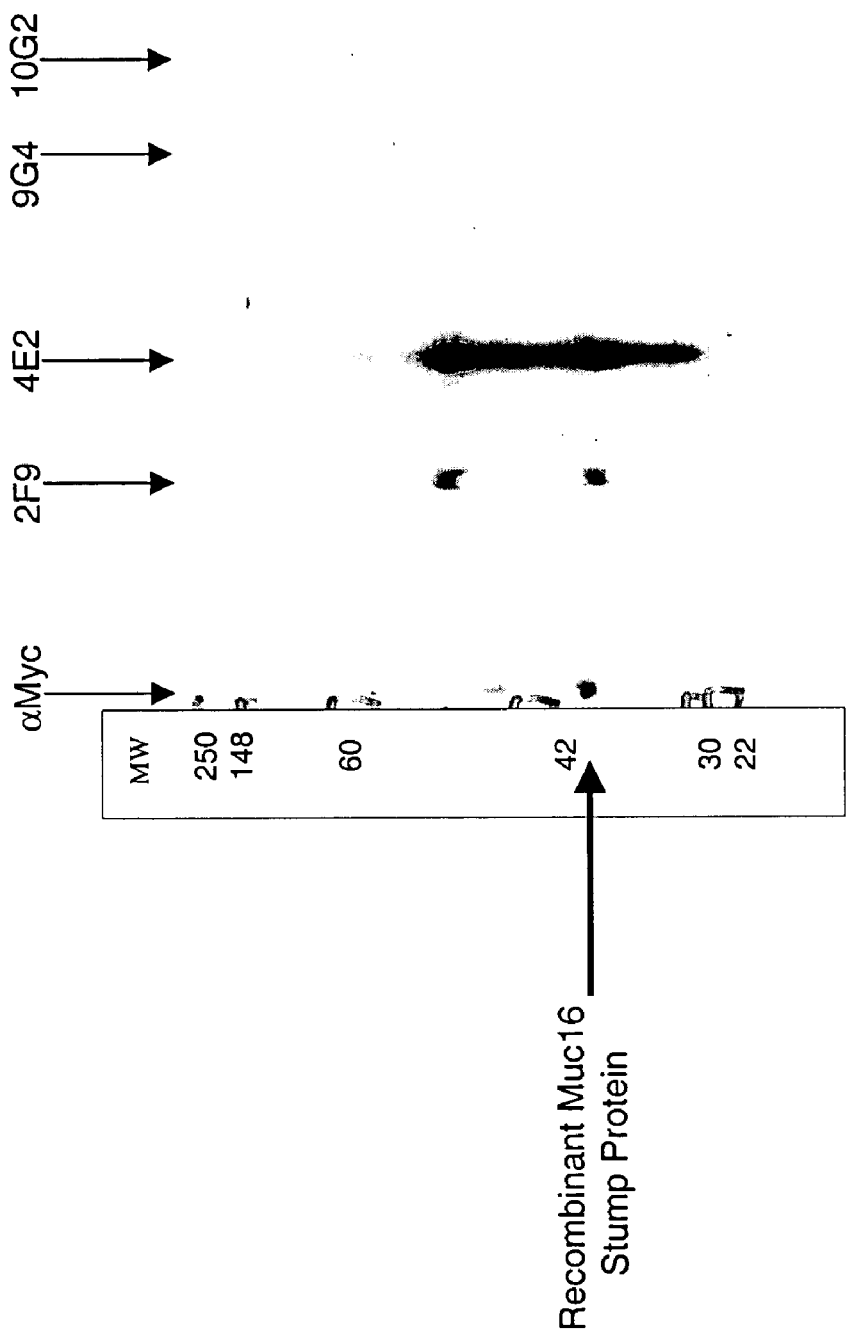
FIG. 9 shows a Western blot screen of anti-Muc16 Peptide a hybridoma supernatants using 293T cells expressing the recombinant Muc16 Stump protein. RIPA lysate prepared from 293T cells transiently transfected with pcDNA3 Muc1FlagMuc16Myc3 was run on a large-well SDS-gel, blotted onto nitrocellulose, and probed with various hybridoma supernatants or the positive control MAb, mouse anti-Myc, using a Miniblotter 28 apparatus from Immunetics to divide the blot into separate lanes. The position of the recombinant Muc16 Stump protein, as identified by the band in the "α-Myc" lane, is indicated with a horizontal arrow. Only those lanes probed with hybridoma supernatants that tested positive (2F9, 4E2, 9G4, 10G2) and the lane probed with mouse anti-Myc are labeled.

To determine whether the antibodies could detect the appropriate epitopes presented in the context of the recombinant Muc16 Stump protein expressed in mammalian cells, western blots were performed using lysates of 293T cells transiently transfected with pcDNA3 Muc1FlagMuc16Myc3. As shown in FIG. 9, antibodies in several of the hybridoma supernatants bound to a 42 kD band co-migrating with the recombinant Muc16 Stump band identified by detection with anti-Myc.

Example 8

Figure 10B:
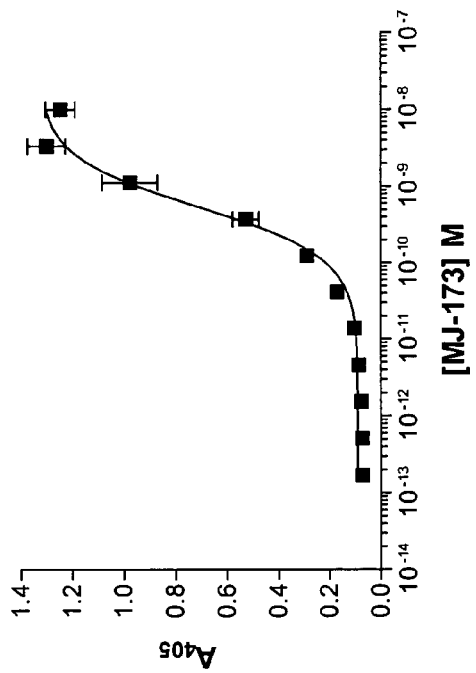
FIG. 10 shows the results of a peptide ELISA showing the binding of purified anti-Muc16 antibodies to Muc16 Peptide a. A biotinylated version of the Muc16 Peptide a that was used to immunized mice was immobilized in the wells of a 96-well plate. Various concentrations of the purified antibodies MJ-171 (FIG. 10A), MJ-173 (FIG. 10B), and MJ-172 (FIG. 10C) were added to the wells (in a 100 µl volume) and incubated for 1 hour at room temperature with rocking. Antibody binding was detected by HRP-labeled goat anti-mouse IgG and the substrate ABTS. Color development was measured at 405 nm. Apparent $K_D$ values were estimated from the antibody concentration required to achieve half maximal binding.
Figure 10A:
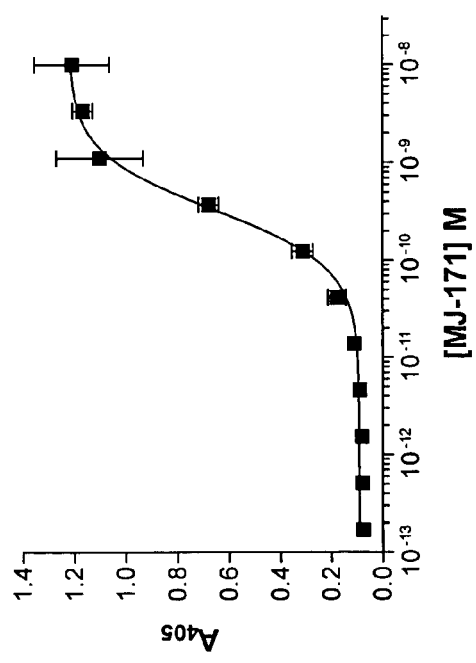
Figure 10C:
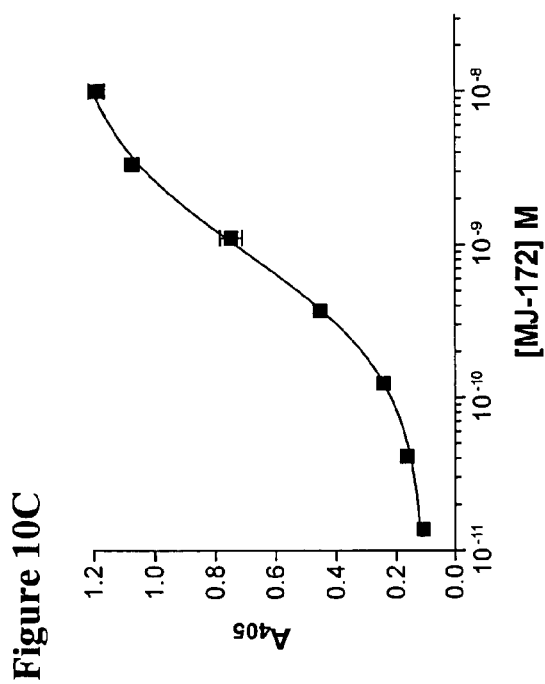

Binding Affinity of Monoclonal Antibodies for Muc16 Peptide a—Estimation of $K_D$ by Peptide ELISA Hybridomas 2F9 and 4E2 were expanded and subcloned. The Mabs, all IgG1κ subtypes, were purified from culture supernatants of subclones 2F9-1E8-1D7 (hereafter referred to as MJ-173), 2F9-1F8-1C10 (hereafter referred to as MJ-172), and 4E2-2D1-1B10 (hereafter referred to as MJ-171) as described above. Apparent $K_D$ for two of the purified Mabs were determined by peptide ELISA using a solid-phase biotinylated peptide capture protocol similar to that described for the initial screening of the hybridoma supernatants except that 100 μl of various concentrations of purified antibody diluted into TBS/0.1% Tween-20/1% BSA was used in place of hybridoma supernatant. The incubation with purified monoclonal antibody was conducted at room temperature for 1 hour. As can be seen in FIG. 10, MJ-173 and MJ-171 bound well to the synthetic peptide antigen, with both Mabs exhibiting saturation binding and an apparent $K_D$ in the range of $3 \times 10^{-10}$ M to $5 \times 10^{-10}$ M as estimated from the antibody concentration required to achieve half maximal binding.

Example 9

Figure 11:
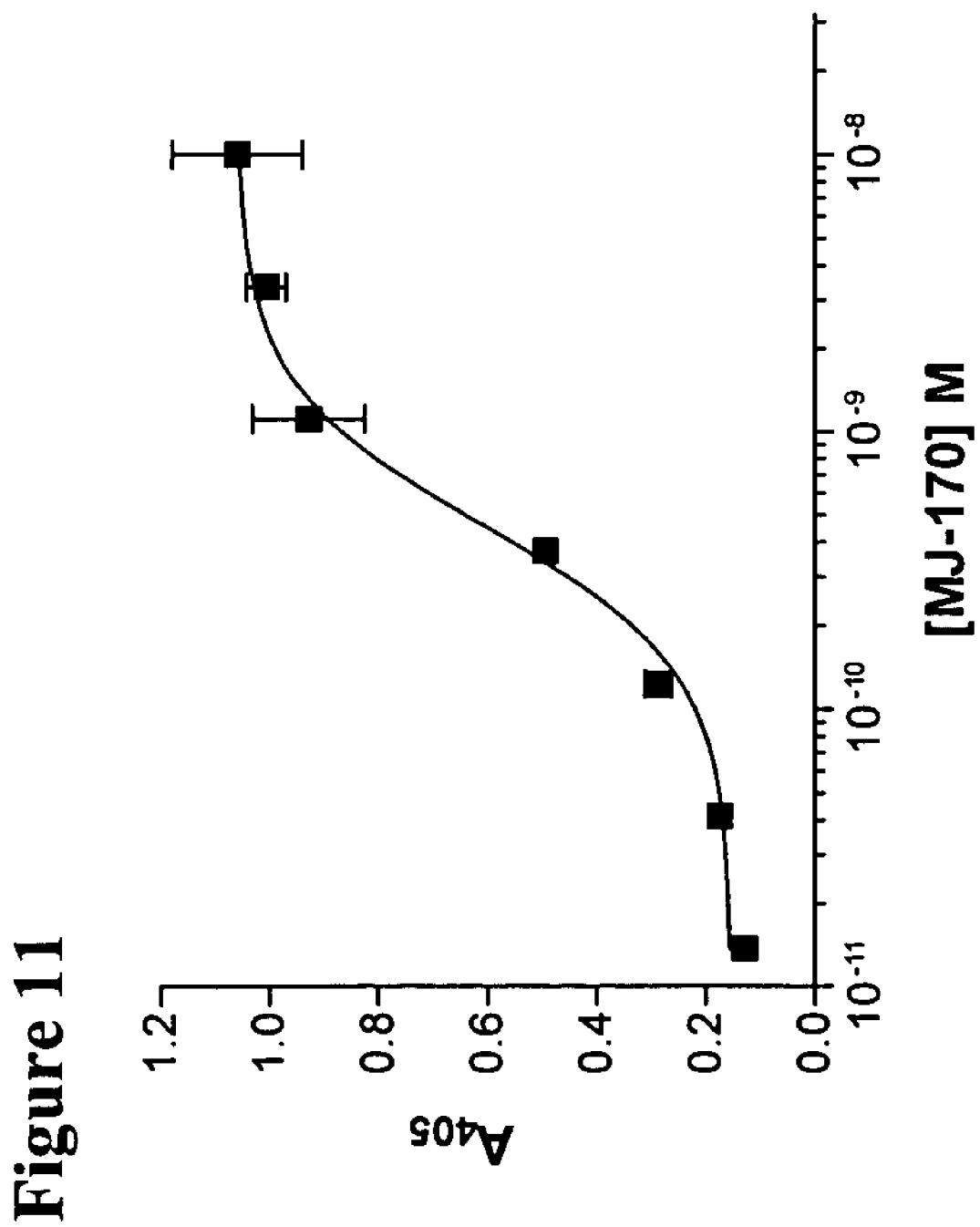
FIG. 11 is the result of a peptide ELISA showing the binding of purified anti-Muc1 antibody, MJ-170, to Muc1 Peptide a. A biotinylated version of the Muc1 Peptide a that was used to immunized mice was immobilized in the wells of a 96-well plate. Various concentrations of purified MJ-170 (100 µl) were added to the wells and incubated for 1 hour at room temperature with rocking. Antibody binding was detected by HRP-labeled goat anti-mouse IgG using the substrate ABTS, with color development measured at 405 nm. The apparent $K_D$ was estimated from the antibody concentration required to achieve half maximal binding.

Binding Affinity of MJ-170 for Muc1 Peptide a—Estimation of $K_D$ by Peptide ELISA Hybridoma clone 3A3 was subcloned to produce 3A3-2A6 (hereafter referred to as MJ-170). Antibody from the MJ-170 hybridoma was purified as described above. The affinity of purified MJ-170 binding to the immunizing peptide, Muc1 Peptide a, was measured by ELISA essentially as described for the ELISA screen except that 100 µl of various concentrations of purified antibody diluted into TBS/0.1% Tween-20/1% BSA was used in place of hybridoma supernatant. The results are shown in FIG. 11. An apparent $K_D$ of $4.5 \times 10^{-10}$ M for MJ-170 binding to Muc1 Peptide a was estimated from the antibody concentration required to achieve half maximal binding indicating that this antibody has high affinity for the immunizing peptide.

Example 10

Indirect Immunofluorescence and Adsorptive Endocytosis Using Anti-Muc16 Peptide a Monoclonal Antibodies The ability of the anti-peptide Mabs to recognize antigen in a cellular context was assessed by indirect immunofluorescence studies using a stable HeLa/pcDNA3 Muc1FlagMuc16Myc3 cell line, subclone #54-1. If the Muc16 Stump localizes properly when expressed in cells, the Myc tags are expected to be intracellular and the Muc16 Peptide a epitope(s) extracellular. In a first experiment, subclone #54-1, or control HeLa empty vector-transfected cells, were plated in culture medium on glass coverslips in 24-well plates, $8 \times 10^4$ cells per well, and allowed to adhere overnight in a 37° C., 5% $CO_2$ incubator. Cell monolayers were washed with PBS, fixed for 25 min in 2% paraformaldehyde/PBS, washed, permeabilized in 0.1% Triton X-100/PBS for 10 min, washed, and blocked in 2.5% normal goat serum/PBS for 1 h, all at room temperature. Primary Mabs were diluted to 1 µg/ml in 2.5% normal goat serum/PBS and incubated with the monolayers for 1 h 40 min with gentle rocking. Anti-Myc was used as a positive control for detecting the recombinant Muc16 Stump protein in permeabilized cells; MOPC21 (Sigma) was used as a negative control antibody. Unbound Mabs were removed with $3 \times 5$ min washes in PBS. Cell-bound Mabs were detected with AlexaFluor 488-conjugated goat anti-mouse IgG (Molecular Probes A-11001, 1:2000 in 2.5% normal goat serum/PBS) added for 1 h. Nuclei were stained with Hoechst #33258 (Sigma) added during the second antibody incubation. The coverslips were washed 3 times (5 min, PBS) and mounted in vinol mounting medium. Fluorescence was viewed on a Nikon Microphot-FXA microscope and photographed using a Spot digital camera (Diagnostic Instruments, Inc.). Mabs MJ-173 and MJ-171 stained the HeLa/pcDNA3 Muc1FlagMuc16Myc3 cells, with individual cells showing a wide range of fluorescence intensity. This heterogeneous pattern was also observed following staining with anti-Myc. In the control (non-recombinant Muc16 Stump-expressing) HeLa/pcDNA3 cells a faint cytoplasmic staining was seen with the anti-Muc16 peptide Mabs, but not with anti-Myc.

In a second experiment, adsorptive endocytosis was performed on live cells, using a variation of the indirect immunofluorescence protocol described above. Primary Mabs were added directly to the culture medium of growing cells to a final concentration of 2 µg/ml, and incubated with the cell monolayers for 1 h in a 37° C., 5% $CO_2$ incubator with occasional rocking. Following this incubation period to allow Mab binding to cell surface epitopes and internalization of the antigen-antibody complexes, the cell monolayers were washed quickly three times with PBS, and then fixed, permeabilized, and probed with AlexaFluor-labeled secondary antibody and Hoechst as above. A transferrin receptor Mab (CD71, Santa Cruz #7327) was used as a positive control for tracking a protein expected to be present on the extracellular surface and capable of rapid internalization. Anti-Myc was used as a negative control in this experiment since the Myc epitope tag on the recombinant Muc16 Stump protein is expected to be intracellular and unavailable to binding by Mabs added to the extracellular milieu. As expected, in live control HeLa cells only the anti-transferrin receptor MAb bound to the cell surfaces and was endocytosed into intracellular compartments. In HeLa/pcDNA3 Muc1FlagMuc16Myc3 cells both the anti-transferrin receptor Mab and Muc16 Mabs, MJ-173 and MJ-171, bound and were internalized well. No staining was observed when anti-Myc was added to the live cell culture, confirming that the orientation of the recombinant Muc16 Stump protein in the plasma membrane was as predicted.

Example 11

Binding of Purified Muc16 Monoclonal Antibodies to Tumor Cells

The binding of antibodies from purified Muc16 clones MJ-173 and MJ-171 to various tumor cell lines was analyzed by flow cytometry. In an effort to optimize Muc16 cell surface expression, the cells were plated at a density covering approximately 50% of the tissue culture plate. Incubation was continued for 6–8 days without refreshing spent media (Konishi et al., 1994) at which time cells were harvested and flow cytometry performed essentially as described above for the screen except that 100 µl purified antibody diluted to various concentrations into FACS buffer (1 mg/ml BSA in PBS) was used in place of hybridoma supernatant. Avidity of purified antibody for cells was estimated by determining the antibody concentration required to achieve half maximal binding. The binding to WISH cells of a commercially available antibody recognizing the shed tandem repeat domain of Muc16 (OC125; Cell Marque CMC242) was included as a control.

Figure 12F:
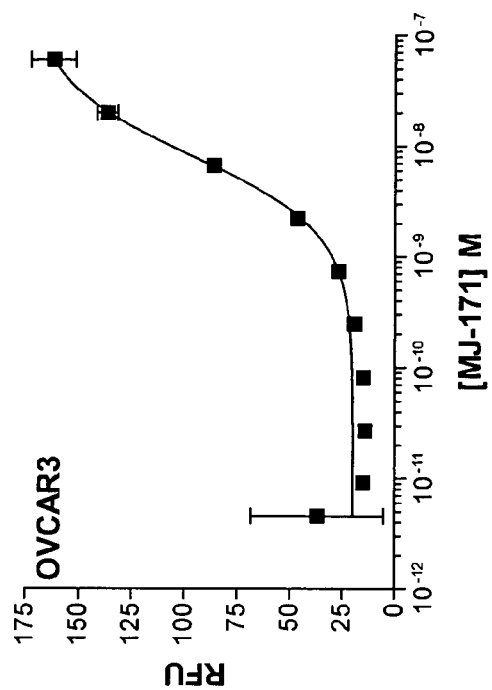
FIG. 12F: Binding of MJ-171 to OvCar3 cells.
Figure 12E:
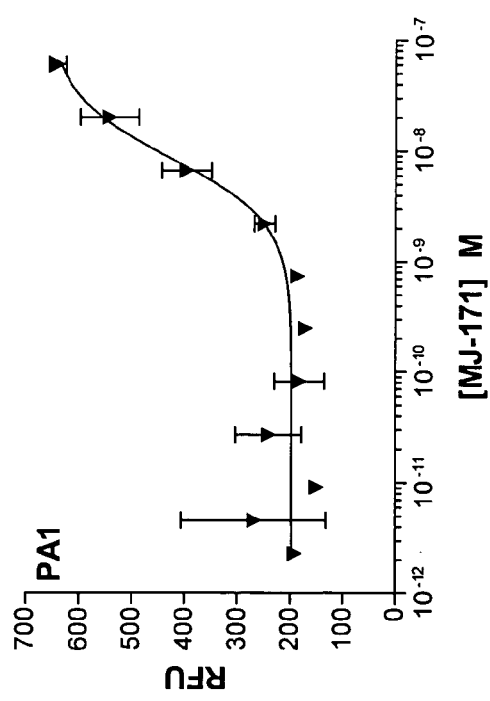
FIG. 12E: Binding of MJ-171 to PA-1 cells.
Figure 12G:
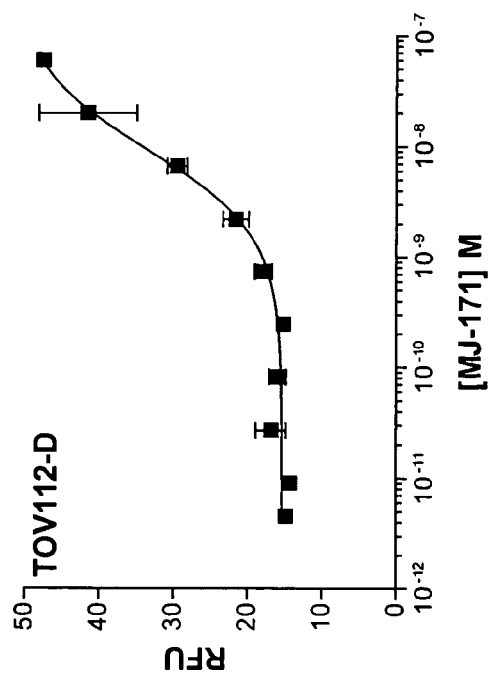
FIG. 12G: Binding of MJ-171 to Tov112-D cells.

The results are shown in FIG. 12 and Table 4. Clone MJ-171 exhibited saturable binding to several tumor cell lines. Clone MJ-173 binding to OV90 cells was virtually indistinguishable from the binding to clone MJ-171. In all cases, the antibodies recognizing the non-shed domain only bound to a subset of the cell population possibly indicating cell cycle-dependent changes in epitope expression or accessibility. In contrast, 95% of WISH cells bound to the OC125 antibody recognizing a shed domain epitope. The fluorescence shift at saturation binding of WISH cells was more than 5-fold higher with the OC125 antibody (248 RFU) compared with clone MJ-171 (41 RFU) consistent with multiple tandem repeat epitopes per Muc16 molecule for the OC125 antibody compared with a single juxtamembrane epitope for the MJ-171 antibody. The ovarian tumor cell lines, OVCAR3 and PA-1, exhibited the highest RFU suggesting that these cell lines express high levels of accessible Muc16 non-shed epitope. The estimated apparent avidities of MJ-171 and MJ-173 for various tumor cell lines was in the range of $1-9 \times 10^{-9}$ which was less than the apparent $K_D$ measured for binding to the immunizing peptide.

TABLE 4

Summary of flow cytometry data
(FIG. 12) for purified Muc16 antibodies

| Cell Line | Antibody | % Gated | $^a$RFU | % Gated | $^a$RFU | $^b$Apparent Avidity (M) |
|---|---|---|---|---|---|---|
| WISH | MJ-171 | 100 | 10.15 | 16 | 41.31 | $1.3 \times 10^{-8}$ |
| WISH | OC125 | 100 | 236.71 | 95 | 248.23 | $^c$not determined |
| SkBr3 | MJ-171 | 100 | 13.35 | 36 | 28.01 | $4 \times 10^{-9}$ |
| OV90 | MJ-171 | 100 | 10.23 | 17 | 40.44 | $7.2 \times 10^{-9}$ |
| OV90 | MJ-173 | 100 | 10.29 | 19 | 38.20 | $5.8 10^{-9}$ |
| PA-1 | MJ-171 | 100 | 150.59 | 20 | $^d$641.57 | $5.5 \times 10^{-9}$ |
| OVCAR3 | MJ-171 | 100 | 30.06 | 17 | 162.00 | $8 \times 10^{-9}$ |
| Tov112-D | MJ-171 | 100 | 15.74 | 27 | 47.46 | $9 \times 10^{-9}$ |

$^a$Relative fluorescence units (RFU) at saturation binding.
$^b$Estimated from antibody concentration giving half maximal binding.
$^c$The purity of this OC125 antibody was unknown preventing avidity estimation.
$^d$This experiment exhibited unusually high background fluorescence (~200 RFU).

Example 12

Binding of Purified Muc1 Monoclonal Antibodies to Tumor Cells

Figure 13A:
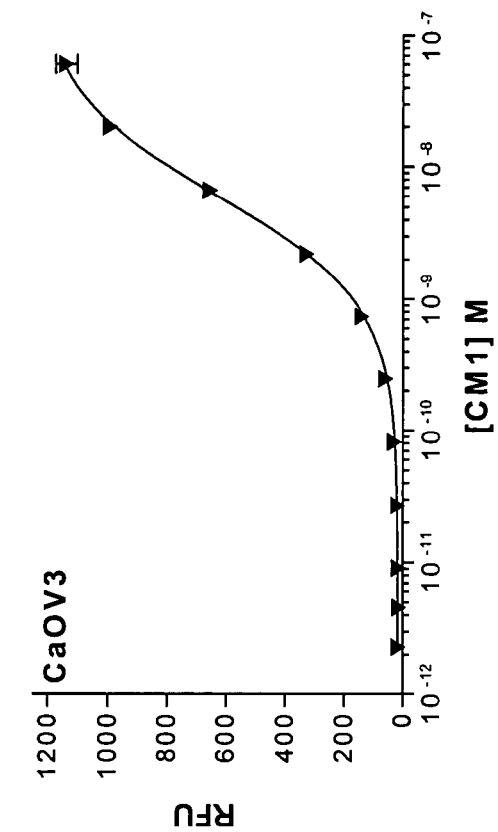
FIGS. 13A & 13B.
Figure 13B:
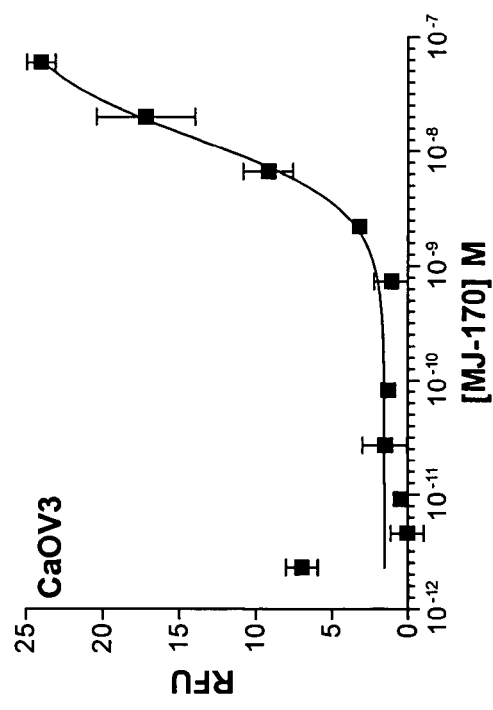

Binding to the ovarian cancer tumor cell line, CaOV3, was analyzed by flow cytometry as described above for the screen of anti-Muc16 antibodies except that 100 µl various concentrations of purified antibody diluted into FACS buffer (1 mg/ml BSA in PBS) was used in place of hybridoma supernatant. The results are shown in FIG. 13A. A subset of the cell population exhibited a fluorescence shift indicative of antibody binding. The apparent avidity of MJ-170 for CaOV3 cells is estimated to be $1.3 \times 10^{-8}$ M from the concentration of antibody required to achieve half maximal binding suggesting that MJ-170 binds more tightly to the immunizing peptide than to cells. FIG. 13B shows the binding of CM1 (Applied Immunochemicals), a Muc1 VNTR antibody, to CaOV3 cells. As expected, the maximum relative fluorescence seen with CM1 is considerably higher (approximately 40-fold) than with MJ-170 reflecting the multiple VNTR epitopes per Muc1 molecule in contrast to the one MJ-170 epitope per Muc1 molecule.

Example 13

Immunohistochemical Staining of HeLa/Recombinant Muc16 Stump Cells and Human Ovarian Cancer Tissue Arrays Immunohistochemical staining conditions were optimized for Mabs MJ-173 and MJ-171 using HeLa/Muc16 Stump #54-1 and control HeLa empty vector-transfected cells. Cells were removed from culture dishes in PBS/2 mM EDTA buffer, washed, pelleted, fixed in 10% buffered formalin, and embedded in paraffin. Formalin-fixed, paraffin-embedded tissue microarrays of human ovarian tumor surgical specimens were purchased from Imgenex (IMH-347). Mabs MJ173 and MJ-171 were used at concentrations showing optimal staining of HeLa/Muc16 Stump #54-1 and minimal background staining of HeLa/pcDNA3 control cell pellets. An anti-Maytansine MAb (ImmunoGen, Inc.) was used as an IgG1κ isotype control.

Conditions used for the experiments discussed were as follows. Muc16 peptide epitopes present in 5 µm sections of the cell pellets or in ovarian cancer tissue arrays were retrieved using one-step deparaffinization/heat-induced antigen retrieval in high pH BORG$_{DECLOAKER}$ according to the manufacturer's instructions (BioCare Medical). All subsequent steps were performed at room temperature. Non-specific binding sites were blocked with PBS/[1x]Power Block (BioGenex)/10% Normal Horse Serum (Vector Laboratories) for 20 min. Primary Mabs, anti-Muc16 Peptide a and control antibodies, were diluted to 1 µg/ml in blocking buffer and incubated with the sections for 45 min. The slides then were washed in PBS, 3 changes for 5 min each. Bound primary antibodies were detected using a biotinylated horse anti-mouse IgG secondary antibody and Vectastain ABC Elite Kit (Vector Laboratories) followed by incubation for 10 min with DAB substrate chromagen (Dako Laboratories). Sections were counterstained with hematoxylin (Shandon). Slides were mounted and viewed under brightfield optics using a Nikon MicroPhot microscope. Photomicrographs were made using a Spot digital camera (Diagnostic Instruments, Inc.).

As in the indirect immunofluorescence experiments presented above, Mabs MJ-173 and MJ-171 produced heterogeneous staining of the HeLa/pcDNA3 Muc1FlagMuc16Myc3 cells, indicating a wide cell-to-cell range of antigen expression levels. The control HeLa/pcDNA3 cells showed a homogeneous background staining level slightly above that of the anti-Maytansine isotype control, but very much fainter than the level of staining observed in the strongly-expressing antigen-positive HeLa/Muc16 Stump cells.

MAb MJ-173 and Mab MJ-171 were used to stain formalin-fixed human ovarian cancer samples in tissue microarrays purchased from Imgenex. Results from this experiment suggested that the CA125 Peptide a antigen can be detected in approximately 42% of the 57 ovarian cancer samples tested.

Example 14

Conjugation of Purified Monoclonal Antibodies to DM1

To determine whether antibodies recognizing the cell-associated domain of Muc16 or Muc1 would be suitable for delivering cytotoxic drugs a maytansinoid drug, DM1, was conjugated to MJ-171 (Muc16) to make MJ-171-DM1, or to MJ-170 (Muc1) to make MJ-170-DM1. Purified antibodies were conjugated to the cytotoxic maytansinoid drug DM1 using a modification of the method described by Chari et al (1992). Briefly, antibody was concentrated to 1–5 mg/ml using Centriprep Plus-20 centrifugal filtration units (Millipore) and dialyzed into Buffer A (50 mM potassium phosphate/50 mM NaCl/2 mM EDTA, pH 6.5). The antibody was modified with the bifunctional linker, N-Sulfosuccinimidyl-4-(5-nitro-2-pyridyldithio)pentanoate (SSNPP) to introduce nitrodithiopyridyl groups. The antibody was incubated with twelve molar equivalents of (SSNPP) in Buffer A plus 5% dimethylacetamide (DMA) for 90 minutes at ambient temperature with stirring. Unreacted linker was removed by dialysis using Slide-A-Lyzer Dialysis Cassettes (Pierce). The extent of modification was determined by measuring the absorption at 325 nm. Using an extinction coefficient at 325 nm for SSNPP of 10,964 $M^{-1}cm^{-1}$ the concentration of nitrothiopyridyl groups was calculated. The antibody concentration was determined by measuring the absorption at 280 and using an extinction coefficient at 280 nm of 224,000 $M^{-1}cm^{-1}$. Spectrophotometric measurements showed that the antibodies were modified with an average of 3–6 nitrothiopyridyl groups per antibody. The modified antibody was conjugated to N2'-deacetyl-N-2'(3-mercapto-1-oxopropyl)-maytansine (DM1) by disulfide exchange. Two equivalents of DM1 per nitrothiopyirdyl group were incubated with 1–3 mg/ml of modified antibody in Buffer A plus 3% DMA for 3 hours at room temperature with stirring. Free DM1 was removed from the conjugate by dialysis as described above and the concentrations of DM1 and antibody measured spectrophotometrically as described in Chari et al (1992). The resulting Muc16 conjugate (MJ-171-DM1) had an average of 2.98 DM1 molecules per molecule of antibody. The resulting Muc1 conjugate (MJ-170-DM1) had an average of 1.2 DM1 molecules per molecule of antibody.

Example 15

Cytotoxicity Assay-MTT

Both the MJ-171-DM1 conjugate and the MJ-170-DM1 conjugate were tested in two in vitro cytotoxicity assays: a standard MTT cell viability assay and a clonogenic assay. In the MTT assay, adherent tumor cell lines were cultured in complete medium RPMI (Cambrex) supplemented with 10% heat-inactivated fetal bovine serum (Atlas), 50 Units/ml of penicillin/50 µg/ml streptomycin (Cambrex), 2 mM L-Glutamine (Cambrex)) at 37° C. in 5% $CO_2$. Cells were dissociated from the tissue culture plate with Trypsin-Versine (EDTA) (Cambrex) and counted using a hemacytometer. Cells were plated in 96-well tissue culture plates at a density of 2000 cells per well in 100 µl of complete medium. Various concentrations of antibody-DM1 conjugate (100 µl) were added to each well and the cells were cultured for 4 to 5 days. Cell viability was assessed by 3-(4,5-Dimethylthiazol-2-yl)-2,5-diphenyltetrazolium bromide (MTT) assay. Briefly, a 5 mg/ml MTT (Sigma) stock solution in PBS was diluted to 1 mg/ml in complete culture medium. 50 µl of 1 mg/ml MTT was added to each well and the plates were returned to the 37° C. incubator. After 3–4 hours, the MTT and culture medium was carefully removed from each well and 150 µl of DMSO (Burdick and Jackson) was used to solubilize the MTT-formazan. The optical density was read on a EL808 UltraMicro Plate Reader (Bio-tek Instruments Inc.) using a 540 µm filter.

Figure 14B:
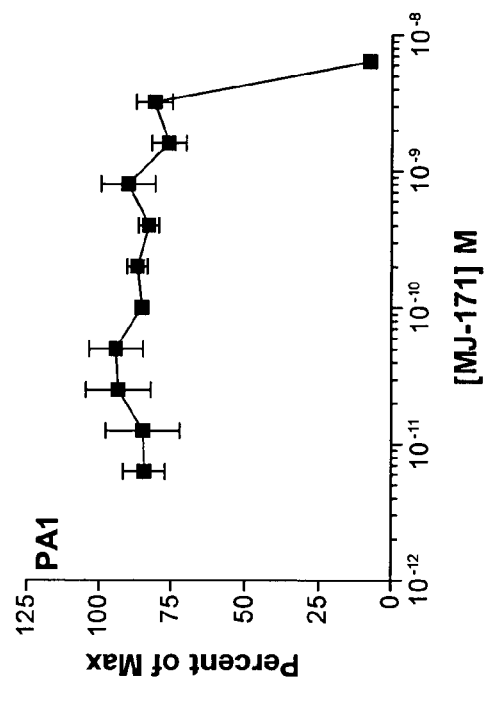
FIG. 14B: PA-1 Cells.
Figure 14A:
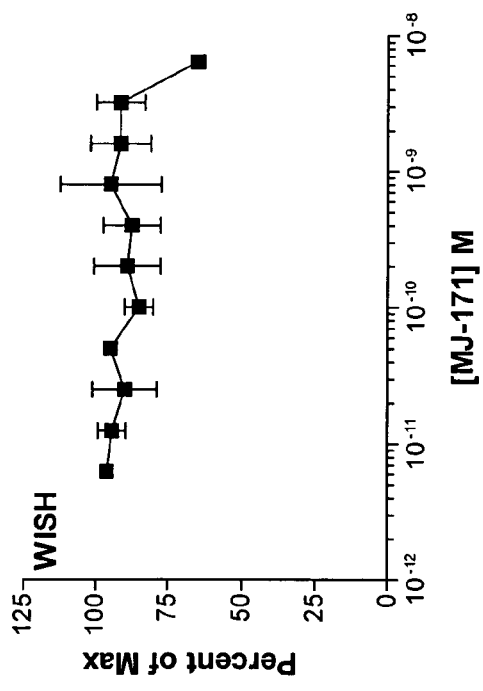
FIG. 14A) WISH Cells.
Figure 14C:
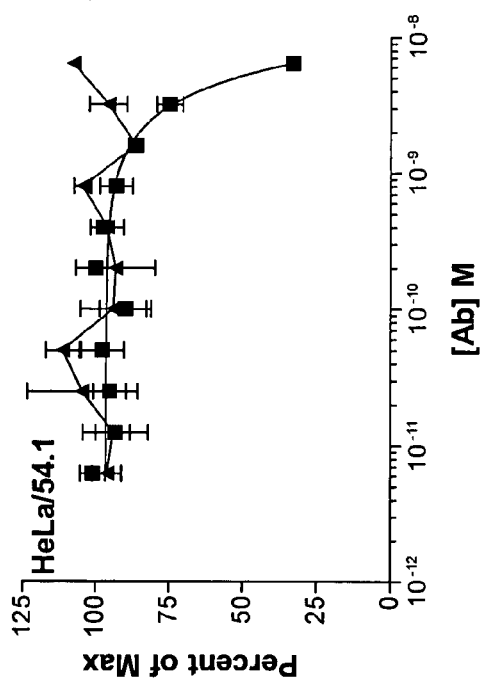
FIG. 14C: HeLa /Muc16 Stump#54-1.

The results for the MJ-171-DM1 conjugate are shown in FIG. 14. The MJ-171-DM1 conjugate showed limited cytotoxicity to WISH cells (FIG. 14A). However, the ovarian tumor cell line PA-1 was killed with an estimated $IC_{50}$ of approximately $5 \times 10^{-9}$ (FIG. 14B). Likewise, the conjugate was cytotoxic to the model cell line, HeLa/Muc16 Stump #54-1, exhibiting an $IC_{50}$ similar to PA-1 cells (FIG. 14C). The cytotoxicity was dependent on DM1 conjugation as no killing was seen with unconjugated MJ-171.

Figure 15:
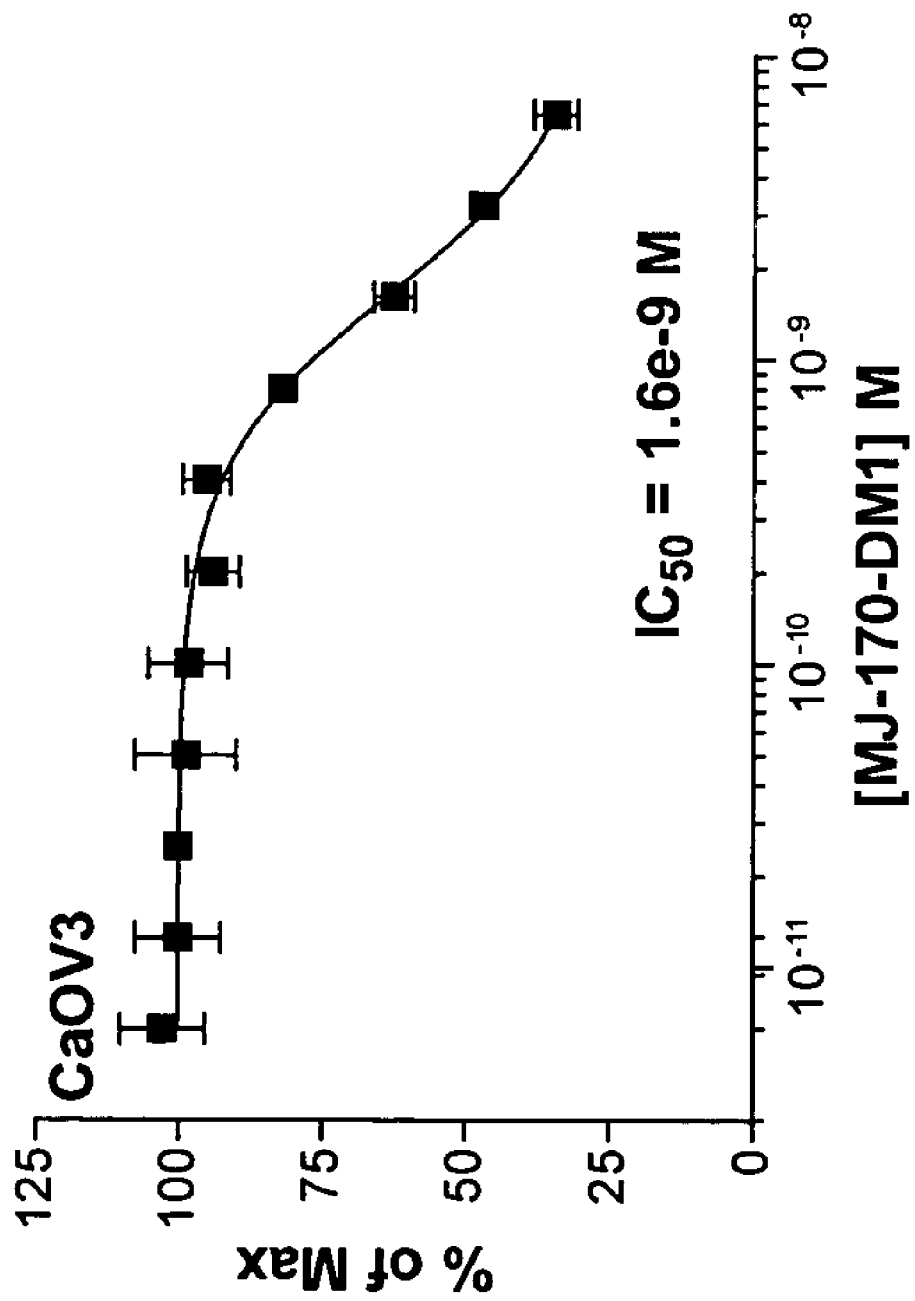
FIG. 15 shows the cytotoxicity of an MJ-170-DM1 conjugate to CaOV3 cells. CaOV3 cells were plated at a density of 2000 cells per well in a 96-well tissue culture plate. Cells were incubated with the indicated concentrations of conjugate for 4 days at which time cell viability was assessed by MTT assay as described for FIG. 14.

The results for the MJ-170-DM1 conjugate are shown in FIG. 15. The $IC_{50}$ is estimated to be $1.6 \times 10^{-9}$ M.

Example 16

Cytotoxicity Assay—Clonogenic

The clonogenic assay measures the effect of conjugate exposure on tumor cell line plating efficiency. Tumor cell lines were grown in RPMI (Cambrex) supplemented with 10% heat-inactivated fetal bovine serum (Atlas), 50 µg/ml Gentamycin (Gibco), and 2 mM L-Glutamine (Cambrex). HeLa/Muc16 Stump #54-1 cells were grown in DMEM (Cambrex) supplemented with 10% heat-inactivated fetal bovine serum (Atlas), 2 mM L-Glutamine, and 1 mg/ml G418. Cells were plated in a 6-well plate at a density of 1000 cells per well. Various concentrations of conjugate were added to each well and the cells were incubated at 37° C. in 5% $CO_2$ until colonies formed (7–8 days). The culture media was removed and colonies were fixed and stained by incubation with 1 ml of crystal violet solution (0.1% crystal violet, 10% formaldehyde in PBS) for 15–30 minutes at room temperature. The wells were washed 3 times with deionized water, allowed to dry, and colonies counted. The plating efficiency was calculated by dividing the number of colonies by the number of cells plated per well.

Figure 16:
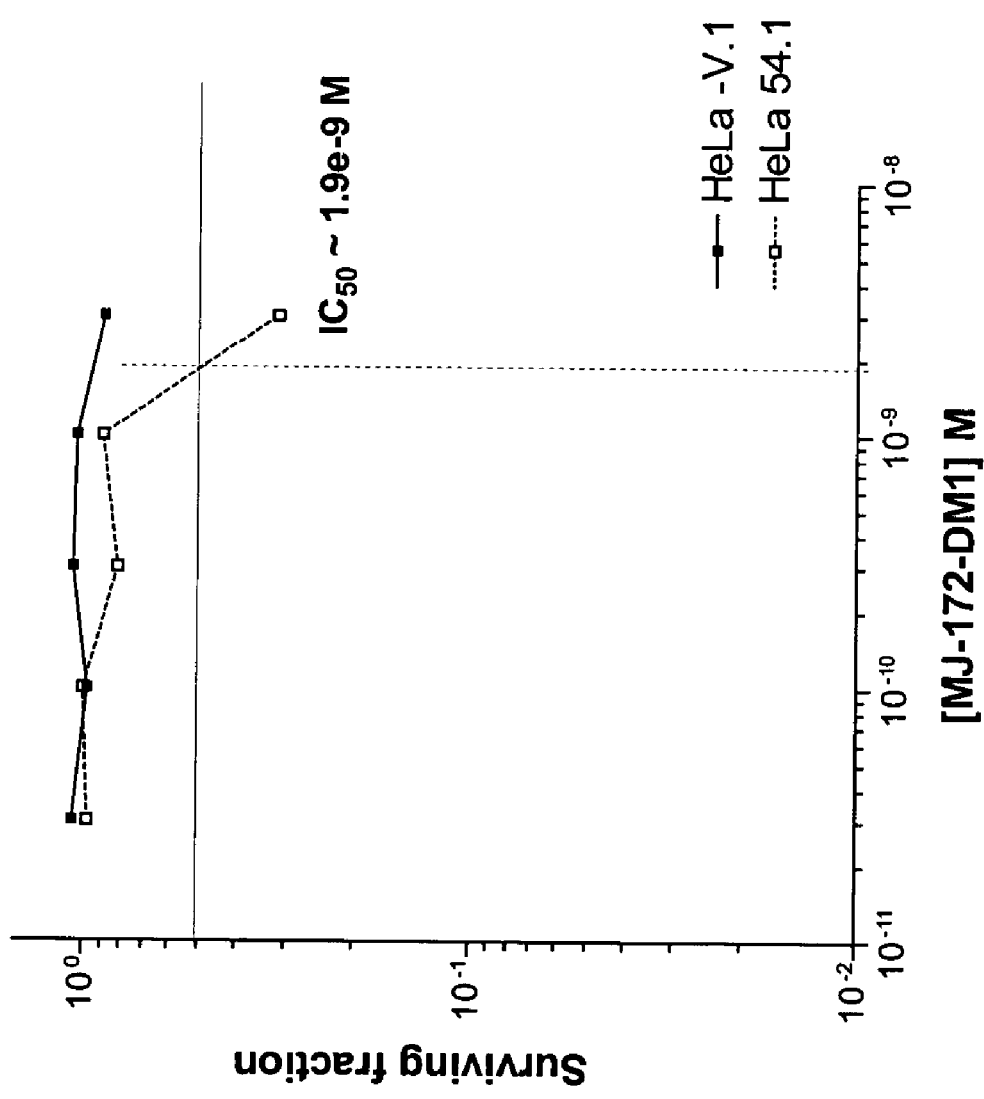
FIG. 16 shows the cytotoxicity of an MJ-172-DM1 conjugate in a continuous exposure clonogenic assay. HeLa/Muc16 Stump#54-1 or HeLa/pcDNA3 (transfected with empty vector) control cells were plated in 6-well plates at a density of 1000 cells per well. Various concentrations of conjugate were added to each well and the cells were incubated until colonies were established (7–8 days). Colonies were fixed and stained with crystal violet/formaldehyde solution and counted.

The results show that HeLa/Muc16 Stump #54-1 cells were selectively killed by MJ-172-DM1 with an estimated $IC_{50}$ of $1.9 \times 10^{-9}$ M (FIG. 16). No toxicity was observed with the control HeLa cell line (stably transfected with empty vector). These results suggest that antibodies recognizing the non-shed domain of Muc16 are able to efficiently deliver cytotoxic drugs such as the maytansinoid, DM1, to kill tumor cells.

Figure 17:
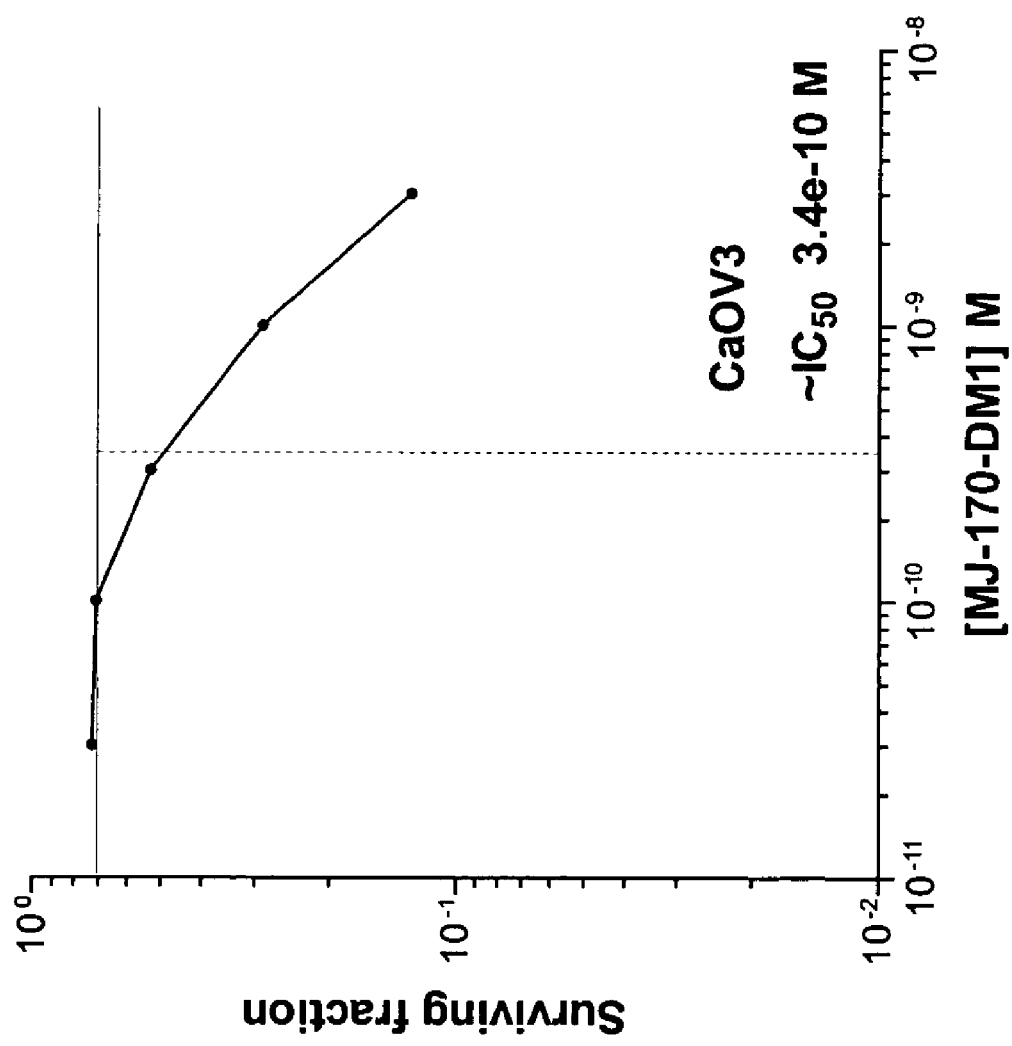
FIG. 17 shows the cytotoxicity of an MJ-170-DM1 conjugate to CaOV3 cells in a continuous exposure clonogenic assay. Cells were plated at a density of 1000 cells per well in a 6-well tissue culture plate. Cells were incubated with the indicated concentrations of conjugate for 7 days at which time colonies were stained and fixed with crystal violet/formaldehyde solution and counted.

For the Muc1 MJ-170-DM1 conjugate, the results showed an $IC_{50}$ estimated to be $3.4 \times 10^{-10}$ (FIG. 17). These results indicate that clone MJ-170 recognizing a non-shed domain of Muc1 is able to efficiently deliver cytotoxic drug to kill tumor cells.

Example 17

Shed Antigen Assay

To demonstrate that MJ-172 and MJ-173 recognize a Muc16 domain which is not shed into the bloodstream of ovarian cancer patients these antibodies were compared with X306, an antibody recognizing shed Muc16, for their ability to capture shed Muc16 either from CanAg CA125 EIA kit standards or ovarian cancer patient sera in a solid phase sandwich ELISA.

To demonstrate that MJ-170 recognizes a non-shed Muc1 domain, it was compared with CM1, the Muc1 VNTR antibody, for ability to capture shed Muc1 either from CanAg CA15-3 EIA kit standards or ovarian cancer patient sera in a solid-phase sandwich ELISA.

Shed antigen in ovarian cancer patient sera was measured using enzyme immunometric kits from CanAg Diagnostics (CA125 EIA kit for Muc16 and CA15-3 EIA kit for Muc1) with some modifications. For Muc16 shed antigen screening, Immunlon H2B 96-well plates were coated with 500 ng per well (100 μl at 5 μg/ml) of either X306 (Advanced ImmunoChemical, Inc.), a CA125-like Mab recognizing the shed Muc16, or Muc16 cell-associated domain antibody (MJ-171 or MJ-172) in 0.5 M carbonate buffer, pH 10 overnight at 4° C. with rocking. The wells were washed three times with 300 μl per well of wash buffer (Tris Buffered Saline (TBS)/0.1% Tween-20) and blocked with 200 μl per well of blocking buffer (TBS/0.1% Tween-20/1% BSA) for 2 hour at room temperature with rocking. Then, 12.5 μl of CA125 standards (0, 10, 40, 200, 500 U/ml) or patient serum sample (which was diluted 1:9 in blocking buffer) was incubated with 50 μl of blocking buffer at room temperature for 2 hours with rocking. The wells were washed three times with 300 μl per well of wash buffer and then the plate was incubated in 40 μl per well of tracer buffer (1:40 dilution of HRP conjugated anti-CA125 in tracer diluent) at room temperature for 1 hour with rocking. The plate was then washed six times with 300 μl per well of wash buffer and developed using 100 μl of tetramethyl benzidine (BioFX Laboratories). The absorbances were read in an EL808 Microplate Reader (Bio-Tek Instruments) at 630 nm.

The ELISA results for MJ-171 and MJ-172 are shown in Table 5. The absorbance at 630 nm for the standards was used to generate a standard curve from which the serum CA125 levels were estimated. In contrast to X306, MJ-171 and MJ-172 exhibited no absorbance values above background (0 U/ml CA125) indicating these antibodies are not able to capture Muc16 shed antigen. However, MJ-171 and MJ-172 are readily able to capture biotinylated Muc16 Peptide a in a ELISA assay of similar format (data not shown). These results confirm that MJ-171 and MJ-172 recognize a Muc16 cell-associated domain rather than a shed domain.

TABLE 5

Muc16 Peptide a Mabs do not bind to Muc 1 shed antigen in ovarian cancer patient sera

| Sample | CA125 (U/ml) | $A_{630}$ X306 | MJ-171 | MJ-172 |
|---|---|---|---|---|
| Standard 1 | 0 | 0.109 | 0.059 | 0.062 |
| Standard 2 | 10 | 0.101 | 0.066 | 0.064 |
| Standard 3 | 40 | 0.142 | 0.074 | 0.065 |
| Standard 4 | 200 | 0.323 | 0.081 | 0.056 |
| Standard 5 | 500 | 0.658 | 0.065 | 0.060 |
| Serum 1 | >500 | 0.719 | 0.072 | 0.062 |
| Serum 2 | 266.4 | 0.132 | 0.072 | 0.072 |
| Serum 3 | <10 | 0.073 | 0.065 | 0.073 |

For Muc1, Immunlon H2B 96-well plates were coated with 250 ng per well (50 μl at 5 μg/ml) of either CM1 (Advanced ImmunoChemical, Inc.), a Muc1 VNTR Mab recognizing shed Muc1, or Muc1 cell-associated domain antibody (MJ-170) in 0.5 M carbonate buffer and the remainder of the procedure essentially as described for Muc16 except 25 μl of CA15-3 standards (0, 15, 50, 125, 250 U/ml) were used.

The ELISA results are shown in Table 6. The absorbance values from CM1 capture of CA15-3 standards were used to generate a standard curve from which the CA515-3 U/ml were calculated for the serum samples. MJ-170 exhibited no evidence of ability to capture Muc1 shed antigen either in CA15-3 standards or in patient sera indicating that this antibody recognizes a non-shed Muc1 domain.

TABLE 6

Muc1 Peptide a Mabs do not bind to Muc 1 shed antigen in ovarian cancer patient sera.

| Sample | CA15-3 (U/ml) | $A_{630}$ CM1 | MJ-170 |
|---|---|---|---|
| Standard 1 | 0 | 0.042 | 0.038 |
| Standard 2 | 15 | 0.103 | 0.046 |
| Standard 3 | 50 | 0.254 | 0.039 |
| Standard 4 | 125 | 0.494 | 0.043 |
| Standard 5 | 250 | 0.735 | 0.038 |
| Serum 1 | 1016.9 | 0.456 | 0.044 |
| Serum 2 | 1550.5 | 0.597 | 0.050 |
| Serum 3 | 503.0 | 0.278 | 0.043 |

Hybridoma Deposit

Each of the four hybridomas discussed above (MJ-170, MJ-171, MJ-172, MJ-173) have been deposited with the American Type Culture Collection, PO Box 1549, Manassas, Va. 20108, on Jun. 24, 24, 24 and 26, 2003, under the Terms of the Budapest Treaty. The Accession Numbers for the four clones are PTA-5286, PTA-5287, PTA-5288 and PTA-5302, respectively.

Certain patents and printed publications have been referred to in the present disclosure, the teachings of which are hereby each incorporated in their respective entireties by reference.

While the invention has been described in detail and with reference to specific embodiments thereof, it will be apparent to one of skill in the art that various changes and modifications can be made thereto without departing from the spirit and scope thereof.

REFERENCES CITED

Baselga, J., Tripathy, D., Mendelsohn, J., Baughman, S., Benz, C. C., Dantis, L., Sklarin, N. T., Seidman, A. D., Hudis, C. A., Moore, J., Rosen, P. P., Twaddell, T., Henderson, I. C., and Norton, L. (1996). Phase II study of weekly intravenous recombinant humanized anti-p185HER2 monoclonal antibody in patients with HER2/neu-overexpressing metastatic breast cancer. J Clin Oncol 14, 737–44.

Bassi, D. E., Mahloogi, H., and Klein-Szanto, A. J. (2000). The proprotein convertases furin and PACE4 play a significant role in tumor progression. Mol Carcinog 28, 63–9.

Bon, G. G., von Mensdorff-Pouilly, S., Kenemans, P., van Kamp, G. J., Verstraeten, R. A., Hilgers, J., Meijer, S., and Vennorken, J. B. (1997). Clinical and technical evaluation of ACS BR serum assay of MUC1 gene-derived glycoprotein in breast cancer, and comparison with CA 15–3 assays. Clin Chem 43, 585–93.

Cannistra, S. A. (1993). Cancer of the ovary. N Engl J Med 329, 1550–9.

Chari, R. V., Martell, B. A., Gross, J. L., Cook, S. B., Shah, S. A., Blattler, W. A., McKenzie, S. J., and Goldmacher, V. S. (1992). Immunoconjugates containing novel maytansinoids: promising anticancer drugs. Cancer Res 52, 127–31.

Devine, P. L., and McKenzie, I. F. (1992). Mucins: structure, function, and associations with malignancy. Bioessays 14, 619–25.

Fendrick, J. L., Konishi, I., Geary, S. M., Parmley, T. H., Quirk, J. G., Jr., and O'Brien, T. J. (1997). CA125 phosphorylation is associated with its secretion from the WISH human amnion cell line. Tumour Biol 18, 278–89.

Harlow, E., and Lane, D. (1988). Antibodies: A Laboratory Manual (Cold Spring Harbor, N.Y., Cold Spring Harbor Laboratory).

Jacobs, I., and Bast, R. C., Jr. (1989). The CA 125 tumour-associated antigen: a review of the literature. Hum Reprod 4, 1–12.

Konishi, I., Fendrick, J. L., Parmley, T. H., Quirk, J. G., Jr., and O'Brien, T. J. (1994). Epidermal growth factor enhances secretion of the ovarian tumor-associated cancer antigen CA125 from the human amnion WISH cell line. J Soc Gynecol Investig 1, 89–96.

Laemmli, U. K. (1970). Cleavage of structural proteins during the assembly of the head of bacteriophage T4. Nature 227, 680–685.

Li, Y., Bharti, A., Chen, D., Gong, J., and Kufe, D. (1998). Interaction of glycogen synthase kinase 3beta with the DF3/MUC1 carcinoma-associated antigen and beta-catenin. Mol Cell Biol 18, 7216–24.

Li, Y., and Kufe, D. (2001). The Human DF3/MUC1 carcinoma-associated antigen signals nuclear localization of the catenin p120(ctn). Biochem Biophys Res Commun 281, 440–3.

Li, Y., Kuwahara, H., Ren, J., Wen, G., and Kufe, D. (2001). The c-Src tyrosine kinase regulates signaling of the human DF3/MUC1 carcinoma-associated antigen with GSK3 beta and beta-catenin. J Biol Chem 276, 606 1–4.

Li, Y., Ren, J., Yu, W., Li, Q., Kuwahara, H., Yin, L., Carraway, K. L., 3rd, and Kufe, D. (2001). The epidermal growth factor receptor regulates interaction of the human DF3/MUC 1 carcinoma antigen with c-Src and beta-catenin. J Biol Chem 276, 35239–42.

Ligtenberg, M. J., Kruijshaar, L., Buijs, F., van Meijer, M., Litvinov, S. V., and Hilkens, J. (1992). Cell-associated episialin is a complex containing two proteins derived from a common precursor. J Biol Chem 267, 6171–7.

Liu, C., Tadayoni, B. M., Bourret, L. A., Mattocks, K. M., Derr, S. M., Widdison, W. C., Kedersha, N. L., Ariniello, P. D., Goldmacher, V. S., Lambert, J. M., Blattler, W. A., and Chari, R. V. (1996). Eradication of large colon tumor xenografts by targeted delivery of maytansinoids. Proc Natl Acad Sci USA 93, 8618–23.

Molloy, S. S., Anderson, E. D., Jean, F., and Thomas, G. (1999). Bi-cycling the furin pathway: from TGN localization to pathogen activation and embryogenesis. Trends Cell Biol 9, 28–35.

O'Brien, T. J., Beard, J. B., Underwood, L. J., Dennis, R. A., Santin, A. D., and York, L. (2001). The CA 125 gene: an extracellular superstructure dominated by repeat sequences. Tumour Biol 22, 348–66.

O'Brien, T. J., Beard, J. B., Underwood, L. J., and Shigemasa, K. (2002). The CA 125 gene: a newly discovered extension of the glycosylated N-terminal domain doubles the size of this extracellular superstructure. Tumour Biol 23, 154–169.

O'Brien, T. J., Tanimoto, H., Konishi, I., and Gee, M. (1998). More than 15 years of CA 125: what is known about the antigen, its structure and its function. Int J Biol Markers 13, 188–95.

Parry, S., Silverman, H. S., McDermott, K., Willis, A., Hollingsworth, M. A., and Harris, A. (2001). Identification of MUC1 proteolytic cleavage sites in vivo. Biochem Biophys Res Commun 283, 715–20.

Pegram, M. D., Lipton, A., Hayes, D. F., Weber, B. L., Baselga, J. M., Tripathy, D., Baly, D., Baughman, S. A., Twaddell, T., Glaspy, J. A., and Slamon, D. J. (1998). Phase II study of receptor-enhanced chemosensitivity using recombinant humanized anti-p 185HER2/neu monoclonal antibody plus cisplatin in patients with HER2/neu-overexpressing metastatic breast cancer refractory to chemotherapy treatment. J Clin Oncol 16, 2659–71.

Taylor-Papadimitriou, J., Burchell, J., Miles, D. W., and Dalziel, M. (1999). MUC1 and cancer. Biochim Biophys Acta 1455, 301–13.

Tolcher, A. W., Ochoa, L., Patnaik, A., Hammond, L., Hildalgo, M., Edwards, T., Drengler, R., Erickson, J., DeWitte, M., Desai, K., Chari, R., Lambert, J., and Rowinsky, E. K. (2001). SB-408075, a Tumor-Activated Prodrug Maytansinoid Immunoconjugate Directed to the C242 Antigen: a Phase I, Pharmacokinetic and Biologic Correlative Study. Proc. Am. Soc. Clin. Oncol. 20, 69a.

What is claimed is:

1. An isolated monoclonal antibody MJ-170 produced by hybridoma cell line MJ-170 on deposit with the American Type Culture Collection (ATCC) as accession number PTA-5286.

2. An isolated monoclonal antibody MJ-171 produced by hybridoma cell line MJ-171 on deposit with the ATCC as accession number PTA-5287.

3. An isolated monoclonal antibody MJ-172 produced by hybridoma cell line MJ-172 on deposit with the ATCC as accession number PTA-5288.

4. An isolated monoclonal antibody MJ-173 produced by hybridoma cell line MJ-173 on deposit with the ATCC as accession number PTA-5302.

5. A hybridoma cell line MJ-170 on deposit with the ATCC as accession number PTA-5286.

6. A hybridoma cell line MJ-171 on deposit with the ATCC as accession number PTA-5287.

7. A hybridoma cell line MJ-172 on deposit with the ATCC as accession number PTA-5288.

8. A hybridoma cell line MJ-173 on deposit with the ATCC as accession number PTA-5302.

9. An antibody of claim 1, 2, 3 or 4, wherein said antibody is covalently linked to a cytotoxic agent or a prodrug of a cytotoxic agent.

10. The antibody of claim 9, wherein said cytotoxic agent is a small drug molecule.

11. The antibody of claim 9, wherein said cytotoxic agent is a maytansinoid, a taxoid, or a CC-1065 analog.

12. A composition comprising an antibody of claim 1, 2, 3 or 4, and a pharmaceutically acceptable carrier.

13. A composition comprising the antibody of claim 9 and a pharmaceutically acceptable carrier.

14. A method of treating a subject having a cancer, comprising administering to a subject having a cancer a therapeutically effective amount of the composition of claim 12.

15. A method of treating a subject having a cancer, comprising administering to a subject having a cancer a therapeutically effective amount of the composition of claim 13.

16. The method of claim 14, wherein said cancer is a cancer wherein Muc1 or Muc16 is overexpressed.

17. The method of claim 15, wherein said cancer is a cancer wherein Muc1 or Muc16 is overexpressed.

18. The method of claim 14, wherein said cancer is ovarian cancer or breast cancer.

19. The method of claim 15, wherein said cancer is ovarian cancer or breast cancer.

20. An isolated antibody that specifically binds to a Muc1 peptide selected from the group consisting of:

| | | |
|---|---|---|
| a) | QLTLAFREGTINVHDVETQFN; | (SEQ ID NO:8) |
| b) | QYKTEAASRYNLTISDVSVSD; | (SEQ ID NO:9) |
| c) | FLQIYKQGGFLGLSNIKFRPG; | (SEQ ID NO:10) |
| and | | |
| d) | VPFPFSAQSGAGVPGWGIA. | (SEQ ID NO:12) |

21. An isolated antibody that specifically binds to a Muc16 peptide selected from the group consisting of:

| | | |
|---|---|---|
| a) | SSVLVDGYSPNRNEPLTGNS; | (SEQ ID NO:14) |
| b) | TNYQRNKRNIEDALNQLFRN; | (SEQ ID NO:15) |
| c) | FRNSSIKSYFSDCQVSTFRSV; | (SEQ ID NO:16) |
| d) | SVPNRHHTGVDSLCNFSPLARRV; | (SEQ ID NO:17) |
| and | | |
| e) | DRVAIYEEFLRMTRNGTQLQNFTLDRSS. | (SEQ ID NO:18) |

22. The antibody of claim 20 or 21, wherein said antibody is selected from the group consisting of a monoclonal antibody, a recombinant antibody, an antigen-binding fragment of a recombinant antibody, a humanized antibody, and an antibody displayed upon the surface of a phage.

23. The antibody of claim 20 or 21, wherein said antibody is covalently linked to a cytotoxic agent or a prodrug of a cytotoxic agent.

24. The antibody of claim 23, wherein said cytotoxic agent is a small drug molecule.

25. The antibody of claim 23, wherein said cytotoxic agent is a maytansinoid, taxoid, or CC-1065 analog.

26. A composition comprising the antibody of claim 20 or 21 and a pharmaceutically acceptable carrier.

27. A composition comprising the antibody of claim 23 and a pharmaceutically acceptable carrier.

28. A method of treating a subject having a cancer, comprising administering to a subject having a cancer a therapeutically effective amount of the composition of claim 26.

29. A method of treating a subject having a cancer, comprising administering to a subject having a cancer a therapeutically effective amount of the composition of claim 27.

30. The method of claim 28, wherein said cancer is a cancer wherein Muc1 or Muc16 is overexpressed.

31. The method of claim 29, wherein said cancer is a cancer wherein Muc1 or Muc16 is overexpressed.

32. The method of claim 28 or 29, wherein said cancer is ovarian cancer or breast cancer.

33. A method of screening a subject for cancer, comprising:
    (a) measuring the amount of Muc1 in a biological sample obtained from a subject using the antibody of claim 20; and
    (b) comparing the amount of Muc1 measured in (a) to the amount of Muc1 in a cancerous and a non-cancerous control, thereby screening a subject for cancer.

34. A method of screening a subject for cancer, comprising:
    (a) measuring the amount of Muc16 in a biological sample obtained from a subject using the antibody of claim 21; and
    (b) comparing the amount of Muc16 measured in (a) to the amount of Muc16 in a cancerous and a non-cancerous control, thereby screening a subject for cancer.

35. The method of claim 33 or 34, wherein said cancer is ovarian cancer or breast cancer.

36. A hybridoma that produces an antibody that specifically binds to a MUC1 peptide selected from the group consisting of:

a) QLTLAFREGTINVHDVETQFN (SEQ ID NO:8);
b) QYKTEAASRYNLTISDVSVSD (SEQ ID NO:9);
c) FLQIYKQGGFLGLSNIKFRPG (SEQ ID NO:10); and
d) VPFPFSAQSGAGVPGWGIA (SEQ ID NO:12).

37. A hybridoma that produces an antibody that specifically binds to a MUC16 peptide selected from the group consisting of:

a) SSVLVDGYSPNRNEPLTGNS (SEQ ID NO:14);
b) TNYQRNKRNIEDALNQLFRN (SEQ ID NO:15);
c) FRNSSIKSYFSDCQVSTFRSV (SEQ ID NO:16);
d) SVPNRHHTGVDSLCNFSPLARRV (SEQ ID NO:17); and
e) DRVAIYEEFLRMTRNGTQLQNFTLDRSS (SEQ ID NO:18).

* * * * *

SEQUENCE LISTING

```
<160> NUMBER OF SEQ ID NOS: 33

<210> SEQ ID NO 1
<211> LENGTH: 86
<212> TYPE: PRT
<213> ORGANISM: Homo sapiens

<400> SEQUENCE: 1

Phe Leu Gln Ile Tyr Lys Gln Gly Gly Phe Leu Gly Leu Ser Asn Ile
1               5                   10                  15

Lys Phe Arg Pro Gly Ser Val Val Val Gln Leu Thr Leu Ala Phe Arg
            20                  25                  30

Glu Gly Thr Ile Asn Val His Asp Val Glu Thr Gln Phe Asn Gln Tyr
        35                  40                  45

Lys Thr Glu Ala Ala Ser Arg Tyr Asn Leu Thr Ile Ser Asp Val Ser
    50                  55                  60
```

```
Val Ser Asp Val Pro Phe Pro Phe Ser Ala Gln Ser Ala Gly Val
 65                  70                  75                  80

Pro Gly Trp Gly Ile Ala
                85

<210> SEQ ID NO 2
<211> LENGTH: 108
<212> TYPE: PRT
<213> ORGANISM: Homo sapiens

<400> SEQUENCE: 2

Thr Asn Tyr Gln Arg Asn Lys Arg Asn Ile Glu Asp Ala Leu Asn Gln
  1               5                  10                  15

Leu Phe Arg Asn Ser Ser Ile Lys Ser Tyr Phe Ser Asp Cys Gln Val
                 20                  25                  30

Ser Thr Phe Arg Ser Val Pro Asn Arg His His Thr Gly Val Asp Ser
             35                  40                  45

Leu Cys Asn Phe Ser Pro Leu Ala Arg Arg Val Asp Arg Val Ala Ile
         50                  55                  60

Tyr Glu Glu Phe Leu Arg Met Thr Arg Asn Gly Thr Gln Leu Gln Asn
 65                  70                  75                  80

Phe Thr Leu Asp Arg Ser Ser Val Leu Val Asp Gly Tyr Ser Pro Asn
                 85                  90                  95

Arg Asn Glu Pro Leu Thr Gly Asn Ser Asp Leu Pro
                100                 105

<210> SEQ ID NO 3
<211> LENGTH: 20
<212> TYPE: PRT
<213> ORGANISM: Homo sapiens

<400> SEQUENCE: 3

Pro Asp Thr Arg Pro Ala Pro Gly Ser Thr Ala Pro Ala His Gly
  1               5                  10                  15

Val Thr Ser Ala
            20

<210> SEQ ID NO 4
<211> LENGTH: 25
<212> TYPE: PRT
<213> ORGANISM: Homo sapiens

<400> SEQUENCE: 4

Phe Trp Ala Val Ile Leu Ile Gly Leu Ala Gly Leu Leu Gly Leu Ile
  1               5                  10                  15

Thr Cys Leu Ile Cys Gly Val Leu Val
                 20                  25

<210> SEQ ID NO 5
<211> LENGTH: 4
<212> TYPE: PRT
<213> ORGANISM: Homo sapiens

<400> SEQUENCE: 5

Arg Asn Lys Arg
  1

<210> SEQ ID NO 6
<211> LENGTH: 4
<212> TYPE: PRT
<213> ORGANISM: Homo sapiens
```

```
<400> SEQUENCE: 6

Ser Pro Leu Ala
1

<210> SEQ ID NO 7
<211> LENGTH: 86
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(1)
<223> OTHER INFORMATION: Glutathione S-transferase fusion site

<400> SEQUENCE: 7

Phe Leu Gln Ile Tyr Lys Gln Gly Gly Phe Leu Gly Leu Ser Asn Ile
1               5                  10                  15

Lys Phe Arg Pro Gly Ser Val Val Gln Leu Thr Leu Ala Phe Arg
            20                  25                  30

Glu Gly Thr Ile Asn Val His Asp Val Glu Thr Gln Phe Asn Gln Tyr
            35                  40                  45

Lys Thr Glu Ala Ala Ser Arg Tyr Asn Leu Thr Ile Ser Asp Val Ser
    50                  55                  60

Val Ser Asp Val Pro Phe Pro Phe Ser Ala Gln Ser Gly Ala Gly Val
65                  70                  75                  80

Pro Gly Trp Gly Ile Ala
                85

<210> SEQ ID NO 8
<211> LENGTH: 21
<212> TYPE: PRT
<213> ORGANISM: Homo sapiens

<400> SEQUENCE: 8

Gln Leu Thr Leu Ala Phe Arg Glu Gly Thr Ile Asn Val His Asp Val
1               5                  10                  15

Glu Thr Gln Phe Asn
            20

<210> SEQ ID NO 9
<211> LENGTH: 21
<212> TYPE: PRT
<213> ORGANISM: Homo sapiens

<400> SEQUENCE: 9

Gln Tyr Lys Thr Glu Ala Ala Ser Arg Tyr Asn Leu Thr Ile Ser Asp
1               5                  10                  15

Val Ser Val Ser Asp
            20

<210> SEQ ID NO 10
<211> LENGTH: 21
<212> TYPE: PRT
<213> ORGANISM: Homo sapiens

<400> SEQUENCE: 10

Phe Leu Gln Ile Tyr Lys Gln Gly Gly Phe Leu Gly Leu Ser Asn Ile
1               5                  10                  15

Lys Phe Arg Pro Gly
            20
```

```
<210> SEQ ID NO 11
<211> LENGTH: 21
<212> TYPE: PRT
<213> ORGANISM: Homo sapiens

<400> SEQUENCE: 11

Phe Arg Pro Gly Ser Val Val Gln Leu Thr Leu Ala Phe Arg Glu
1               5                   10                  15

Gly Thr Ile Asn Val
            20

<210> SEQ ID NO 12
<211> LENGTH: 19
<212> TYPE: PRT
<213> ORGANISM: Homo sapiens

<400> SEQUENCE: 12

Val Pro Phe Pro Phe Ser Ala Gln Ser Gly Ala Gly Val Pro Gly Trp
1               5                   10                  15

Gly Ile Ala

<210> SEQ ID NO 13
<211> LENGTH: 108
<212> TYPE: PRT
<213> ORGANISM: Artificial Sequence
<220> FEATURE:
<223> OTHER INFORMATION: Fusion protein
<220> FEATURE:
<221> NAME/KEY: MISC_FEATURE
<222> LOCATION: (1)..(1)
<223> OTHER INFORMATION: Glutathione S-transferase fusion site

<400> SEQUENCE: 13

Thr Asn Tyr Gln Arg Asn Lys Arg Asn Ile Glu Asp Ala Leu Asn Gln
1               5                   10                  15

Leu Phe Arg Asn Ser Ser Ile Lys Ser Tyr Phe Ser Asp Cys Gln Val
            20                  25                  30

Ser Thr Phe Arg Ser Val Pro Asn Arg His His Thr Gly Val Asp Ser
        35                  40                  45

Leu Cys Asn Phe Ser Pro Leu Ala Arg Arg Val Asp Arg Val Ala Ile
    50                  55                  60

Tyr Glu Glu Phe Leu Arg Met Thr Arg Asn Gly Thr Gln Leu Gln Asn
65                  70                  75                  80

Phe Thr Leu Asp Arg Ser Ser Val Leu Val Asp Gly Tyr Ser Pro Asn
                85                  90                  95

Arg Asn Glu Pro Leu Thr Gly Asn Ser Asp Leu Pro
            100                 105

<210> SEQ ID NO 14
<211> LENGTH: 20
<212> TYPE: PRT
<213> ORGANISM: Homo sapiens

<400> SEQUENCE: 14

Ser Ser Val Leu Val Asp Gly Tyr Ser Pro Asn Arg Asn Glu Pro Leu
1               5                   10                  15

Thr Gly Asn Ser
            20

<210> SEQ ID NO 15
```

```
<211> LENGTH: 20
<212> TYPE: PRT
<213> ORGANISM: Homo sapiens

<400> SEQUENCE: 15

Thr Asn Tyr Gln Arg Asn Lys Arg Asn Ile Glu Asp Ala Leu Asn Gln
1               5                   10                  15

Leu Phe Arg Asn
            20

<210> SEQ ID NO 16
<211> LENGTH: 21
<212> TYPE: PRT
<213> ORGANISM: Homo sapiens

<400> SEQUENCE: 16

Phe Arg Asn Ser Ser Ile Lys Ser Tyr Phe Ser Asp Cys Gln Val Ser
1               5                   10                  15

Thr Phe Arg Ser Val
            20

<210> SEQ ID NO 17
<211> LENGTH: 23
<212> TYPE: PRT
<213> ORGANISM: Homo sapiens

<400> SEQUENCE: 17

Ser Val Pro Asn Arg His His Thr Gly Val Asp Ser Leu Cys Asn Phe
1               5                   10                  15

Ser Pro Leu Ala Arg Arg Val
            20

<210> SEQ ID NO 18
<211> LENGTH: 28
<212> TYPE: PRT
<213> ORGANISM: Homo sapiens

<400> SEQUENCE: 18

Asp Arg Val Ala Ile Tyr Glu Glu Phe Leu Arg Met Thr Arg Asn Gly
1               5                   10                  15

Thr Gln Leu Gln Asn Phe Thr Leu Asp Arg Ser Ser
            20                  25

<210> SEQ ID NO 19
<211> LENGTH: 515
<212> TYPE: PRT
<213> ORGANISM: Artificial Sequence
<220> FEATURE:
<223> OTHER INFORMATION: Exemplary Muc1 protein

<400> SEQUENCE: 19

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80
```

-continued

```
Ala Pro Ala Thr Glu Pro Ala Ser Gly Ser Ala Ala Thr Trp Gly Gln
                85                  90                  95
Asp Val Thr Ser Val Pro Val Thr Arg Pro Ala Leu Gly Ser Thr Thr
            100                 105                 110
Pro Pro Ala His Asp Val Thr Ser Ala Pro Asp Asn Lys Pro Ala Pro
        115                 120                 125
Gly Ser Thr Ala Pro Pro Ala His Gly Val Thr Ser Ala Pro Asp Thr
    130                 135                 140
Arg Pro Pro Pro Gly Ser Thr Ala Pro Pro Ala His Gly Val Thr Ser
145                 150                 155                 160
Ala Pro Asp Thr Arg Pro Pro Gly Ser Thr Ala Pro Ala Ala His
                165                 170                 175
Gly Val Thr Ser Ala Pro Asp Thr Arg Pro Ala Pro Gly Ser Thr Ala
                180                 185                 190
Pro Pro Ala His Gly Val Thr Ser Ala Pro Asp Asn Arg Pro Ala Leu
            195                 200                 205
Ala Ser Thr Ala Pro Pro Val His Asn Val Thr Ser Ala Ser Gly Ser
        210                 215                 220
Ala Ser Gly Ser Ala Ser Thr Leu Val His Asn Gly Thr Ser Ala Arg
225                 230                 235                 240
Ala Thr Thr Thr Pro Ala Ser Lys Ser Thr Pro Phe Ser Ile Pro Ser
                245                 250                 255
His His Ser Asp Thr Pro Thr Thr Leu Ala Ser His Ser Thr Lys Thr
            260                 265                 270
Asp Ala Ser Ser Thr His His Ser Thr Val Pro Pro Leu Thr Ser Ser
        275                 280                 285
Asn His Ser Thr Ser Pro Gln Leu Ser Thr Gly Val Ser Phe Phe
    290                 295                 300
Leu Ser Phe His Ile Ser Asn Leu Gln Phe Asn Ser Ser Leu Glu Asp
305                 310                 315                 320
Pro Ser Thr Asp Tyr Tyr Gln Glu Leu Gln Arg Asp Ile Ser Glu Met
                325                 330                 335
Phe Leu Gln Ile Tyr Lys Gln Gly Gly Phe Leu Gly Leu Ser Asn Ile
            340                 345                 350
Lys Phe Arg Pro Gly Ser Val Val Gln Leu Thr Leu Ala Phe Arg
        355                 360                 365
Glu Gly Thr Ile Asn Val His Asp Val Glu Thr Gln Phe Asn Gln Tyr
    370                 375                 380
Lys Thr Glu Ala Ala Ser Arg Tyr Asn Leu Thr Ile Ser Asp Val Ser
385                 390                 395                 400
Val Ser Asp Val Pro Phe Pro Phe Ser Ala Gln Ser Gly Ala Gly Val
                405                 410                 415
Pro Gly Trp Gly Ile Ala Leu Leu Val Leu Val Cys Val Leu Val Ala
            420                 425                 430
Leu Ala Ile Val Tyr Leu Ile Ala Leu Ala Val Cys Gln Cys Arg Arg
        435                 440                 445
Lys Asn Tyr Gly Gln Leu Asp Ile Phe Pro Ala Arg Asp Thr Tyr His
    450                 455                 460
Pro Met Ser Glu Tyr Pro Thr Tyr His Thr His Gly Arg Tyr Val Pro
465                 470                 475                 480
Pro Ser Ser Thr Asp Arg Ser Pro Tyr Glu Lys Val Ser Ala Gly Asn
                485                 490                 495
Gly Gly Ser Ser Leu Ser Tyr Thr Asn Pro Ala Val Ala Ala Thr Ser
```

```
                500             505             510
Ala Asn Leu
        515

<210> SEQ ID NO 20
<211> LENGTH: 2234
<212> TYPE: PRT
<213> ORGANISM: Artificial Sequence
<220> FEATURE:
<223> OTHER INFORMATION: Exemplary Muc16 protein

<400> SEQUENCE: 20

Met Glu His Ile Thr Lys Ile Pro Asn Glu Ala Ala His Arg Gly Thr
1               5                   10                  15

Ile Arg Pro Val Lys Gly Pro Gln Thr Ser Thr Ser Pro Ala Ser Pro
            20                  25                  30

Lys Gly Leu His Thr Gly Gly Thr Lys Arg Met Glu Thr Thr Thr Thr
        35                  40                  45

Ala Leu Lys Thr Thr Thr Thr Ala Leu Lys Thr Thr Ser Arg Ala Thr
    50                  55                  60

Leu Thr Thr Ser Val Tyr Thr Pro Thr Leu Gly Thr Leu Thr Pro Leu
65                  70                  75                  80

Asn Ala Ser Arg Gln Met Ala Ser Thr Ile Leu Thr Glu Met Met Ile
                85                  90                  95

Thr Thr Pro Tyr Val Phe Pro Asp Val Pro Glu Thr Thr Ser Ser Leu
            100                 105                 110

Ala Thr Ser Leu Gly Ala Glu Thr Ser Thr Ala Leu Pro Arg Thr Thr
        115                 120                 125

Pro Ser Val Leu Asn Arg Glu Ser Glu Thr Thr Ala Ser Leu Val Ser
    130                 135                 140

Arg Ser Gly Ala Glu Arg Ser Pro Val Ile Gln Thr Leu Asp Val Ser
145                 150                 155                 160

Ser Ser Glu Pro Asp Thr Thr Ala Ser Trp Val Ile His Pro Ala Glu
                165                 170                 175

Thr Ile Pro Thr Val Ser Lys Thr Thr Pro Asn Phe Phe His Ser Glu
            180                 185                 190

Leu Asp Thr Val Ser Ser Thr Ala Thr Ser His Gly Ala Asp Val Ser
        195                 200                 205

Ser Ala Ile Pro Thr Asn Ile Ser Pro Ser Glu Leu Asp Ala Leu Thr
    210                 215                 220

Pro Leu Val Thr Ile Ser Gly Thr Asp Thr Ser Thr Thr Phe Pro Thr
225                 230                 235                 240

Leu Thr Lys Ser Pro His Glu Thr Glu Thr Arg Thr Thr Trp Leu Thr
                245                 250                 255

His Pro Ala Glu Thr Ser Ser Thr Ile Pro Arg Thr Ile Pro Asn Phe
            260                 265                 270

Ser His His Glu Ser Asp Ala Thr Pro Ser Ile Ala Thr Ser Pro Gly
        275                 280                 285

Ala Glu Thr Ser Ser Ala Ile Pro Ile Met Thr Val Ser Pro Gly Ala
    290                 295                 300

Glu Asp Leu Val Thr Ser Gln Val Thr Ser Ser Gly Thr Asp Arg Asn
305                 310                 315                 320

Met Thr Ile Pro Thr Leu Thr Leu Ser Pro Gly Glu Pro Lys Thr Ile
                325                 330                 335

Ala Ser Leu Val Thr His Pro Glu Ala Gln Thr Ser Ser Ala Ile Pro
```

-continued

```
                340                 345                 350
Thr Ser Thr Ile Ser Pro Ala Val Ser Arg Leu Val Thr Ser Met Val
            355                 360                 365
Thr Ser Leu Ala Ala Lys Thr Ser Thr Asn Arg Ala Leu Thr Asn
            370                 375             380
Ser Pro Gly Glu Pro Ala Thr Thr Val Ser Leu Val Thr His Pro Ala
385                 390                 395                 400
Gln Thr Ser Pro Thr Val Pro Trp Thr Thr Ser Ile Phe Phe His Ser
                405                 410                 415
Lys Ser Asp Thr Thr Pro Ser Met Thr Thr Ser His Gly Ala Glu Ser
            420                 425                 430
Ser Ser Ala Val Pro Thr Pro Thr Val Ser Thr Glu Val Pro Gly Val
            435                 440                 445
Val Thr Pro Leu Val Thr Ser Ser Arg Ala Val Ile Ser Thr Thr Ile
        450                 455                 460
Pro Ile Leu Thr Leu Ser Pro Gly Glu Pro Glu Thr Thr Pro Ser Met
465                 470                 475                 480
Ala Thr Ser His Gly Glu Glu Ala Ser Ser Ala Ile Pro Thr Pro Thr
                485                 490                 495
Val Ser Pro Gly Val Pro Gly Val Val Thr Ser Leu Val Thr Ser Ser
            500                 505                 510
Arg Ala Val Thr Ser Thr Thr Ile Pro Ile Leu Thr Phe Ser Leu Gly
        515                 520                 525
Glu Pro Glu Thr Thr Pro Ser Met Ala Thr Ser His Gly Thr Glu Ala
    530                 535                 540
Gly Ser Ala Val Pro Thr Val Leu Pro Glu Val Pro Gly Met Val Thr
545                 550                 555                 560
Ser Leu Val Ala Ser Ser Arg Ala Val Thr Ser Thr Thr Leu Pro Thr
                565                 570                 575
Leu Thr Leu Ser Pro Gly Glu Pro Glu Thr Thr Pro Ser Met Ala Thr
            580                 585                 590
Ser His Gly Ala Glu Ala Ser Ser Thr Val Pro Thr Val Ser Pro Glu
        595                 600                 605
Val Pro Gly Val Val Thr Ser Leu Val Thr Ser Ser Ser Gly Val Asn
    610                 615                 620
Ser Thr Ser Ile Pro Thr Leu Ile Leu Ser Pro Gly Glu Leu Glu Thr
625                 630                 635                 640
Thr Pro Ser Met Ala Thr Ser His Gly Ala Glu Ala Ser Ser Ala Val
                645                 650                 655
Pro Thr Pro Thr Val Ser Pro Gly Val Ser Gly Val Val Thr Pro Leu
            660                 665                 670
Val Thr Ser Ser Arg Ala Val Thr Ser Thr Thr Ile Pro Ile Leu Thr
        675                 680                 685
Leu Ser Ser Ser Glu Pro Glu Thr Thr Pro Ser Met Ala Thr Ser His
    690                 695                 700
Gly Val Glu Ala Ser Ser Ala Val Leu Thr Val Ser Pro Glu Val Pro
705                 710                 715                 720
Gly Met Val Thr Ser Leu Val Thr Ser Ser Arg Ala Val Thr Ser Thr
                725                 730                 735
Thr Ile Pro Thr Leu Thr Ile Ser Ser Asp Glu Pro Glu Thr Thr Thr
            740                 745                 750
Ser Leu Val Thr His Ser Glu Ala Lys Met Ile Ser Ala Ile Pro Thr
        755                 760                 765
```

-continued

```
Leu Ala Val Ser Pro Thr Val Gln Gly Leu Val Thr Ser Leu Val Thr
770                 775                 780

Ser Ser Gly Ser Glu Thr Ser Ala Phe Ser Asn Leu Thr Val Ala Ser
785                 790                 795                 800

Ser Gln Pro Glu Thr Ile Asp Ser Trp Val Ala His Pro Gly Thr Glu
                805                 810                 815

Ala Ser Ser Val Val Pro Thr Leu Thr Val Ser Thr Gly Glu Pro Phe
            820                 825                 830

Thr Asn Ile Ser Leu Val Thr His Pro Ala Glu Ser Ser Thr Leu
        835                 840                 845

Pro Arg Thr Thr Ser Arg Phe Ser His Ser Glu Leu Asp Thr Met Pro
850                 855                 860

Ser Thr Val Thr Ser Pro Glu Ala Glu Ser Ser Ala Ile Ser Thr
865                 870                 875                 880

Thr Ile Ser Pro Gly Ile Pro Gly Val Leu Thr Ser Leu Val Thr Ser
                885                 890                 895

Ser Gly Arg Asp Ile Ser Ala Thr Phe Pro Thr Val Pro Glu Ser Pro
            900                 905                 910

His Glu Ser Glu Ala Thr Ala Ser Trp Val Thr His Pro Ala Val Thr
        915                 920                 925

Ser Thr Thr Val Pro Arg Thr Thr Pro Asn Tyr Ser His Ser Glu Pro
930                 935                 940

Asp Thr Thr Pro Ser Ile Ala Thr Ser Pro Gly Ala Glu Ala Thr Ser
945                 950                 955                 960

Asp Phe Pro Thr Ile Thr Val Ser Pro Asp Val Pro Asp Met Val Thr
                965                 970                 975

Ser Gln Val Thr Ser Ser Gly Thr Asp Thr Ser Ile Thr Ile Pro Thr
            980                 985                 990

Leu Thr Leu Ser Ser Gly Glu Pro Glu Thr Thr Thr Ser Phe Ile Thr
        995                 1000                1005

Tyr Ser Glu Thr His Thr Ser Ser Ala Ile Pro Thr Leu Pro Val
    1010                1015                1020

Ser Pro Gly Ala Ser Lys Met Leu Thr Ser Leu Val Ile Ser Ser
    1025                1030                1035

Gly Thr Asp Ser Thr Thr Thr Phe Pro Thr Leu Thr Glu Thr Pro
    1040                1045                1050

Tyr Glu Pro Glu Thr Thr Ala Ile Gln Leu Ile His Pro Ala Glu
    1055                1060                1065

Thr Asn Thr Met Val Pro Lys Thr Thr Pro Lys Phe Ser His Ser
    1070                1075                1080

Lys Ser Asp Thr Thr Leu Pro Val Ala Ile Thr Ser Pro Gly Pro
    1085                1090                1095

Glu Ala Ser Ser Ala Val Ser Thr Thr Thr Ile Ser Pro Asp Met
    1100                1105                1110

Ser Asp Leu Val Thr Ser Leu Val Pro Ser Ser Gly Thr Asp Thr
    1115                1120                1125

Ser Thr Thr Phe Pro Thr Leu Ser Glu Thr Pro Tyr Glu Pro Glu
    1130                1135                1140

Thr Thr Val Thr Trp Leu Thr His Pro Ala Glu Thr Ser Thr Thr
    1145                1150                1155

Val Ser Gly Thr Ile Pro Asn Phe Ser His Arg Gly Ser Asp Thr
    1160                1165                1170
```

-continued

```
Ala Pro Ser Met Val Thr Ser Pro Gly Val Asp Thr Arg Ser Gly
1175                1180                1185

Val Pro Thr Thr Thr Ile Pro Pro Ser Ile Pro Gly Val Val Thr
    1190                1195                1200

Ser Gln Val Thr Ser Ser Ala Thr Asp Thr Ser Thr Ala Ile Pro
1205                1210                1215

Thr Leu Thr Pro Ser Pro Gly Glu Pro Glu Thr Thr Ala Ser Ser
1220                1225                1230

Ala Thr His Pro Gly Thr Gln Thr Gly Phe Thr Val Pro Ile Arg
1235                1240                1245

Thr Val Pro Ser Ser Glu Pro Asp Thr Met Ala Ser Trp Val Thr
1250                1255                1260

His Pro Pro Gln Thr Ser Thr Pro Val Ser Arg Thr Thr Ser Ser
1265                1270                1275

Phe Ser His Ser Ser Pro Asp Ala Thr Pro Val Met Ala Thr Ser
1280                1285                1290

Pro Arg Thr Glu Ala Ser Ser Ala Val Leu Thr Thr Ile Ser Pro
1295                1300                1305

Gly Ala Pro Glu Met Val Thr Ser Gln Ile Thr Ser Ser Gly Ala
1310                1315                1320

Ala Thr Ser Thr Thr Val Pro Thr Leu Thr His Ser Pro Gly Met
1325                1330                1335

Pro Glu Thr Thr Ala Leu Leu Ser Thr His Pro Arg Thr Gly Thr
1340                1345                1350

Ser Lys Thr Phe Pro Ala Ser Thr Val Phe Pro Gln Val Ser Glu
1355                1360                1365

Thr Thr Ala Ser Leu Thr Ile Arg Pro Gly Ala Glu Thr Ser Thr
1370                1375                1380

Ala Leu Pro Thr Gln Thr Thr Ser Ser Leu Phe Thr Leu Leu Val
1385                1390                1395

Thr Gly Thr Ser Arg Val Asp Leu Ser Pro Thr Ala Ser Pro Gly
1400                1405                1410

Val Ser Ala Lys Thr Ala Pro Leu Ser Thr His Pro Gly Thr Glu
1415                1420                1425

Thr Ser Thr Met Ile Pro Thr Ser Thr Leu Ser Leu Gly Leu Leu
1430                1435                1440

Glu Thr Thr Gly Leu Leu Ala Thr Ser Ser Ser Ala Glu Thr Ser
1445                1450                1455

Thr Ser Thr Leu Thr Leu Thr Val Ser Pro Ala Val Ser Gly Leu
1460                1465                1470

Ser Ser Ala Ser Ile Thr Thr Asp Lys Pro Gln Thr Val Thr Ser
1475                1480                1485

Trp Asn Thr Glu Thr Ser Pro Ser Val Thr Ser Val Gly Pro Pro
1490                1495                1500

Glu Phe Ser Arg Thr Val Thr Gly Thr Thr Met Thr Leu Ile Pro
1505                1510                1515

Ser Glu Met Pro Thr Pro Pro Lys Thr Ser His Gly Glu Gly Val
1520                1525                1530

Ser Pro Thr Thr Ile Leu Arg Thr Thr Met Val Glu Ala Thr Asn
1535                1540                1545

Leu Ala Thr Thr Gly Ser Ser Pro Thr Val Ala Lys Thr Thr Thr
1550                1555                1560

Thr Phe Asn Thr Leu Ala Gly Ser Leu Phe Thr Pro Leu Thr Thr
```

-continued

```
            1565                1570                1575

Pro Gly Met Ser Thr Leu Ala Ser Glu Ser Val Thr Ser Arg Thr
    1580                1585                1590

Ser Tyr Asn His Arg Ser Trp Ile Ser Thr Thr Ser Ser Tyr Asn
    1595                1600                1605

Arg Arg Tyr Trp Thr Pro Ala Thr Ser Thr Pro Val Thr Ser Thr
    1610                1615                1620

Phe Ser Pro Gly Ile Ser Thr Ser Ser Ile Pro Ser Ser Thr Ala
    1625                1630                1635

Ala Thr Val Pro Phe Met Val Pro Phe Thr Leu Asn Phe Thr Ile
    1640                1645                1650

Thr Asn Leu Gln Tyr Glu Glu Asp Met Arg His Pro Gly Ser Arg
    1655                1660                1665

Lys Phe Asn Ala Thr Glu Arg Glu Leu Gln Gly Leu Leu Lys Pro
    1670                1675                1680

Leu Phe Arg Asn Ser Ser Leu Glu Tyr Leu Tyr Ser Gly Cys Arg
    1685                1690                1695

Leu Ala Ser Leu Arg Pro Glu Lys Asp Ser Ser Ala Met Ala Val
    1700                1705                1710

Asp Ala Ile Cys Thr His Arg Pro Asp Pro Glu Asp Leu Gly Leu
    1715                1720                1725

Asp Arg Glu Arg Leu Tyr Trp Glu Leu Ser Asn Leu Thr Asn Gly
    1730                1735                1740

Ile Gln Glu Leu Gly Pro Tyr Thr Leu Asp Arg Asn Ser Leu Tyr
    1745                1750                1755

Val Asn Gly Phe Thr His Arg Ser Ser Met Pro Thr Thr Ser Thr
    1760                1765                1770

Pro Gly Thr Ser Thr Val Asp Val Gly Thr Ser Gly Thr Pro Ser
    1775                1780                1785

Ser Ser Pro Ser Pro Thr Ala Ala Gly Pro Leu Leu Met Pro Phe
    1790                1795                1800

Thr Leu Asn Phe Thr Ile Thr Asn Leu Gln Tyr Glu Glu Asp Met
    1805                1810                1815

Arg Arg Thr Gly Ser Arg Lys Phe Asn Thr Met Glu Ser Val Leu
    1820                1825                1830

Gln Gly Leu Leu Lys Pro Leu Phe Lys Asn Thr Ser Val Gly Pro
    1835                1840                1845

Leu Tyr Ser Gly Cys Arg Leu Thr Leu Leu Arg Pro Glu Lys Asp
    1850                1855                1860

Gly Ala Ala Thr Gly Val Asp Ala Ile Cys Thr His Arg Leu Asp
    1865                1870                1875

Pro Lys Ser Pro Gly Leu Asn Arg Glu Gln Leu Tyr Trp Glu Leu
    1880                1885                1890

Ser Lys Leu Thr Asn Asp Ile Glu Glu Leu Gly Pro Tyr Thr Leu
    1895                1900                1905

Asp Arg Asn Ser Leu Tyr Val Asn Gly Phe Thr His Gln Ser Ser
    1910                1915                1920

Val Ser Thr Thr Ser Thr Pro Gly Thr Ser Thr Val Asp Leu Arg
    1925                1930                1935

Thr Ser Gly Thr Pro Ser Ser Leu Ser Ser Pro Thr Ile Thr Leu
    1940                1945                1950

Leu Arg Asp Ile Gln Asp Lys Val Thr Thr Leu Tyr Lys Gly Ser
    1955                1960                1965
```

```
Gln Leu His Asp Thr Phe Arg Phe Cys Leu Val Thr Asn Leu Thr
    1970                1975                1980

Met Asp Ser Val Leu Val Thr Val Lys Ala Leu Phe Ser Ser Asn
    1985                1990                1995

Leu Asp Pro Ser Leu Val Glu Gln Val Phe Leu Asp Lys Thr Leu
    2000                2005                2010

Asn Ala Ser Phe His Trp Leu Gly Ser Thr Tyr Gln Leu Val Asp
    2015                2020                2025

Ile His Val Thr Glu Met Glu Ser Ser Val Tyr Gln Pro Thr Ser
    2030                2035                2040

Ser Ser Ser Thr Gln His Phe Tyr Pro Asn Phe Thr Ile Thr Asn
    2045                2050                2055

Leu Pro Tyr Ser Gln Asp Lys Ala Gln Pro Gly Thr Thr Asn Tyr
    2060                2065                2070

Gln Arg Asn Lys Arg Asn Ile Glu Asp Ala Leu Asn Gln Leu Phe
    2075                2080                2085

Arg Asn Ser Ser Ile Lys Ser Tyr Phe Ser Asp Cys Gln Val Ser
    2090                2095                2100

Thr Phe Arg Ser Val Pro Asn Arg His His Thr Gly Val Asp Ser
    2105                2110                2115

Leu Cys Asn Phe Ser Pro Leu Ala Arg Arg Val Asp Arg Val Ala
    2120                2125                2130

Ile Tyr Glu Glu Phe Leu Arg Met Thr Arg Asn Gly Thr Gln Leu
    2135                2140                2145

Gln Asn Phe Thr Leu Asp Arg Ser Ser Val Leu Val Asp Gly Tyr
    2150                2155                2160

Ser Pro Asn Arg Asn Glu Pro Leu Thr Gly Asn Ser Asp Leu Pro
    2165                2170                2175

Phe Trp Ala Val Ile Leu Ile Gly Leu Ala Gly Leu Leu Gly Leu
    2180                2185                2190

Ile Thr Cys Leu Ile Cys Gly Val Leu Val Thr Thr Arg Arg Arg
    2195                2200                2205

Lys Lys Glu Gly Glu Tyr Asn Val Gln Gln Gln Cys Pro Gly Tyr
    2210                2215                2220

Tyr Gln Ser His Leu Asp Leu Glu Asp Leu Gln
    2225                2230

<210> SEQ ID NO 21
<211> LENGTH: 710
<212> TYPE: DNA
<213> ORGANISM: Homo sapiens

<400> SEQUENCE: 21
ggatccatga caccgggcac ccagtctcct ttcttcctgc tgctgctcct cacagtgctt    60
acagttgtta caggttctgg tcatgcaagc tctaccgact acaaggacga cgatgacaag   120
tctagattcc gaaacagcag catcaagagt tattttttctg actgtcaagt ttcaacattc   180
aggtctgtcc caacaggca ccacaccggg gtggactccc tgtgtaactt ctcgccactg    240
gctcggagag tagacagagt tgccatctat gaggaatttc tgcggatgac ccggaatggt   300
acccagctgc agaacttcac cctggacagg agcagtgtcc ttgtggatgg gtattctccc   360
aacagaaatg agcccttaac tgggaattct gaccttccct tctgggctgt catcctcatc   420
ggcttggcag gactcctggg actcatcaca tgcctgatct gcggtgtcct ggtgaccacc   480
```

```
cgccggcgga agaaggaagg agaatacaac gtccagcaac agtgcccagg ctactaccag    540
tcacacctag acctggagga tctgcaagcg gccgctcgag ccaccatgga acaaaaactc    600
atctcagaag aggatctggc tagcgaacaa aaactcatct cagaagagga tctggaacaa    660
aaactcatct cagaagagga tctgaccggt taaatgcatc tagagggccc              710
```

<210> SEQ ID NO 22
<211> LENGTH: 29
<212> TYPE: DNA
<213> ORGANISM: Artificial Sequence
<220> FEATURE:
<223> OTHER INFORMATION: PCR primer

<400> SEQUENCE: 22

```
ttttaagctt accatgccct tttcaagaa                                       29
```

<210> SEQ ID NO 23
<211> LENGTH: 30
<212> TYPE: DNA
<213> ORGANISM: Artificial Sequence
<220> FEATURE:
<223> OTHER INFORMATION: PCR primer

<400> SEQUENCE: 23

```
tttgatatct cattgcagat cctccaggtc                                      30
```

<210> SEQ ID NO 24
<211> LENGTH: 29
<212> TYPE: DNA
<213> ORGANISM: Artificial Sequence
<220> FEATURE:
<223> OTHER INFORMATION: PCR primer

<400> SEQUENCE: 24

```
gggagccggg ttggcccatg tccgccatg                                       29
```

<210> SEQ ID NO 25
<211> LENGTH: 30
<212> TYPE: DNA
<213> ORGANISM: Artificial Sequence
<220> FEATURE:
<223> OTHER INFORMATION: PCR primer

<400> SEQUENCE: 25

```
atgggccaac ccggctccct caagttcaac                                      30
```

<210> SEQ ID NO 26
<211> LENGTH: 41
<212> TYPE: DNA
<213> ORGANISM: Artificial Sequence
<220> FEATURE:
<223> OTHER INFORMATION: PCR primer

<400> SEQUENCE: 26

```
ttttaagctt caccatgccc ttgttcaaga acaccagtgt c                         41
```

<210> SEQ ID NO 27
<211> LENGTH: 35
<212> TYPE: DNA
<213> ORGANISM: Artificial Sequence
<220> FEATURE:
<223> OTHER INFORMATION: PCR primer

<400> SEQUENCE: 27

```
ttttggatcc tcattgcaga tcctccaggt ctagg                                35
```

```
<210> SEQ ID NO 28
<211> LENGTH: 32
<212> TYPE: DNA
<213> ORGANISM: Artificial Sequence
<220> FEATURE:
<223> OTHER INFORMATION: PCR primer

<400> SEQUENCE: 28
aaaagcggcc gcttgcagat cctccaggtc ta                              32

<210> SEQ ID NO 29
<211> LENGTH: 21
<212> TYPE: DNA
<213> ORGANISM: Artificial Sequence
<220> FEATURE:
<223> OTHER INFORMATION: PCR primer

<400> SEQUENCE: 29
gaatggtacc cagctgcaga a                                          21

<210> SEQ ID NO 30
<211> LENGTH: 22
<212> TYPE: DNA
<213> ORGANISM: Artificial Sequence
<220> FEATURE:
<223> OTHER INFORMATION: PCR primer

<400> SEQUENCE: 30
gctgggtacc attccgggtc at                                         22

<210> SEQ ID NO 31
<211> LENGTH: 30
<212> TYPE: DNA
<213> ORGANISM: Artificial Sequence
<220> FEATURE:
<223> OTHER INFORMATION: PCR primer

<400> SEQUENCE: 31
caagtctaga ttccgaaaca gcagcatcaa                                 30

<210> SEQ ID NO 32
<211> LENGTH: 31
<212> TYPE: DNA
<213> ORGANISM: Artificial Sequence
<220> FEATURE:
<223> OTHER INFORMATION: PCR primer

<400> SEQUENCE: 32
ttttggatcc atcacaccgg gcacccagtc t                               31

<210> SEQ ID NO 33
<211> LENGTH: 56
<212> TYPE: DNA
<213> ORGANISM: Artificial Sequence
<220> FEATURE:
<223> OTHER INFORMATION: PCR primer

<400> SEQUENCE: 33
ggaatctaga cttgtcatcg tcgtccttgt agtcggtaga gcttgcatga ccagaa    56
```